United States Patent
Espley et al.

(10) Patent No.: US 7,973,216 B2
(45) Date of Patent: Jul. 5, 2011

(54) COMPOSITIONS AND METHODS FOR MODULATING PIGMENT PRODUCTION IN PLANTS

(75) Inventors: Richard Espley, Auckland (NZ); Roger Hellens, Auckland (NZ); Andrew C. Allan, Auckland (NZ)

(73) Assignee: The New Zealand Institute for Plant and food Research Limited, Auckland (NZ)

( * ) Notice: Subject to any disclaimer, the term of this patent is extended or adjusted under 35 U.S.C. 154(b) by 0 days.

(21) Appl. No.: 12/065,251

(22) PCT Filed: Aug. 30, 2006

(86) PCT No.: PCT/NZ2006/000221
§ 371 (c)(1),
(2), (4) Date: Jul. 16, 2008

(87) PCT Pub. No.: WO2007/027105
PCT Pub. Date: Mar. 8, 2007

(65) Prior Publication Data
US 2011/0072539 A1 Mar. 24, 2011

(30) Foreign Application Priority Data

Aug. 30, 2005 (NZ) ...................................... 542110

(51) Int. Cl.
A01H 5/00 (2006.01)
C12N 15/82 (2006.01)
C07H 21/00 (2006.01)
(52) U.S. Cl. ...... 800/295; 800/278; 800/298; 435/320.1; 435/419; 435/468; 536/23.2; 536/23.6
(58) Field of Classification Search .......................... None
See application file for complete search history.

(56) References Cited

U.S. PATENT DOCUMENTS

| | | | |
|---|---|---|---|
| 4,795,855 | A | 1/1989 | Fillatti et al. |
| 5,004,863 | A | 4/1991 | Umbeck |
| 5,159,135 | A | 10/1992 | Umbeck |
| 5,177,010 | A | 1/1993 | Goldman et al. |
| 5,187,073 | A | 2/1993 | Goldman et al. |
| 5,188,958 | A | 2/1993 | Moloney et al. |
| 5,416,011 | A | 5/1995 | Hinchee et al. |
| 5,463,174 | A | 10/1995 | Moloney et al. |
| 5,563,455 | A | 10/1996 | Cheng |
| 5,569,834 | A | 10/1996 | Hinchee et al. |
| 5,591,616 | A | 1/1997 | Hiei et al. |
| 5,750,871 | A | 5/1998 | Moloney et al. |
| 5,792,935 | A | 8/1998 | Arntzen et al. |
| 5,824,877 | A | 10/1998 | Hinchee et al. |
| 5,846,797 | A | 12/1998 | Strickland |
| 5,952,543 | A | 9/1999 | Firoozabady et al. |
| 5,968,830 | A | 10/1999 | Dan et al. |
| 5,981,840 | A | 11/1999 | Zhao et al. |
| 6,020,539 | A | 2/2000 | Goldman et al. |
| 6,037,522 | A | 3/2000 | Dong et al. |
| 6,074,877 | A | 6/2000 | D'Halluin et al. |
| 2004/0034888 | A1 | 2/2004 | Liu et al. |

FOREIGN PATENT DOCUMENTS

| | | |
|---|---|---|
| WO | WO 01/59103 | 8/2001 |
| WO | WO 02/00894 | 1/2002 |
| WO | WO 02/055658 | 7/2002 |
| WO | WO 03/084312 | 10/2003 |
| WO | WO 2004/096994 | 11/2004 |
| WO | WO 2005/001050 | 1/2005 |

OTHER PUBLICATIONS

Bovy et al. (Plant Cell, 14:2509-2526, Published 2002).*
Wells (Biochemistry 29:8509-8517, 1990).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Ngo et al., (The Protein Folding Problem and Tertiary Structure Prediction, K. Merz., and S. Le Grand (eds.) pp. 492-495,1994).*
Doerks et al., (TIG, 14:248-250, 1998).*
Smith et al. (Nature Biotechnology, 15:1222-1223, 1997).*
Bork et al. (TIG, 12:425-427, 1996).*
Vom Endt et al. (Phytochemistry 61:107-114, 2002).*
Korban et al. (NCBI, GenBank Sequence Accession No. CV628545, Published Oct. 25, 2004).*
Accession No. AJ554700, Jan. 5, 2004, "Gerbera Hybrid cv. 'Terra Regina' mRNA for MYB10 Protein," Eloma et al.
Accession No. Q8L5P3, Oct. 1, 2002, "SubName: Full=Myb-Related Transcription Factor V1MYBA1-1," Kobayashi et al.
GenBank Accession No. DQ267896, Jul. 21, 2006, Malus x domestica Cultivar RedField MYB10a mRNA, Partial cds, Espley et al.
GenBank Accession No. DQ267897, Jul. 21, 2006, "Malus x domestica Cultivar Pacicic Rose MEYB10a mRNA, Partial cds," Espley et al.
GenBank Accession No. DQ267898, Jul. 21, 2006, "Mauls x domestica Cultivar Granny Smith NYB10a mRNA, Partial cds," Allan et al.
GenBank Accession No. DQ886415, Nov. 18, 2006, "Malus x domestica MYB Transcription Factor (MYB1) Gene, MYB1-2 allele, Promoter Region and Complete cds," Takos et al.
GenBank Accession No. DQ267900, Jul. 21 2006, "Malus x domestica Cultivar Royal Gala MYB9 mRNA, Complete cds," Allan et al.
GenBank Accession No. AF336284, Mar. 15, 2001, "Gossypium hirsutum GHMYB36 (ghmyb36) mRNA, Complete cds," Matz et al.
GenBank Accession No. DQ074463, Jan. 24, 2006, Malus x domestica MYB11 mRNA, Complete cds, Hellens et al.

(Continued)

Primary Examiner — Vinod Kumar
(74) Attorney, Agent, or Firm — Greenlee Sullivan PC

(57) ABSTRACT

This invention relates to polynucleotides encoding novel transcription factors and to the encoded transcription factors, that are capable of regulating anthocyanin production in plants. The invention also relates to constructs and vectors comprising the polynucleotides, and to host cells, plant cells and plants transformed with the polynucleotides, constructs and vectors. The invention also relates to methods of producing plants with altered anthocyanin production and plants by the methods.

16 Claims, 11 Drawing Sheets

OTHER PUBLICATIONS

GenBank Accession No. CN 938023, Jun. 7, 2004.
GenBank Accession No. CN 934367, Jun. 7, 2004.
GenBank Accession No. AF 117267, Apr. 20, 1999, "Malus domestica UDP Glucose: Flavonoid 3-0-glucsyl Tranferase (UFGT1) mRNA, Complete cds," Lee et al.
GenBank Accession No. AF 117269, Apr. 20, 1999, Malus domestica Anthocyanidin Synthase (ANS) mRNA, Complete cds, Lee et al.
GenBank Accession No. AY 227729, Mar. 27, 2003, Malus x domestica Cultivar Weirouge dihydroflavonol 4-Reductase mRNA, Complete cds, Fischer et al.
GenBank Accession No. CN 491664, Apr. 27, 2004, Korban et al.
GenBank Accession No. CN 946541, Jun. 7, 2004, Beuning et al.
GenBank Accession No. CN 944824, Jun. 7, 2004, Beuning et al.
GenBank Accession No. AF325123, Feb. 7, 2001, "Arabidopsis thaliana Production of Anthocyanin Pigment 1 Protein (PAP1) Gene, Complete cds," Borovitz et al.
GenBank Accession No. AF146702, May 1, 2000, Petunia x hybrida An2 Protein (an2) mRNA, an2-V26 allele, Complete cds, Quattrocchio et al.
SwissProt Accession No. Q6V7VO Jul. 5, 2004, "Anthcyanin 1," Mathews et al.
SwissProt Accession No. Q9ATD3, Jun. 1, 2001, "GHMYB36," Matz et al.
SwissProt Accession No. Q9ATD5 Jun. 1, 2001, "GHMYB10," Matz et al.
SwissProt Accession No. Q6QP46, Jul. 5, 2004, "Anthocyanin Biocynthesis Regulatory Protein P11_B73," Swigonova et al.
Abbott et al. (Mar. 2002) "Simultaneous Suppression of Multiple Genes by Single Transgenes. Down-Regulation of Three Unrelated Lignin Biosynthetic Genes in Tobacco," *Plant Physiol.* 128(3):844-853.
Aharoni et al. (2001) "The Strawberry FaMYB1 Transcription Factor Suppresses Anthocyanin and Flavonol Accumulation in Transgenic Tobacco," *Plant J.* 28: 319-332.
Altschul et al. (1997) "Gapped BLAST and PSI-BLAST: A New Generation of Protein Database Search Programs," *Nucleic Acids Res.* 25(17):3389-3402.
Bairoch et al. (1994) "PROSITE: Recent Developments," *Nuc. Acids Res.* 22(17):3583-3589.
Bolton et al. (1962) "A General Method for the Isolation of RNA Complementary to DNA," *Proc. Nat. Acad. Sci. USA* 48:1390-1397.
Borevitz et al. (Dec. 2000) "Activation Tagging Identifies a Conserved MYB Regulator of Phenylprooanoid Biosynthesis," *Plant Cell* 12: 2383-2394.
Boss et al. (1996) "Expression of Anthocyanin Biosynthesis Pathway Aenes in Red and White Grapes," *Plant Mol. Biol.* 32: 56fr569.
Bovy et al, (Oct. 2002) "High-Flavonol Tomatoes Resulting from the Heterologous Expression of the Maize Transcription Factor Genes LC and CI," The Plant Cell, 14: 2509-2526.
Broun, P. (2005) "Transcriptional Control of Flavonoid Biosynthesis: a Complex Network of Conserved Regulators Involved in Multiple Aspects of Differentiation in Arabidopsis," *Curr. Opin. Plant. Biol.* 8: 272-279.
de Carvalho Niebel et al. (Mar. 1995) "Post Transcriptional Cosuppression of β-1,3-Glucanase Genes Does Not Affect Accumulation of Transgene Nuclear mRNA," *Plant Cell* 7:347-358.
Elomaa et al. (Dec. 2003) "Activation of Anthocyanin Biosynthesis in Gerbera hybrida (Asteraceae) Suggests Conserved Proteinprotein and Protein-Promoter Interactions Between the Anciently Diverged Monocots and Eudicots," *Plant Phys. Biochem.* 133:1831-1842.
Espley et al. (2007) "Red Colouration in Apple Fruit is Due to the Activity of the MYB Transription Factor, MdMYB10," *Plant J.* 49:414-427.
Falquet et al. (2002) "The PROSITE Database, it's Status in 2002," *Nuc. Acids Res.* 30(1):235-238.
Giesen et al. (Nov 1, 1998) "A Formula for Thermal Stability ($T_m$) Prediction of PNA/DNA Duplexes," *Nuc. Acids Res.* 26(21):5004-5006.
Grotewold et al. (Dec. 5, 2000) "Identification of the Residues in the Myb Domain of Maize C1 that Specify the Interaction with the bHLH Cofactor R," *Proc. Nat. Acad. Sci. USA* 97:13579-13584.

Heim et al. (2003) "The Basic Helix-Loop-Helix Transcription Factor Family in Plants: A Genome-Wide Study of Protein Structure and Functional Diversity," *Mol. Biol. Evol.* 20:735-747.
Hofmann et al. (1999) "The PROSITE Database, it's Status in 1999," *Nuc. Acids. Res.* 27(1):215-219.
Holton et al. (Jul. 1995) "Genetics and Biochemistry of Anthocyanin Biosynthesis," *Plant Cell* 7:1071-1083.
Honda et al. (2002) "Anthocyanin Biosynthetic Genes are Coordinately Expressed During Red Coloration in Apple Skin," *Plant Physiol. Biochem.* 40:955-962.
International Search Report, Corresponding to International Application No. PCT/NZ2006/000221, Mailed Feb. 22, 2007.
Jin et al. (1999) "Multifunctionality and Diversity within the Plant MYB-Gene Family," *Plant Mol. Biol.* 41:577-585.
Jouvenot et al. (2003) "Targeted Regulation of Imprinted Genes by Synthetic Zinc-Finger Transcription Factors," *Gene Ther.* 10:513-522.
Kim et al. (2003) "Molecular Cloning and Analysis of Anthocyanin Biosynthesis Genes Preferentially Expressed in Apple Skin," *Plant Sci.* 165:403-413.
Kobayashi et al. (2002) "*Myb*-Related Geens of the Kyoho Grape (*Vitis labruscana*) Regulate Anthocyanin Biosynthesis," *Planta* 215:924-933.
Kubo (Jul. 1999) "Anthocyanless2, a Homeobox Gene Affecting Anthocyanin Distribution and Root Development in Arabidopsism" *Plant Cell.* 11:1217-1226.
Lancaster J. (1992) "Regulation of Skin Color in Apples," *Crit Rec. Plant Sci.* 10:487-502.
Mathews et al. (Aug. 2003) "Ativation Tagging in Tomato Identifies a Transcriptional Regulator of Anthocyanin Biosynthesis, Modification, and Transport," *The Plant Cell* 15:1689-1703.
Mehrtens et al. (Jun. 2005) "The Arabidopsis Transcription Factor MYB12 is a Flavonol-Specific Regulator of Phenylpropanoid Biosynthesis," *Plant Phys.* 138:1083-1096.
Mol et al. (1996) "Signal Perception, Transduction, and Gene Expression Involved in Anthocyanin Biosynthesis," *Crit. Rev. Plant. Sci.* 15(5-6):525-557.
Napoli et al. (Apr. 1990) "Introduction of a Chimeric Chalone Synthase Gene into Petunia Results in Reversible Co-Suppression of Homologous In Trans," *Plant Cell* 2:279-289.
Nesi et al. (Sep. 2001) "The Arabidopsis T12 Gene Encodes an R2R3 MYB Domain Protein that Acts as a Key Determinant for Proanthocyanidin Accumulation in Developing Seed," *Plant Cell* 13:2099-2114.
Page R. (1996) "TreeView: An Application to Display Phylogenetic Trees on Personal Computers," *Comput. Applic. Biosci.* 12(4):357-358.
Piazza et al. (Mar. 2002) "Members of the c1/pII Regulatory Gene Family Mediate the Response of Maize Aleurone and Mesocotyl to Different Light Qualities and Cytokinins," *Plant Phys.* 128:1077-1086.
Quattrocchio et al. (1998) "Analysis of bHLH and MYB Domain Proteins: Species-Specific Regulatory Differences are Caused by Divergent Evolution of Taraet Anthocyanin Genes," *Plant J.* 13(4):475-488.
Quattrocchio et al. (Aug. 1999) "Molecular Analysis of the *anthocyanin2* Gene of Petunia and its Role in the Evolution of Flower Color," *Plant Cell* 11:1433-1444.
Saito et al. (2002) "Biochemistry and Molecular Biology of the Late-Stage of Biosynthesis of Anthocyanin: Lessons from *Perilla frutescens* as a Model Plant," *New Phytologist* 155:9-23.
Schwinn et al. (2004) "Flavonoids," In; Davies, K.M. ed, *Plant Pigments and their Manipulation*, vol. 14. Blackwell Oxford, pp. 92-149.
Stracke et al. (2001) "The R2R3-MYB Gene Family in *Arabidopsis thaliana*," *Curr. Opin. Plant Biol.* 4:447-456.
Supplementary European Search Report, Corresponding to European Application No. EP 06 78 4027, Completed Sep. 23, 2008.

Triqlia et al. (1998) "A Procedure for in vitro Amplification of DNA Segments that Lie Outside the Boundaries of Known Sequences," *Nuc. Acids Res.* 16(16):8186.

Walker et al. (Jul. 1999) "The Transparent Testa Glabrai Locus, Which Regulates Trichome Differentiation and Anthocyanin Biosynthesis in Arabidopsis, Encodes a WD40 Repeat Protein," *Plant Cell* 11:1337-1350.

Goff, et al. Transactivation of Anthocyanin Biosynthetic Genes Following Transfer of B Regulatory Genes Into Maize Tissues, The EMBO Journal, 1990, pp. 2517-2522, vol. 9, No. 8, Oxford University Press.

\* cited by examiner

```
                  *        20         *        40         *        60         *        80
AtMYB75   : MEGSSKGLRKG---AWTTEDSLLRQCINKYGEGKWHQVPVRAGLRCRKSCRLRWLNYLKPSIKRGKLSSDEVDLLLRLH : 78
Co_(Quince: MEG   NLSVMRKGAWT  ED LLRQCIGIIGEGKWHQVP KTGL RCRKSCRLRWLNYLKP IKRGD T DEVDLIIRLH : 81
Ej_(loquat: MEG   NLRVKRKGAWT  ED LLRQCI IIGEGKWHQVP K GL RCRKSCRLRWLNYVKP IKRGD T DEVDLIIRLH : 81
Md_(apple): MEG   ENLSVR-KGAWT  ED LLRQCV IHGEGKWNQVS K GL RCRKSCRLRWLNYLKP IKRGD K DEVDLIIRLH : 80
Ms_(crab_a: MEG   ENLSVR-KGAWT  ED LLRQCV IHGEGKWNQVS K GL RCRKSCRLRWLNYLKP IKRGD K DEVDLIIRLH : 80
Pb_(pear_Y: MEG   NLSVR-KGAWT  ED LLRQCI IHGEGKWNQVS K GL RCRKSCRQRWLNYLKP IKRGD K DEVDLILRLH : 80
Pc_(pear) : MEG   NLSVR-KGAWT  ED LLRQCI IHGEGKWNQVS K GL RCRKSCRQRWLNYLKP IKRGD K DEVDLILRLH : 80
Pcf_(cherr: MEG   GVRKG---AWT KED LLRQCI K GEGKWHQVP K GLSRCRRSCRLRWLNYLKP IKRGD M DEVDLIIRLH : 78
Ppr_(peach: MEG   GVRKG---AWT  ED LLRQCI NHGEGKWHPNK GL RCRKSCRLRWMNYLKP KRGE A DEVDLIIRLH : 78
Ppy_(pear_: MEG   NLSVR-KGAWT  ED LLRQCI IHGEGKWNQVS K GL RCRKSCRQRWLNYLKP IKRGD K DEVDLILRLH : 80
Ps_(Japane: MEG   GVRKG---AWT KED LLRQCI KHGEGKWHQVP K GLSRCRRSCRLRWLNYLKP IKRGD M DEVDLIIRLH : 78
Pav_(sweet: MEG   GVRKG---AWT  ED LLRQCI NQGEGKWHQVP K GL RCRRSCRLRWLNYLKP TKRGD M DEVDLIIRLH : 78
Pd_(almond: MEG   GVRKG---AWT  ED LLRQCI NQGEGKWHQVP K GLKRCRRSCRLRWVNYLKP KRGE A DEVDLIIRLH : 78
Mg_(medlar: MEG   NLSVR-KGAWT  ED LLRQCI IHGEGKWNQVS K GL RCRKSCRLRWLNYLKP SIKRGD K DEVDLIIRLH : 80
Pdm_(Europ: MEG   GVRKG---AWT  ED LLRQCI NHGEGKWHQVP K GL RCRKSCRLRWLNYLKP IKRGE A DEVDLIIRLH : 78
            MEGyn   6       AWTr ED LLRQC6e  GEGKW QV y4aGLnRCR4SCR RW6NY6KPnIKRG f eDEVDL66RLH

*       100         *       120         *       140         *       160
AtMYB75   : RLLGNRWSLIAGRLIGRTANVKNY THLSKKHEPCCKIKMKK D TPIPTTPALKNNVYPRPRSETVNNDCNHLNAPP : 159
Co_(Quince: KLLGNRWSLIAGRLQGRTANVKNY  T L -------T SR T TSQ SQ RK IV P PRSEI YY S  GP : 153
Ej_(loquat: KLLGNRWSLIAGRLQGRTANVKNYC T L -------T SR TSQ SQ  RK IV P PRSEI NY S GP : 153
Md_(apple): RLLGNRWSLIARRLIGRTANAVKNY  T L -------T SR T S Q -MRE NV P PQKEN  YY SS P : 152
Ms_(crab_a: RLLGNRWSLIARRLIGRTANAVKNY  T L -------T SR T S Q -MRE NV P PQKEN  YY SS P : 152
Pb_(pear_Y: RLLGNRWSLIARRLIGRTANVKNY  T LG-------T SR T S Q -RK NV P PQKEI  YY SS P : 152
Pc_(pear) : RLLGNRWSLIARRLIGRTANVKNY  T L -------T SR T S Q -RK NV P PQKEI  YY SS P : 152
Pcf_(cherr: KLLGNRWSLIARRLIGRTAN VKNY  T L -------K YC K   II IR-P PRSFT NC F P : 149
Ppr_(peach: KLLGNRWSLIAGRLIGRTANVKNY  T L -------T SR T P Q -II IV P PQKFI NC S P : 150
Ppy_(pear_: RLLGNRWSLIARRLIGRTANVKNY  T LG-------T SR T S Q -R NV P PQKEI  YY S P : 152
Ps_(Japane: KLLGNRWSLIARRLIGRTAN VKNY  T L -------T YC K S  II IR-P PRRFT NC F P : 149
Pav_(sweet: KLLGNRWSLIAQRLIGRTANVKNY  T L -------M YS K S  II II P PRSFT NC F P : 150
Pd_(almond: KLLGNRWSLIAGRLIGRTANVKNY  T L -------T SR K P -II IV P PQKFI NC S P : 150
Mg_(medlar: KLLGNRWSLIAQRLIGRTANVKNY  T L -------M YS K S  II II P PRSFI NC S P : 152
Pdm_(Europ: KLLGNRWSLIAGRLIGRTANVKNY  T L --------K P  II IV P PRSFI NC S P : 144
            4LLGNRWSLIA RLpGRTANdVKNYwnTrLr                k k qe t kt 6i PqP F  ss  ls kePi

*       180         *       200         *       220         *       240
AtMYB75   : KVDVN---------PPCLGLNINNVCDNSIYNKDKKKDQLVNNLDGDN-WLEKELEE--SQEVDILVPEATTTEKGDT : 228
Co_(Quince: D  SA       S  S   N  N    TLFEG-EDTF  ACPS E E   FT  WF R SAR--S A P F QS SE : 231
Ej_(loquat: D  SE  S   S  L K-N  N R    TLLKD-EGTF  TAYPSFE E   FT  A EMQQSARSCTVS P  PS SN : 232
Md_(apple): D  SA  L   P  S  N  N      TLLEG-EDTF  AYPS E E   FT  WF R SPR--S A P  HS SE : 229
Ms_(crab_a: D I SA  L   P  S  N  N      TLLEG-EDTF  AYPS E E   FT  WF R SPR--S A P  QS SE : 229
Pb_(pear_Y: E  T SA  L   S  S   N  N    TLFEG-EDTF  ACPS E E   FT  WF R SAR--S A P  QS SE : 230
Pc_(pear) : E   SA  L   S  S   N  N     TLFEG-EDTF  ACPS E E   FT  WF R SAR--S A P  QS SE : 230
Pcf_(cherr: D T LE  F  S  T  I SE     TFLDD-KDAT  DTGSG G D   LAS V  D PQSTRI V S  LS GD : 229
Ppr_(peach: D   T V  F  S  S   P  N     TFLDD-EDVF   TCYG A  E FT  V   PQSKRO T VS E GLG GD : 229
Ppy_(pear_: E  T SA  L   S  S   N  N    TLFEG-EDTF  ACPS E E   FT  WF R SAR--S A P  QS SE : 230
Ps_(Japane: D TLE   F  TS  I T   IS     TFLDD-KDAT T TGSG G D   LA  V  D PQSTRT V  LS GD : 229
Pav_(sweet: D T LE  F   S  T    SE     TFLDD-KDA   TGSG G D   LA  V  D PQSTR I S  LS GD : 230
Pd_(almond: D  T                R--     TFLDDKDA -  TGSG G D   LA  V  D PQSTRK I S  LI GD : 211
Mg_(medlar: D T LE V F  T  S   ISE     TFLDDKDA  -  TGSGGGD   LA  V  D PQSTRT I S  LS GE : 232
Pdm_(Europ: D T V LE   S  SS  KN N      TFLDDEDVF-   TCYG A  E  FT V   PQSKRO T VT E LGTGD : 223
             l  h q   e  stp q s  t    g dwwe3       e a   l ee  f5 dd       c nf e  g

*       260
AtMYB75   : LA D QLWSLFDGETVKFD : 248
Co_(Quince:   V  E       ------ : 245
Ej_(loquat: L  N  V       ------ : 246
Md_(apple):    T  K       ------ : 243
Ms_(crab_a:    T          ------ : 243
Pb_(pear_Y:              ------ : 244
Pc_(pear) :              ------ : 244
Pcf_(cherr:              ------ : 243
Ppr_(peach:              ------ : 243
Ppy_(pear_:              ------ : 244
Ps_(Japane:              ------ : 243
Pav_(sweet:              ------ : 244
Pd_(almond:    P          ------ : 225
Mg_(medlar: L  T       KNS----- : 247
Pdm_(Europ:    N          ------ : 237
            fsfs dlwnhskee
```

Figure 9

| | AtMYB75 | Co (Quince) | Ej (loquat) | Md (apple) | Ms (crab apple) | Pb (pear YALI) | Pc (pear) | Pcf (cherry plum) | Ppr (peach) | Ppy (pear Nashi) | Ps (Japanese plum) | Pav (sweet cherry) | Pd (almond) | Mg (medlar) | Pdm (European plum) |
|---|---|---|---|---|---|---|---|---|---|---|---|---|---|---|---|
| AtMYB75 | 100 | 37 | 37 | 36 | 36 | 37 | 36 | 40 | 40 | 37 | 40 | 40 | 44 | 38 | 41 |
| Co (Quince) | | 100 | 81 | 89 | 89 | 92 | 92 | 70 | 75 | 92 | 70 | 71 | 66 | 72 | 72 |
| Ej (loquat) | | | 100 | 77 | 77 | 78 | 79 | 69 | 72 | 78 | 68 | 69 | 65 | 71 | 70 |
| Md (apple) | | | | 100 | 99 | 92 | 93 | 69 | 73 | 92 | 69 | 69 | 66 | 74 | 69 |
| Ms (crab apple) | | | | | 100 | 94 | 94 | 69 | 73 | 94 | 69 | 69 | 66 | 74 | 69 |
| Pb (pear YALI) | | | | | | 100 | 98 | 70 | 74 | 100 | 69 | 70 | 65 | 74 | 70 |
| Pc (pear) | | | | | | | 100 | 70 | 75 | 98 | 70 | 70 | 65 | 74 | 71 |
| Pcf (cherry plum) | | | | | | | | 100 | 83 | 70 | 97 | 94 | 81 | 86 | 80 |
| Ppr (peach) | | | | | | | | | 100 | 74 | 83 | 84 | 82 | 78 | 93 |
| Ppy (pear Nashi) | | | | | | | | | | 100 | 69 | 70 | 65 | 74 | 70 |
| Ps (Japanese plum) | | | | | | | | | | | 100 | 92 | 82 | 86 | 80 |
| Pav (sweet cherry) | | | | | | | | | | | | 100 | 86 | 91 | 82 |
| Pd (almond) | | | | | | | | | | | | | 100 | 79 | 79 |
| Mg (medlar) | | | | | | | | | | | | | | 100 | 77 |
| Pdm (European plum) | | | | | | | | | | | | | | | 100 |

SEQUENCE LISTING

<160> NUMBER OF SEQ ID NOS: 119

<210> SEQ ID NO 1
<211> LENGTH: 243
<212> TYPE: PRT
<213> ORGANISM: Malus domestica

<400> SEQUENCE: 1

```
Met Glu Gly Tyr Asn Glu Asn Leu Ser Val Arg Lys Gly Ala Trp Thr
1               5                   10                  15

Arg Glu Glu Asp Asn Leu Leu Arg Gln Cys Val Glu Ile His Gly Glu
            20                  25                  30

Gly Lys Trp Asn Gln Val Ser Tyr Lys Ala Gly Leu Asn Arg Cys Arg
        35                  40                  45

Lys Ser Cys Arg Leu Arg Trp Leu Asn Tyr Leu Lys Pro Asn Ile Lys
50                  55                  60

Arg Gly Asp Phe Lys Glu Asp Glu Val Asp Leu Ile Ile Arg Leu His
65                  70                  75                  80

Arg Leu Leu Gly Asn Arg Trp Ser Leu Ile Ala Arg Arg Leu Pro Gly
                85                  90                  95

Arg Thr Ala Asn Ala Val Lys Asn Tyr Trp Asn Thr Arg Leu Arg Ile
            100                 105                 110

Asp Ser Arg Met Lys Thr Val Lys Asn Lys Ser Gln Glu Met Arg Glu
        115                 120                 125

Thr Asn Val Ile Arg Pro Gln Pro Gln Lys Phe Asn Arg Ser Ser Tyr
    130                 135                 140

Tyr Leu Ser Ser Lys Glu Pro Ile Leu Asp His Ile Gln Ser Ala Glu
145                 150                 155                 160

Asp Leu Ser Thr Pro Pro Gln Thr Ser Ser Thr Lys Asn Gly Asn
                165                 170                 175

Asp Trp Trp Glu Thr Leu Leu Glu Gly Glu Asp Thr Phe Glu Arg Ala
            180                 185                 190

Ala Tyr Pro Ser Ile Glu Leu Glu Glu Leu Phe Thr Ser Phe Trp
        195                 200                 205

Phe Asp Asp Arg Leu Ser Pro Arg Ser Cys Ala Asn Phe Pro Glu Gly
    210                 215                 220

His Ser Arg Ser Glu Phe Ser Phe Ser Thr Asp Leu Trp Asn His Ser
225                 230                 235                 240

Lys Glu Glu
```

<210> SEQ ID NO 2
<211> LENGTH: 290
<212> TYPE: PRT
<213> ORGANISM: Malus domestica

<400> SEQUENCE: 2

```
Met Gly Arg Ser Pro Cys Cys Ser Lys Glu Gly Leu Asn Arg Gly Ala
1               5                   10                  15

Trp Thr Ala Leu Glu Asp Lys Ile Leu Thr Ala Tyr Ile Lys Ala His
            20                  25                  30

Gly Glu Gly Lys Trp Arg Ser Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Gly Asp Glu Glu Leu Ile Val Arg
65                  70                  75                  80

Leu His Asn Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Thr Leu
            100                 105                 110

Gly Lys Lys Ser Lys Val Asp Ser Phe Ser Gly Ser Ser Lys Glu Thr
```

```
                  115                 120                 125
Ser Leu Asn Pro Cys Lys Ser Ile Ala Lys Lys Asp Val Glu Ser
    130                 135                 140
Lys Thr Ser Thr Ala Ala Ala Gln Pro Leu Val Ile Arg Thr Lys Ala
145                 150                 155                 160
Thr Arg Leu Thr Lys Ile Leu Val Pro Gln Asn Ile Pro Ser Asp Glu
                165                 170                 175
Asn Tyr Thr Ala Ala Ala Asn Pro Leu Glu Leu Gln Thr Gln Ser
                180                 185                 190
Ala Glu Lys Gly Gly Ser Thr Glu Glu Phe Pro Arg Thr Asn Ala Gly
            195                 200                 205
Asp Cys Ser Asn Ile Leu Lys Asn Phe Gly Cys Asp Asp Asp Ile
    210                 215                 220
Asp Ala Lys Gly Asp Gln Tyr Cys Asn Glu Phe Gln Leu Leu Asn Ser
225                 230                 235                 240
Ile Pro Leu Asp Glu Ala Met Ile Asn Asp Gly Cys Trp Thr Gly Gly
                245                 250                 255
Asn Gly Cys Asp Leu Glu Asp Tyr Gly Ala Ser Leu Asp Leu Asp Ser
            260                 265                 270
Leu Ala Phe Leu Leu Asp Ser Glu Glu Trp Pro Ser Gln Glu Asn Val
        275                 280                 285
Val Val
    290

<210> SEQ ID NO 3
<211> LENGTH: 709
<212> TYPE: PRT
<213> ORGANISM: Malus domestica

<400> SEQUENCE: 3

Met Ala Ala Pro Pro Ser Ser Ser Arg Leu Arg Gly Met Leu Gln
1               5                   10                  15
Ala Ser Val Gln Tyr Val Gln Trp Thr Tyr Ser Leu Phe Trp Gln Ile
            20                  25                  30
Cys Pro Gln Gln Gly Ile Leu Val Trp Ser Asp Gly Tyr Tyr Asn Gly
        35                  40                  45
Ala Ile Lys Thr Arg Lys Thr Val Gln Pro Met Glu Val Ser Ala Asp
    50                  55                  60
Glu Ala Ser Leu Gln Arg Ser Gln Gln Leu Arg Glu Leu Tyr Asp Ser
65                  70                  75                  80
Leu Ser Ala Gly Glu Thr Asn Gln Pro Pro Ala Arg Arg Pro Cys Ala
                85                  90                  95
Ser Leu Ser Pro Glu Asp Leu Thr Glu Ser Glu Trp Phe Tyr Leu Met
            100                 105                 110
Cys Val Ser Phe Ser Phe Pro Pro Gly Val Gly Leu Pro Gly Lys Ala
        115                 120                 125
Tyr Ala Arg Arg Gln His Val Trp Leu Thr Gly Ala Asn Glu Val Asp
    130                 135                 140
Ser Lys Thr Phe Ser Arg Ala Ile Leu Ala Lys Ser Ala Arg Ile Gln
145                 150                 155                 160
Thr Val Val Cys Ile Pro Leu Leu Asp Gly Val Val Glu Phe Gly Thr
                165                 170                 175
Thr Glu Arg Val Pro Glu Asp His Ala Phe Val Glu His Val Lys Thr
            180                 185                 190
Phe Phe Val Asp His His His Pro Pro Pro Lys Pro Ala Leu Ser
```

```
                195                 200                 205
Glu His Ser Thr Ser Asn Pro Ala Ala Ser Ser Asp His Pro His Phe
210                 215                 220
His Ser Pro His Leu Leu Gln Ala Met Cys Thr Asn Pro Pro Leu Asn
225                 230                 235                 240
Ala Ala Gln Glu Asp Glu Asp Glu Glu Asp Asp Asn Gln Glu
            245                 250                 255
Glu Asp Asp Gly Gly Ala Glu Ser Asp Ser Glu Ala Glu Thr Gly Arg
            260                 265                 270
Asn Gly Gly Ala Val Val Pro Ala Ala Asn Pro Pro Gln Val Leu Ala
            275                 280                 285
Ala Val Ala Glu Pro Ser Glu Leu Met Gln Leu Glu Met Ser Glu Asp
            290                 295                 300
Ile Arg Leu Gly Ser Pro Asp Asp Ala Ser Asn Asn Leu Asp Ser Asp
305                 310                 315                 320
Phe His Leu Leu Ala Val Ser Gln Ser Arg Asn Pro Ala Asp Gln Gln
                325                 330                 335
Arg Gln Ala Asp Ser Tyr Arg Ala Glu Ser Thr Arg Arg Pro Ser
            340                 345                 350
Val Gln Glu Pro Leu Ser Ser Gly Leu Gln Pro Pro His Thr Gly Pro
            355                 360                 365
Leu Ala Leu Glu Glu Leu Thr His Asp Asp Thr His Tyr Ser Glu
370                 375                 380
Thr Val Ser Thr Ile Leu Gln Gly Gln Val Thr Gln Leu Met Asp Ser
385                 390                 395                 400
Ser Ser Thr Asp Tyr Thr Ala Cys Leu Thr Gln Ser Ala Phe Ala Lys
                405                 410                 415
Trp Ser Ser Arg Val Asp His His Phe Leu Met Pro Val Glu Gly Thr
                420                 425                 430
Ser Gln Trp Leu Leu Lys Tyr Ile Leu Phe Ser Val Pro Phe Leu His
            435                 440                 445
Ser Lys Tyr Arg Asp Glu Asn Ser Pro Lys Phe Gln Glu Gly Glu Gly
450                 455                 460
Ser Thr Arg Leu Arg Lys Gly Thr Pro Gln Asp Glu Leu Ser Ala Asn
465                 470                 475                 480
His Val Leu Ala Glu Arg Arg Arg Glu Lys Leu Asn Glu Arg Phe
                485                 490                 495
Ile Ile Leu Arg Ser Leu Val Pro Phe Val Thr Lys Met Asp Lys Ala
            500                 505                 510
Ser Ile Leu Gly Asp Thr Ile Glu Tyr Val Lys Gln Leu Arg Asn Lys
            515                 520                 525
Ile Gln Asp Leu Glu Ala Arg Asn Met Leu Val Glu Glu Asp Gln Arg
            530                 535                 540
Ser Arg Ser Ser Gly Glu Met Gln Arg Ser Asn Ser Cys Lys Glu Leu
545                 550                 555                 560
Arg Ser Gly Leu Thr Leu Val Glu Arg Thr Gln Gly Gly Pro Pro Gly
                565                 570                 575
Ser Asp Lys Arg Lys Leu Arg Ile Val Glu Gly Ser Gly Val Ala
            580                 585                 590
Ile Gly Lys Ala Lys Val Met Glu Asp Ser Pro Ser Pro Pro
            595                 600                 605
Pro Pro Pro Gln Pro Glu Pro Leu Pro Thr Pro Met Val Thr Gly Thr
610                 615                 620
```

```
Ser Leu Glu Val Ser Ile Ile Glu Ser Asp Gly Leu Glu Leu Gln
625                 630                 635                 640

Cys Pro Tyr Arg Glu Gly Leu Leu Leu Asp Val Met Arg Thr Leu Arg
            645                 650                 655

Glu Leu Arg Ile Glu Thr Thr Val Val Gln Ser Ser Leu Asn Asn Gly
                660                 665                 670

Phe Phe Val Ala Glu Leu Arg Ala Lys Val Lys Asp Asn Val Ser Gly
            675                 680                 685

Lys Lys Val Ser Ile Thr Glu Val Lys Arg Val Ile Asn Gln Ile Ile
690                 695                 700

Pro Gln Ser Asp Ser
705

<210> SEQ ID NO 4
<211> LENGTH: 651
<212> TYPE: PRT
<213> ORGANISM: Malus domestica

<400> SEQUENCE: 4

Met Ala Gln Asn His Glu Arg Val Pro Gly Asn Leu Arg Lys Gln Phe
1               5                   10                  15

Ala Val Ala Val Arg Ser Ile Lys Trp Ser Tyr Ala Ile Phe Trp Ser
            20                  25                  30

Leu Ser Thr Thr Gln Gln Gly Val Leu Glu Trp Gly Glu Gly Tyr Tyr
        35                  40                  45

Asn Gly Asp Ile Lys Thr Arg Lys Lys Val Glu Gly Val Glu Leu Lys
    50                  55                  60

Thr Asp Lys Met Gly Leu Gln Arg Asn Val Gln Leu Arg Glu Leu Tyr
65                  70                  75                  80

Lys Ser Leu Leu Glu Gly Glu Thr Glu Thr Glu Gln Gln Ala Lys Ala
                85                  90                  95

Pro Ser Ala Val Leu Ser Pro Glu Asp Leu Thr Asp Ala Glu Trp Tyr
            100                 105                 110

Tyr Leu Leu Cys Met Ser Phe Ile Phe Asn Pro Gly Glu Gly Leu Pro
        115                 120                 125

Gly Arg Ala Leu Ala Thr Gly Gln Thr Ile Trp Leu Cys Asn Ala Gln
    130                 135                 140

His Thr Asp Ser Lys Val Phe Ser Arg Ser Leu Leu Ala Lys Ser Ala
145                 150                 155                 160

Ser Val Gln Thr Val Cys Phe Pro Tyr Leu Gly Gly Val Val Glu
                165                 170                 175

Leu Gly Val Thr Glu Leu Val Ser Glu Asp Leu Asn Leu Ile Gln His
            180                 185                 190

Ile Lys Ala Ser Leu Leu Asp Phe Ser Lys Pro Asp Cys Cys Glu Lys
        195                 200                 205

Ser Ser Ser Ala Pro His Lys Pro Asp Asp Ser Glu Gln Ile Val
    210                 215                 220

Ala Lys Val Asp His Asp Val Val Asp Thr Leu Pro Leu Glu Asn Leu
225                 230                 235                 240

Tyr Ser Pro Ser Glu Glu Ile Lys Phe Asp Gln Arg Gly Ile Asn Gly
                245                 250                 255

Leu Leu Gly Asn His Glu Glu Val Asn Met Asp Ser Ser Asp Glu Cys
            260                 265                 270

Ser Asn Gly Cys Asp His Asn His Pro Thr Glu Asp Ser Met Met Leu
        275                 280                 285
```

```
Glu Gly Thr Asn Ala Val Ala Ser Gln Val Gln Ser Trp His Phe Met
    290             295                 300

Asp Glu Asp Phe Ser Ser Gly Val Gln Asp Ser Met Asn Ser Ser Asp
305                 310                 315                 320

Ser Ile Ser Glu Ala Phe Val Asn Gln Gly Lys Ala His Ser Phe Ala
                325                 330                 335

Lys His Glu Asn Ala Asn His Ile His Leu Lys Glu Leu Gln Asn Phe
                340                 345                 350

Asn Asp Thr Lys Leu Ser Ser Leu Tyr Leu Gly Ser Val Asp Glu His
                355                 360                 365

Val His Tyr Lys Arg Thr Leu Cys Thr Leu Leu Gly Ser Ser Met Lys
    370                 375                 380

Leu Ile Glu Asn Pro Cys Phe Cys Asp Gly Glu Ser Lys Ser Ser Phe
385                 390                 395                 400

Val Lys Trp Lys Lys Glu Val Val Gly Ser Cys Arg Pro Thr Val His
                405                 410                 415

Gln Lys Thr Leu Lys Lys Ile Leu Phe Thr Val Pro Leu Met Tyr Gly
                420                 425                 430

Val His Ser Pro Met Ala Thr Gly Lys Glu Asn Thr Gly Lys Asp Leu
    435                 440                 445

Leu Pro Asn Leu Gln Gly Asp Asp Ile Asn Arg Glu His Asp Lys Met
450                 455                 460

Arg Glu Asn Ala Lys Leu Leu Val Leu Arg Ser Met Val Pro Ser Ile
465                 470                 475                 480

Thr Glu Val Asp Lys Ala Ser Ile Leu Asp Thr Ile Lys Tyr Leu
                485                 490                 495

Lys Glu Leu Glu Ala Arg Ala Glu Glu Met Glu Ser Cys Met Asp Thr
                500                 505                 510

Val Glu Ala Ile Ser Arg Gly Lys Phe Leu Asn Arg Val Glu Lys Thr
    515                 520                 525

Ser Asp Asn Tyr Asp Lys Thr Lys Lys Asn Asn Val Lys Lys Ser Leu
530                 535                 540

Val Lys Lys Arg Lys Ala Cys Asp Ile Asp Glu Thr Asp Pro Tyr Pro
545                 550                 555                 560

Asn Met Leu Val Ser Gly Glu Ser Leu Pro Leu Asp Val Lys Val Cys
                565                 570                 575

Val Lys Glu Gln Glu Val Leu Ile Glu Met Arg Cys Pro Tyr Arg Glu
                580                 585                 590

Tyr Ile Leu Leu Asp Ile Met Asp Ala Ile Asn Asn Leu Tyr Leu Asp
    595                 600                 605

Ala His Ser Val Gln Ser Ser Ile Leu Asp Gly Val Leu Thr Leu Ser
610                 615                 620

Leu Lys Ser Lys Phe Arg Gly Ala Ala Ile Ser Pro Val Gly Met Ile
625                 630                 635                 640

Lys Gln Val Leu Trp Lys Ile Ala Gly Lys Cys
                645                 650

<210> SEQ ID NO 5
<211> LENGTH: 729
<212> TYPE: DNA
<213> ORGANISM: Malus domestica

<400> SEQUENCE: 5 atggaggat ataacgaaaa cctgagtgtg agaaaaggtg cctggactcg agaggaagac    60
aatcttctca ggcagtgcgt tgagattcat ggagagggaa agtggaacca agtttcatac   120
```

-continued

```
aaagcaggct taaacaggtg caggaaaagt tgcagactta gatggttgaa ttatttgaag    180
ccaaatatca agagaggaga cttaaagag gatgaagtag atcttataat tagacttcac    240
aggcttttgg gaaacaggtg gtcattgatt gctagaagac ttccaggaag aacagcaaat    300
gctgtgaaaa attattggaa cactcgattg cggatcgatt ctcgcatgaa aacggtgaaa    360
aataaatctc aagaaatgag agagaccaat gtgataagac ctcagccccca aaaattcaac    420 agaagttcat attacttaag cagtaaagaa ccaattctag accatattca atcagcagaa    480
gatttaagta cgccaccaca aacgtcgtcg tcaacaaaga atggaaatga ttggtgggag    540
accttgttag aaggtgagga tacttttgaa agagctgcat atcccagcat tgagttagag    600
gaagaactct tcacaagttt ttggtttgat gatcgactgt cgccaagatc atgcgccaat    660
tttcctgaag acatagtag aagtgaattc tcctttagca cggacctttg aatcattca     720 aaagaagaa                                                           729
```

<210> SEQ ID NO 6
<211> LENGTH: 870
<212> TYPE: DNA
<213> ORGANISM: Malus domestica

<400> SEQUENCE: 6

```
atggggagga gtccgtgttg ctccaaggaa ggactcaaca gaggagcctg gactgccttg     60
gaagataaaa tttatcatc ttacatcaaa gctcatggag aaggaaaatg gagaagcctc    120
cctaaaagag ctggtctgaa gagatgtggt aaaagttgta gacttagatg gttaaactat    180
ctgagaccag acataaagag aggcaacatt tcaggtgatg aagaagaact cattgtcagg    240
ctccataacc ttcttggtaa cagatggtcc ttaatagccg gaaggctacc ggggcgaaca    300
gacaatgaaa tcaagaatta ctggaataca actttgggga agaaatcgaa agtcgattcg    360
ttttctggat cctcgaaaga aacttctcta aatccatgca atccatagc gaaaagaaa    420 gatgtcgagt ccaaaacatc aactgccgct gctcaacctc tagtaataag aaccaaggcc    480
actaggttga ccaaaatttt agtcccacaa aatattccta gtgacgaaaa ttatacagca    540
gctgccgcaa acccattaga gcttcagacc caatcggcgg aaaaaggcgg aagcaccgaa    600
gagtttccga ggactaatgc aggtgactgc agcaacatct tgaagaactt tggctgcgat    660
gatgacgaca ttgatgcgaa gggagatcaa tactgcaacg agtttcagtt gctcaactct    720
ataccgttgg atgaggcaat gataaatgac ggctgctgga cggaggaaa cggttgcgat    780 ctggaggact acggtgcctc gttggattta gattctttgg cattcttgct tgactctgag    840
gaatggcctt cccaagaaaa tgttgtagtc                                    870
```

<210> SEQ ID NO 7
<211> LENGTH: 2130
<212> TYPE: DNA
<213> ORGANISM: Malus domestica

<400> SEQUENCE: 7

```
atggctgcac cgccgccaag cagcagccgc ctccgcggta tgttgcaggc ctcagttcaa     60
tatgtccaat ggacttacag tctcttctgg caaatctgtc cccaacaagg gatcttagta    120
tggtcagatg ggtactataa tggagctatc aagacgagga agacagtgca accaatggaa    180
gtgagtgccg atgaggcatc tctccagagg agccagcaac tcagagaact ctacgactct    240
ttgtccgctg agagacaaa ccagccccca gcacgccgcc cttgcgcttc cttgtcccccg    300 gaggacttaa ccgaatctga atggttctac ttgatgtgcg tctcattctc ctttcccccc    360
```

-continued

```
ggcgtcgggt tgccagggaa agcatacgca aggaggcagc atgtatggct caccggtgca    420
aacgaggtcg atagcaaaac cttttccaga gctattttgg caaagagtgc tcgtatacag    480
accgtggtgt gcattcctct tctagatggc gtcgtagaat ttggcaccac agagagggtt    540
ccagaagacc acgccttcgt cgaacacgtc aaaaccttct tcgttgacca ccaccaccct    600
ccgccaccaa aacccgccct ctccgagcac tccacatcca accccgccgc ctcatccgat    660
cacccacatt tccactctcc gccttctc caggccatgt gcaccaaccc tcctctcaac      720
gccgcccaag aagacgaaga ggacgaagaa gaagatgata atcaggagga ggacgacgga    780
ggagccgagt ccgactccga agccgaaacg ggccgcaatg gtggagccgt tgttcccgcc    840
gcaaaccctc ctcaggtttt ggccgcggta gccgagccaa gcgagctcat gcaactcgag    900
atgtccgaag acatccggct aggctccccg gacgatgcct caaataactt ggactctgat    960
ttccacttgt tagctgtgag tcagtctagg aacccagcgg atcagcagag acaagctgac   1020
tcgtatcgag ccgagtcgac caggcggcgt ccgtcagtac aagagccgct gagcagtggc   1080
cttcaaccgc cgcacacagg accctagct ttagaggagt tgacacatga tgacgacaca    1140
cattactcgg agacagtctc caccatactg cagggacagg tgactcagtt gatggattca   1200
tcgtccaccg actacacagc ttgcttgact caatcagctt tcgccaagtg gtcgagccgg   1260
gttgatcacc acttcctcat gccggttgaa ggcacgtccc aatggctctt gaaatatatt   1320
ttgtttagtg taccgttcct ccactcaaaa tatcgcgacg agaactcgcc aaaatttcag   1380
gagggcgaag gctcgacacg gttgaggaaa gggaccccac aagacgagct cagtgctaat   1440
catgtgttag cggaacgacg tcgtagagag aagcttaatg agaggtttat tatactaagg   1500
tccctggtgc cttttgtgac aaaaatggac aaggcttcga tattaggaga cacaatcgag   1560
tatgtaaagc aactgcgtaa caaaattcag gatctcgagg cacgtaacat gctggtggag   1620
gaagatcaac ggtcaagatc atccggggaa atgcaaaggt ccaatagttg taaagagttg   1680
cgaagtgggc tcacgctagt ggagcggacc caaggaggtc cacccgggtc cgataaaagg   1740
aagttgagga ttgtggaggg aagtggcggt gtcgccattg gtaaggctaa agtaatggag   1800
gactcaccgc cttcaccacc cccgccacca cctcagccag aacctttacc gacacctatg   1860
gtgacgggga cttctctaga ggtgtcgata atcgagagtg atgggttgtt ggagctccag   1920
tgcccgtata gagaagggtt attgcttgat gtgatgcgaa cacttaggga gctaagaatt   1980
gagaccacgg tggtccagtc ctcattgaat aacggatttt tcgtagctga actaagagcc   2040
aaggtgaagg ataacgtcag tggcaagaaa gtaagtataa cggaagtgaa gagggtgata   2100
aatcaaatta taccccaatc tgactcttaa                                    2130
```

<210> SEQ ID NO 8
<211> LENGTH: 2457
<212> TYPE: DNA
<213> ORGANISM: Malus domestica
<220> FEATURE:
<221> NAME/KEY: misc_feature
<222> LOCATION: (1326)..(1326)
<223> OTHER INFORMATION: n is a, c, g, or t

<400> SEQUENCE: 8

```
gagaacctat attcccttc ggaagaaatc aaatttgatc agaggggaat taatggttta     60
ctcggaaacc atgaagaggt caacatggac tcttctgatg aatgttctaa tggttgtgat   120
cacaatcatc cgacagaaga ctccatgatg cttgaaggta ccaatgctgt ggcttctcag   180
gttcagagtt ggcatttcat ggatgaagac ttcagcagtg gcgttcaaga ttccatgaat   240
```

```
tctagtgact ccatatctga agcttttgtt aatcaaggaa aggctcactc ttttgctaaa      300
cacgagaatg cgaaccatat ccatttaaag gaacttcaaa acttcaatga cacaaaacta      360
agttctttgt atcttggatc tgttgatgaa catgtacact acaaaagaac tctttgtact      420
cttctaggaa gctcaatgaa gctgattgaa atccatgtt tttgcgacgg agagagcaaa       480
tccagttttg tgaaatggaa gaaagaagtt gttggtagtt gtaggccaac agtacatcag      540
aagacattaa agaagatttt gttcactgtt cctttaatgt atggtgttca ctcgcctatg      600
gcaaccggta agaaaaatac gggaaaagat ttgctcccaa atttgcaagg tgacgatatt      660
aacagggaac atgataaaat gagagagaac gcaaaattgt tggtcctcag gtcaatggtt      720
ccttctatca ctgaggttga taaagcttcg atccttgatg tacgatcaa gtacttgaaa       780
gagcttgagg cacgagcaga agagatgaa tcctgcatgg acaccgtgga agctatttct       840
agagggaaat tcctgaacag ggtagagaag acatcagata actatgataa aacaaagaag      900
aacaatgtga aaaagtcttt agtaaagaag agaaaggcct gtgacattga cgaaactgac      960
ccatatccca atatgcttgt ttccggagaa agcttgccac tagatgtgaa agtgtgtgta     1020
aaagagcaag aggttctgat agagatgaga tgcccttacc gggaatatat cttgcttgat     1080
ataatggatg ccattaacaa tctgtactta gatgcacatt cggtccaatc atccatcctt     1140
gacggtgttc tcacattgag ccttaaatca aagtttcgag gagcggcgat ttcaccagtg     1200
gggatgatta agcaggtgct ttggaaaatt gctggtaagt gctgagaagc cggacaaagc     1260
taatgttgta gttgtaggat ttctacgcag gaagagtaat gtagctgctt gatgaaaaaa     1320
aaaaantctg cagcagtaac tggggcagtt tgatctggtt cgtaacatgc attccccagt     1380
tttactgttt aaccttgtca ttggataata agcttcagta gtagtaactt tgttcatgtg     1440
aatgtgatgg acaaatggaa catccaaatt ccaatataac ttgtctcgta tcgtatgtga     1500
ttttaatata aaaaaaaaaa agctggattt ctggtctcca aagaactgta aaatatatgc     1560
ctgcacttca ctgaaatccc cctcaaaact ctgatataaa tcatgggttt tctgcagaaa     1620
tcactaatag cattcagctg aaaccaaaat ccaagaaaaa acccaaattt tcatgttttt     1680
tcttggctgt tgagcttggt gggggttttt tttacttgtg taagttgaat tatatttgtg     1740
gggaaaatgg ctcagaatca tgagagggtg ccggggaatc tgagaaaaca gtttgctgtt     1800
gctgtgagga gtattaagtg gagctatgca attttctggt cattgtcaac tacacaacaa     1860
ggagtgctgg aatggggtga ggggtactac aatggagaca tcaaaacccg aaaaaaagtt     1920
gaaggtgtgg aacttaaaac cgataaaatg ggtttacaga ggaatgtgca actcagagag     1980
ctgtataagt ctcttctgga aggtgagact gagactgagc agcaagctaa agcgccttct     2040
gctgtattgt ccccggaaga tctcacagat gccgagtggt attacttgct ttgcatgtcc     2100
ttcatattca atcctggcga aggtttgcca ggaagagcat tggcaactgg ccaaaccatt     2160
tggttgtgca atgctcaaca tacgatagt aaagttttct cgcgctcttt gctggcgaag      2220
agtgcatctg ttcagactgt agtctgcttt ccctacctgg ggggtgttgt tgagctaggt     2280
gtgactgagc tggtatcgga ggaccttaat ctcattcaac acatcaaggc ttccttacta     2340
gatttttcaa agcctgattg ctgtgagaaa tcttcctctg cccctcacaa accagacgat     2400
gattcagagc aaatagttgc caaggttgac catgacgtag ttgatacatt gcccttta      2457
```

<210> SEQ ID NO 9
<211> LENGTH: 243
<212> TYPE: PRT
<213> ORGANISM: Malus sylvestris

```
<400> SEQUENCE: 9

Met Glu Gly Tyr Asn Glu Asn Leu Ser Val Arg Lys Gly Ala Trp Thr
1               5                   10                  15

Arg Glu Glu Asp Asn Leu Leu Arg Gln Cys Val Glu Ile His Gly Glu
                20                  25                  30

Gly Lys Trp Asn Gln Val Ser Tyr Lys Ala Gly Leu Asn Arg Cys Arg
            35                  40                  45

Lys Ser Cys Arg Gln Arg Trp Leu Asn Tyr Leu Lys Pro Asn Ile Lys
50                  55                  60

Arg Gly Asp Phe Lys Glu Asp Glu Val Asp Leu Ile Ile Arg Leu His
65                  70                  75                  80

Arg Leu Leu Gly Asn Arg Trp Ser Leu Ile Ala Arg Arg Leu Pro Gly
                85                  90                  95

Arg Thr Ala Asn Ala Val Lys Asn Tyr Trp Asn Thr Arg Leu Arg Ile
                100                 105                 110

Asp Ser Arg Met Lys Thr Val Lys Asn Lys Ser Gln Glu Met Arg Lys
                115                 120                 125

Thr Asn Val Ile Arg Pro Gln Pro Gln Lys Phe Asn Arg Ser Ser Tyr
130                 135                 140

Tyr Leu Ser Ser Lys Glu Pro Ile Leu Asp His Ile Gln Ser Ala Glu
145                 150                 155                 160

Asp Leu Ser Thr Pro Pro Gln Thr Ser Ser Thr Lys Asn Gly Asn
                165                 170                 175

Asp Trp Trp Glu Thr Leu Leu Glu Gly Glu Asp Thr Phe Glu Arg Ala
                180                 185                 190

Ala Tyr Pro Ser Ile Glu Leu Glu Glu Leu Phe Thr Ser Phe Trp
                195                 200                 205

Phe Asp Asp Arg Leu Ser Pro Arg Ser Cys Ala Asn Phe Pro Glu Gly
210                 215                 220

Gln Ser Arg Ser Glu Phe Ser Phe Ser Thr Asp Leu Trp Asn His Ser
225                 230                 235                 240

Lys Glu Glu

<210> SEQ ID NO 10
<211> LENGTH: 244
<212> TYPE: PRT
<213> ORGANISM: Pyrus communis

<400> SEQUENCE: 10

Met Glu Gly Tyr Asn Val Asn Leu Ser Val Arg Lys Gly Ala Trp Thr
1               5                   10                  15

Arg Glu Glu Asp Asn Leu Leu Arg Gln Cys Ile Glu Ile His Gly Glu
                20                  25                  30

Gly Lys Trp Asn Gln Val Ser Tyr Lys Ala Gly Leu Asn Arg Cys Arg
            35                  40                  45

Lys Ser Cys Arg Gln Arg Trp Leu Asn Tyr Leu Lys Pro Asn Ile Lys
50                  55                  60

Arg Gly Asp Phe Lys Glu Asp Glu Val Asp Leu Ile Leu Arg Leu His
65                  70                  75                  80

Arg Leu Leu Gly Asn Arg Trp Ser Leu Ile Ala Arg Arg Leu Pro Gly
                85                  90                  95

Arg Thr Ala Asn Asp Val Lys Asn Tyr Trp Tyr Thr Arg Leu Arg Ile
                100                 105                 110

Asp Ser Arg Met Lys Thr Val Lys Asn Lys Ser Gln Glu Thr Arg Lys
```

```
                  115                 120                 125
Thr Asn Val Ile Arg Pro Gln Pro Gln Lys Phe Ile Lys Ser Ser Tyr
130                 135                 140

Tyr Leu Ser Ser Lys Glu Pro Ile Leu Glu His Ile Gln Ser Ala Glu
145                 150                 155                 160

Asp Leu Ser Thr Pro Ser Gln Thr Ser Ser Thr Lys Asn Gly Asn
                165                 170                 175

Asp Trp Trp Glu Thr Leu Phe Glu Gly Glu Asp Thr Phe Glu Arg Ala
                180                 185                 190

Ala Cys Pro Ser Ile Glu Leu Glu Glu Leu Phe Thr Ser Phe Trp
                195                 200                 205

Phe Asp Asp Arg Leu Ser Ala Arg Ser Cys Ala Asn Phe Pro Glu Glu
                210                 215                 220

Gly Gln Ser Arg Ser Glu Phe Ser Phe Ser Met Asp Leu Trp Asn His
225                 230                 235                 240

Ser Lys Glu Glu

<210> SEQ ID NO 11
<211> LENGTH: 244
<212> TYPE: PRT
<213> ORGANISM: Pyrus pyrifolia

<400> SEQUENCE: 11

Met Glu Gly Tyr Asn Val Asn Leu Ser Val Arg Lys Gly Ala Trp Thr
1               5                   10                  15

Arg Glu Glu Asp Asn Leu Leu Arg Gln Cys Ile Glu Ile His Gly Glu
                20                  25                  30

Gly Lys Trp Asn Gln Val Ser Tyr Lys Ala Gly Leu Asn Arg Cys Arg
            35                  40                  45

Lys Ser Cys Arg Gln Arg Trp Leu Asn Tyr Leu Lys Pro Asn Ile Lys
50                  55                  60

Arg Gly Asp Phe Lys Glu Asp Glu Val Asp Leu Ile Leu Arg Leu His
65                  70                  75                  80

Arg Leu Leu Gly Asn Arg Trp Ser Leu Ile Ala Arg Arg Leu Pro Gly
                85                  90                  95

Arg Thr Ala Asn Asp Val Lys Asn Tyr Trp Asn Thr Arg Leu Gly Ile
                100                 105                 110

Asp Ser Arg Met Lys Thr Leu Lys Asn Lys Ser Gln Glu Thr Arg Lys
                115                 120                 125

Thr Asn Val Ile Arg Pro Gln Pro Gln Lys Phe Ile Lys Ser Ser Tyr
130                 135                 140

Tyr Leu Ser Ser Lys Glu Pro Ile Leu Glu His Ile Gln Ser Ala Glu
145                 150                 155                 160

Asp Leu Ser Thr Pro Ser Gln Thr Ser Ser Thr Lys Asn Gly Asn
                165                 170                 175

Asp Trp Trp Glu Thr Leu Phe Glu Gly Glu Asp Thr Phe Glu Arg Ala
                180                 185                 190

Ala Cys Pro Ser Ile Glu Leu Glu Glu Leu Phe Thr Thr Phe Trp
                195                 200                 205

Phe Asp Asp Arg Leu Ser Ala Arg Ser Cys Ala Asn Phe Pro Glu Glu
                210                 215                 220

Gly Gln Ser Arg Ser Glu Phe Ser Phe Ser Met Asp Leu Trp Asn His
225                 230                 235                 240

Ser Lys Glu Glu
```

```
<210> SEQ ID NO 12
<211> LENGTH: 244
<212> TYPE: PRT
<213> ORGANISM: Pyrus bretschneideri

<400> SEQUENCE: 12
```

Met Glu Gly Tyr Asn Val Asn Leu Ser Val Arg Lys Gly Ala Trp Thr
1               5                   10                  15

Arg Glu Glu Asp Asn Leu Leu Arg Gln Cys Ile Glu Ile His Gly Glu
            20                  25                  30

Gly Lys Trp Asn Gln Val Ser Tyr Lys Ala Gly Leu Asn Arg Cys Arg
        35                  40                  45

Lys Ser Cys Arg Gln Arg Trp Leu Asn Tyr Leu Lys Pro Asn Ile Lys
50                  55                  60

Arg Gly Asp Phe Lys Glu Asp Glu Val Asp Leu Ile Leu Arg Leu His
65                  70                  75                  80

Arg Leu Leu Gly Asn Arg Trp Ser Leu Ile Ala Arg Arg Leu Pro Gly
                85                  90                  95

Arg Thr Ala Asn Asp Val Lys Asn Tyr Trp Asn Thr Arg Leu Gly Ile
            100                 105                 110

Asp Ser Arg Met Lys Thr Leu Lys Asn Lys Ser Gln Glu Thr Arg Lys
        115                 120                 125

Thr Asn Val Ile Arg Pro Gln Pro Gln Lys Phe Ile Lys Ser Ser Tyr
130                 135                 140

Tyr Leu Ser Ser Lys Glu Pro Ile Leu Glu His Ile Gln Ser Ala Glu
145                 150                 155                 160

Asp Leu Ser Thr Pro Ser Gln Thr Ser Ser Thr Lys Asn Gly Asn
                165                 170                 175

Asp Trp Trp Glu Thr Leu Phe Glu Gly Glu Asp Thr Phe Glu Arg Ala
            180                 185                 190

Ala Cys Pro Ser Ile Glu Leu Glu Glu Leu Phe Thr Thr Phe Trp
        195                 200                 205

Phe Asp Asp Arg Leu Ser Ala Arg Ser Cys Ala Asn Phe Pro Glu Glu
    210                 215                 220

Gly Gln Ser Arg Ser Glu Phe Ser Phe Ser Met Asp Leu Trp Asn His
225                 230                 235                 240

Ser Lys Glu Glu

```
<210> SEQ ID NO 13
<211> LENGTH: 245
<212> TYPE: PRT
<213> ORGANISM: Cydonia oblonga

<400> SEQUENCE: 13
```

Met Glu Gly Tyr Asn Val Asn Leu Ser Val Met Arg Lys Gly Ala Trp
1               5                   10                  15

Thr Arg Glu Glu Asp Asp Leu Leu Arg Gln Cys Ile Gly Ile Leu Gly
            20                  25                  30

Glu Gly Lys Trp His Gln Val Pro Tyr Lys Thr Gly Leu Asn Arg Cys
        35                  40                  45

Arg Lys Ser Cys Arg Leu Arg Trp Leu Asn Tyr Leu Lys Pro Asn Ile
50                  55                  60

Lys Arg Gly Asp Phe Thr Glu Asp Glu Val Asp Leu Ile Ile Arg Leu
65                  70                  75                  80

His Lys Leu Leu Gly Asn Arg Trp Ser Leu Ile Ala Gly Arg Leu Pro
                85                  90                  95

-continued

```
Gly Arg Thr Ala Asn Asp Val Lys Asn Tyr Trp Asn Thr Arg Leu Arg
                100                 105                 110

Ile Asn Ser Arg Met Lys Thr Leu Lys Asn Lys Ser Gln Glu Thr Arg
            115                 120                 125

Lys Thr Asn Val Ile Arg Pro Gln Pro Arg Lys Phe Ile Lys Ser Ser
        130                 135                 140

Tyr Tyr Leu Ser Ser Lys Gly Pro Ile Leu Asp His Ile Gln Ser Ala
145                 150                 155                 160

Glu Asp Leu Ser Thr Pro Pro Gln Thr Ser Ser Thr Lys Asn Gly
                165                 170                 175

Asn Asp Trp Trp Glu Thr Leu Phe Glu Gly Asp Thr Phe Glu Arg
                180                 185                 190

Ala Ala Cys Pro Ser Ile Glu Leu Glu Glu Leu Phe Thr Ser Phe
                195                 200                 205

Trp Phe Asp Asp Arg Leu Ser Ala Arg Ser Cys Ala Asn Phe Pro Glu
            210                 215                 220

Glu Gly Gln Ser Arg Ser Glu Phe Ser Val Ser Met Asp Leu Trp Asn
225                 230                 235                 240

His Ser Lys Glu Glu
                245

<210> SEQ ID NO 14
<211> LENGTH: 243
<212> TYPE: PRT
<213> ORGANISM: Prunus salicina

<400> SEQUENCE: 14

Met Glu Gly Tyr Asn Leu Gly Val Arg Lys Gly Ala Trp Thr Arg Lys
1               5                   10                  15

Glu Asp Asp Leu Leu Arg Gln Cys Ile Glu Lys His Gly Glu Gly Lys
                20                  25                  30

Trp His Gln Val Pro Tyr Lys Ala Gly Leu Ser Arg Cys Arg Lys Ser
            35                  40                  45

Cys Arg Leu Arg Trp Leu Asn Tyr Leu Lys Pro Asn Ile Lys Arg Gly
        50                  55                  60

Asp Phe Met Glu Asp Glu Val Asp Leu Ile Ile Arg Leu His Lys Leu
65                  70                  75                  80

Leu Gly Asn Arg Trp Ser Leu Ile Ala Arg Arg Leu Pro Gly Arg Thr
                85                  90                  95

Ala Asn Asp Val Lys Asn Tyr Trp Asn Thr Arg Leu Arg Thr Asp Tyr
                100                 105                 110

Cys Met Lys Lys Met Lys Asp Lys Ser Gln Glu Thr Ile Lys Thr Ile
            115                 120                 125

Ile Arg Pro Gln Pro Arg Arg Phe Thr Lys Ser Ser Asn Cys Leu Ser
        130                 135                 140

Phe Lys Glu Pro Ile Leu Asp His Thr Gln Leu Glu Glu Asn Phe Ser
145                 150                 155                 160

Thr Thr Ser Gln Ile Ser Thr Ser Thr Arg Ile Gly Ser Asp Trp Trp
                165                 170                 175

Glu Thr Phe Leu Asp Asp Lys Asp Ala Thr Glu Thr Ala Thr Gly Ser
                180                 185                 190

Gly Leu Gly Leu Asp Glu Glu Leu Leu Ala Ser Phe Trp Val Asp Asp
            195                 200                 205

Asp Met Pro Gln Ser Thr Arg Thr Cys Val Asn Phe Ser Glu Glu Gly
        210                 215                 220
```

```
Leu Ser Arg Gly Asp Phe Ser Phe Ser Val Asp Leu Trp Asn His Ser
225                 230                 235                 240

Lys Glu Glu
```

<210> SEQ ID NO 15
<211> LENGTH: 243
<212> TYPE: PRT
<213> ORGANISM: Prunus cerasifera

<400> SEQUENCE: 15

```
Met Glu Gly Tyr Asn Leu Gly Val Arg Lys Gly Ala Trp Thr Arg Lys
1               5                   10                  15

Glu Asp Asp Leu Leu Arg Gln Cys Ile Glu Lys His Gly Glu Gly Lys
            20                  25                  30

Trp His Gln Val Pro Tyr Lys Ala Gly Leu Ser Arg Cys Arg Arg Ser
        35                  40                  45

Cys Arg Leu Arg Trp Leu Asn Tyr Leu Lys Pro Asn Ile Lys Arg Gly
50                  55                  60

Asp Phe Met Glu Asp Glu Val Asp Leu Ile Ile Arg Leu His Lys Leu
65                  70                  75                  80

Leu Gly Asn Arg Trp Ser Leu Ile Ala Arg Arg Leu Pro Gly Arg Thr
                85                  90                  95

Ala Asn Asp Val Lys Asn Tyr Trp Asn Thr Arg Leu Arg Lys Asp Tyr
            100                 105                 110

Cys Met Lys Lys Met Lys Asp Lys Ser Gln Glu Thr Ile Lys Thr Ile
        115                 120                 125

Ile Arg Pro Gln Pro Arg Ser Phe Thr Lys Ser Ser Asn Cys Leu Ser
130                 135                 140

Phe Lys Glu Pro Ile Leu Asp His Thr Gln Leu Glu Glu Asn Phe Ser
145                 150                 155                 160

Thr Pro Ser Gln Thr Ser Thr Ser Thr Arg Ile Gly Ser Asp Trp Trp
                165                 170                 175

Glu Thr Phe Leu Asp Asp Lys Asp Ala Thr Glu Arg Asp Thr Gly Ser
            180                 185                 190

Gly Leu Gly Leu Asp Glu Glu Leu Leu Ala Ser Phe Trp Val Asp Asp
        195                 200                 205

Asp Met Pro Gln Ser Thr Arg Thr Cys Val Asn Phe Ser Glu Glu Gly
210                 215                 220

Leu Ser Arg Gly Asp Phe Ser Phe Ser Val Asp Leu Trp Asn His Ser
225                 230                 235                 240

Lys Glu Glu
```

<210> SEQ ID NO 16
<211> LENGTH: 243
<212> TYPE: PRT
<213> ORGANISM: Prunus persica

<400> SEQUENCE: 16

```
Met Glu Gly Tyr Asn Leu Gly Val Arg Lys Gly Ala Trp Thr Arg Glu
1               5                   10                  15

Glu Asp Asp Leu Leu Arg Gln Cys Ile Glu Asn His Gly Glu Gly Lys
            20                  25                  30

Trp His Gln Val Pro Asn Lys Ala Gly Leu Asn Arg Cys Arg Lys Ser
        35                  40                  45

Cys Arg Leu Arg Trp Met Asn Tyr Leu Lys Pro Asn Ile Lys Arg Gly
50                  55                  60
```

Glu Phe Ala Glu Asp Glu Val Asp Leu Ile Ile Arg Leu His Lys Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr Arg Leu Arg Thr Asp Ser
            100                 105                 110

Arg Leu Lys Lys Val Lys Asp Lys Pro Gln Glu Thr Ile Lys Thr Ile
        115                 120                 125

Val Ile Arg Pro Gln Pro Arg Ser Phe Ile Lys Ser Ser Asn Cys Leu
130                 135                 140

Ser Ser Lys Glu Pro Ile Leu Asp His Ile Gln Thr Val Glu Asn Phe
145                 150                 155                 160

Ser Thr Pro Ser Gln Thr Ser Pro Ser Thr Lys Asn Gly Asn Asp Trp
                165                 170                 175

Trp Glu Thr Phe Leu Asp Asp Glu Asp Val Phe Glu Arg Ala Thr Cys
            180                 185                 190

Tyr Gly Leu Ala Leu Glu Glu Glu Phe Thr Ser Phe Trp Val Asp
        195                 200                 205

Asp Met Pro Gln Ser Lys Arg Gln Cys Thr Asn Val Ser Glu Glu Gly
210                 215                 220

Leu Gly Arg Gly Asp Phe Ser Phe Ser Val Asp Leu Trp Asn His Ser
225                 230                 235                 240

Lys Glu Glu

<210> SEQ ID NO 17
<211> LENGTH: 246
<212> TYPE: PRT
<213> ORGANISM: Eriobotrya japonica

<400> SEQUENCE: 17

Met Glu Gly Tyr Asn Val Asn Leu Arg Val Lys Arg Lys Gly Ala Trp
1               5                   10                  15

Thr Arg Glu Glu Asp Asn Leu Leu Arg Gln Cys Ile Glu Ile Leu Gly
            20                  25                  30

Glu Gly Lys Trp His Gln Val Pro Tyr Lys Ala Gly Leu Asn Arg Cys
        35                  40                  45

Arg Lys Ser Cys Arg Leu Arg Trp Leu Asn Tyr Val Lys Pro Asn Ile
    50                  55                  60

Lys Arg Gly Asp Phe Thr Glu Asp Glu Val Asp Leu Ile Ile Arg Leu
65                  70                  75                  80

His Lys Leu Leu Gly Asn Arg Trp Ser Leu Ile Ala Gly Arg Leu Gln
                85                  90                  95

Gly Arg Thr Ala Asn Asp Val Lys Asn Tyr Cys Asn Thr Arg Leu Arg
            100                 105                 110

Ile Asn Ser Arg Met Lys Thr Ser Gln Asn Lys Ser Gln Glu Thr Arg
        115                 120                 125

Lys Thr Ile Val Ile Arg Pro Gln Pro Arg Ser Phe Ile Lys Ser Ser
130                 135                 140

Asn Tyr Leu Ser Ser Lys Glu Pro Ile Leu Asp His Ile Gln Ser Glu
145                 150                 155                 160

Glu Asp Ser Ser Thr Pro Ser Gln Thr Ser Leu Thr Lys Asn Gly Asn
                165                 170                 175

Asp Arg Trp Glu Thr Leu Leu Lys Asp Glu Gly Thr Phe Glu Arg Thr
            180                 185                 190

```
Ala Tyr Pro Ser Phe Glu Leu Glu Glu Leu Phe Thr Ser Phe Trp
        195                 200                 205

Ala Asp Glu Met Gln Gln Ser Ala Arg Ser Cys Thr Val Ser Phe Pro
210                 215                 220

Glu Glu Gly Pro Ser Lys Ser Asn Leu Ser Phe Asn Met Glu Leu Trp
225                 230                 235                 240

Asn His Ser Lys Glu Glu
                245

<210> SEQ ID NO 18
<211> LENGTH: 225
<212> TYPE: PRT
<213> ORGANISM: Prunus dulcis

<400> SEQUENCE: 18

Met Glu Gly Tyr Asn Leu Gly Val Arg Lys Gly Ala Trp Thr Arg Glu
1               5                   10                  15

Glu Asp Asp Leu Leu Arg Gln Cys Ile Glu Asn Gln Gly Glu Gly Lys
            20                  25                  30

Trp His Gln Val Pro Tyr Lys Ala Gly Leu Lys Arg Cys Arg Lys Ser
        35                  40                  45

Cys Arg Leu Arg Trp Val Asn Tyr Leu Lys Pro Asn Ile Lys Arg Gly
50                  55                  60

Glu Phe Ala Glu Asp Glu Val Asp Leu Ile Ile Arg Leu His Lys Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr Arg Leu Arg Thr Asp Ser
            100                 105                 110

Arg Leu Lys Lys Val Lys Asp Lys Pro Gln Glu Thr Ile Lys Thr Ile
        115                 120                 125

Val Ile Arg Pro Gln Pro Arg Arg Phe Thr Lys Ser Ser Asn Cys Leu
130                 135                 140

Ser Phe Lys Glu Pro Ile Leu Asp His Thr Gln Arg Asp Trp Trp Glu
145                 150                 155                 160

Thr Phe Leu Asp Asp Lys Asp Ala Thr Glu Arg Ala Thr Gly Ser Gly
                165                 170                 175

Leu Gly Leu Asp Glu Glu Leu Leu Ala Ser Phe Trp Val Asp Asp Asp
            180                 185                 190

Met Pro Gln Ser Thr Arg Lys Cys Ile Asn Phe Ser Glu Gly Leu Ile
        195                 200                 205

Arg Gly Asp Phe Ser Phe Ser Val Asp Pro Trp Asn His Ser Lys Glu
210                 215                 220

Glu
225

<210> SEQ ID NO 19
<211> LENGTH: 244
<212> TYPE: PRT
<213> ORGANISM: Prunus avium

<400> SEQUENCE: 19

Met Glu Gly Tyr Asn Leu Gly Val Arg Lys Gly Ala Trp Thr Arg Gln
1               5                   10                  15

Glu Asp Asp Leu Leu Arg Gln Cys Ile Glu Asn Gln Gly Glu Gly Lys
            20                  25                  30

Trp His Gln Val Pro Tyr Lys Ala Gly Leu Asn Arg Cys Arg Arg Ser
```

```
                35                  40                  45
Cys Arg Leu Arg Trp Leu Asn Tyr Leu Lys Pro Asn Ile Lys Arg Gly
         50                  55                  60

Asp Phe Met Glu Asp Glu Val Asp Leu Ile Ile Arg Leu His Lys Leu
 65                  70                  75                  80

Leu Gly Asn Arg Trp Ser Leu Ile Ala Gln Arg Leu Pro Gly Arg Thr
                 85                  90                  95

Ala Asn Asp Val Lys Asn Tyr Trp Asn Thr Arg Leu Arg Met Asp Tyr
            100                 105                 110

Ser Leu Lys Lys Met Lys Asp Lys Ser Gln Glu Thr Ile Lys Thr Ile
        115                 120                 125

Ile Ile Arg Pro Gln Pro Arg Ser Phe Thr Lys Ser Ser Asn Cys Leu
    130                 135                 140

Ser Phe Lys Glu Pro Ile Leu Asp His Thr Gln Leu Glu Glu Asn Phe
145                 150                 155                 160

Ser Thr Pro Ser Gln Thr Ser Thr Ser Thr Arg Ile Gly Ser Asp Trp
                165                 170                 175

Trp Glu Thr Phe Leu Asp Asp Lys Asp Ala Thr Glu Arg Ala Thr Gly
            180                 185                 190

Ser Gly Leu Gly Leu Asp Glu Glu Leu Leu Ala Ser Phe Trp Val Asp
        195                 200                 205

Asp Asp Met Pro Gln Ser Thr Arg Thr Cys Ile Asn Phe Ser Glu Glu
    210                 215                 220

Gly Leu Ser Arg Gly Asp Phe Ser Phe Ser Val Asp Leu Trp Asn His
225                 230                 235                 240

Ser Lys Glu Glu

<210> SEQ ID NO 20
<211> LENGTH: 247
<212> TYPE: PRT
<213> ORGANISM: Mespilus germanica

<400> SEQUENCE: 20

Met Glu Gly Tyr Asn Val Asn Leu Ser Val Arg Lys Gly Ala Trp Thr
 1               5                  10                  15

Arg Glu Glu Asp Asn Leu Leu Arg Gln Cys Ile Glu Ile His Gly Glu
            20                  25                  30

Gly Lys Trp Asn Gln Val Ser Tyr Lys Ala Gly Leu Asn Arg Cys Arg
        35                  40                  45

Lys Ser Cys Arg Leu Arg Trp Leu Asn Tyr Leu Lys Pro Ser Ile Lys
    50                  55                  60

Arg Gly Asp Phe Lys Glu Asp Glu Val Asp Leu Ile Ile Arg Leu His
 65                  70                  75                  80

Lys Leu Leu Gly Asn Arg Trp Ser Leu Ile Ala Gln Arg Leu Pro Gly
                 85                  90                  95

Arg Thr Ala Asn Asp Val Lys Asn Tyr Trp Asn Thr Arg Leu Arg Met
            100                 105                 110

Asp Tyr Ser Leu Lys Lys Met Lys Asp Lys Ser Gln Glu Thr Ile Lys
        115                 120                 125

Thr Ile Ile Ile Arg Pro Gln Pro Arg Ser Phe Thr Lys Ser Ser Asn
    130                 135                 140

Cys Leu Ser Phe Lys Glu Pro Ile Leu Asp His Thr Gln Leu Glu Glu
145                 150                 155                 160

Asn Phe Ser Thr Pro Ser Gln Thr Ser Thr Ser Thr Arg Ile Gly Ser
                165                 170                 175
```

```
Asp Trp Trp Glu Thr Phe Leu Asp Asp Lys Asp Ala Thr Glu Arg Ala
            180                 185                 190

Thr Gly Ser Gly Leu Gly Leu Asp Glu Glu Leu Leu Ala Ser Phe Trp
            195                 200                 205

Val Asp Asp Asp Met Pro Gln Ser Thr Arg Thr Cys Ile Asn Phe Ser
            210                 215                 220

Glu Glu Gly Leu Ser Arg Gly Glu Leu Ser Phe Ser Thr Asp Leu Trp
225                 230                 235                 240

Asn His Ser Lys Lys Asn Ser
                245

<210> SEQ ID NO 21
<211> LENGTH: 237
<212> TYPE: PRT
<213> ORGANISM: Prunus domestica

<400> SEQUENCE: 21

Met Glu Gly Tyr Asn Val Gly Val Arg Lys Gly Ala Trp Thr Arg Glu
1               5                   10                  15

Glu Asp Asp Leu Leu Arg Gln Cys Ile Glu Asn His Gly Glu Gly Lys
            20                  25                  30

Trp His Gln Val Pro Asn Lys Ala Gly Leu Asn Arg Cys Arg Lys Ser
        35                  40                  45

Cys Arg Leu Arg Trp Leu Asn Tyr Leu Lys Pro Asn Ile Lys Arg Gly
    50                  55                  60

Glu Phe Ala Glu Asp Glu Val Asp Leu Ile Ile Arg Leu His Lys Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr Arg Leu Arg Lys Val Lys
            100                 105                 110

Asp Lys Pro Gln Glu Thr Ile Lys Thr Ile Val Ile Arg Pro Gln Pro
        115                 120                 125

Arg Ser Phe Ile Lys Ser Ser Asn Cys Leu Ser Ser Lys Glu Pro Ile
    130                 135                 140

Leu Asp His Ile Gln Thr Val Glu Asn Phe Ser Thr Pro Ser Gln Ser
145                 150                 155                 160

Ser Pro Ser Thr Lys Asn Gly Asn Asp Trp Trp Glu Thr Phe Leu Asp
                165                 170                 175

Asp Glu Asp Val Phe Glu Lys Ala Thr Cys Tyr Gly Leu Ala Leu Glu
            180                 185                 190

Glu Glu Glu Phe Thr Ser Phe Trp Val Asp Asp Met Pro Gln Ser Lys
        195                 200                 205

Arg Gln Cys Thr Asn Val Thr Glu Glu Gly Leu Gly Thr Gly Asp Phe
    210                 215                 220

Ser Phe Asn Val Asp Leu Trp Asn His Ser Lys Glu Glu
225                 230                 235

<210> SEQ ID NO 22
<211> LENGTH: 729
<212> TYPE: DNA
<213> ORGANISM: Malus sylvestris

<400> SEQUENCE: 22
atggagggat ataacgaaaa cctgagtgtg agaaaaggtg cctggactcg agaggaagac     60
aatcttctca ggcagtgcgt tgagattcat ggagagggaa agtggaacca agtttcatac    120
```

| | |
|---|---:|
| aaagcaggct taaacaggtg caggaagagc tgcagacaaa gatggttaaa ctatctgaag | 180 |
| ccaaatatca agagaggaga ctttaaagag gatgaagtag atcttataat tagacttcac | 240 |
| aggcttttgg gaaacaggtg gtcattgatt gctagaagac ttccaggaag aacagcaaat | 300 |
| gctgtgaaaa attattggaa cactcgattg cggatcgatt ctcgcatgaa aacggtgaaa | 360 |
| aataaatctc aagaaatgag aaagaccaat gtgataagac ctcagcccca aaaattcaac | 420 |
| agaagttcat attacttaag cagtaaagaa ccaattctag accatattca atcagcagaa | 480 |
| gatttaagta cgccaccaca aacgtcgtcg tcaacaaaga atggaaatga ttggtgggag | 540 |
| accttgttag aaggcgagga tacttttgaa agagctgcat atcccagcat tgagttagag | 600 |
| gaagaactct tcacaagttt ttggtttgat gatcgactgt cgccaagatc atgcgccaat | 660 |
| tttcctgaag gacaaagtag aagtgaattc tcctttagca cggacctttg gaatcattca | 720 |
| aaagaagaa | 729 |

<210> SEQ ID NO 23
<211> LENGTH: 4088
<212> TYPE: DNA
<213> ORGANISM: Malus sylvestris

<400> SEQUENCE: 23

| | |
|---|---:|
| taagagatgg agggatataa cgaaaacctg agtgtgagaa aaggtgcctg gactcgagag | 60 |
| gaagacaatc ttctcaggca gtgcgttgag attcatggag agggaaagtg gaaccaagtt | 120 |
| tcatacaaag caggtatata tgttaatgtg tatatttaac tgtgaaagat ggatatgtgt | 180 |
| attattttaa agcatttcac tagtatttca ttctaagacc ttttgttaaa tagtttcaag | 240 |
| tttcaagttt tactttttatt aatgttttag aacatgttaa tatgtctaac ggtcatactt | 300 |
| gctctcacct cactcatcta ttgtgtttac atatatggct aaaatgacct atgcgtgtgt | 360 |
| gaggagggcc atgttgagag acttagtccc tcataaatat ttgttgttca cgtagaaaga | 420 |
| tgttatgtga atgtaaactt tgaattatgt atgcaggctt aaacaggtgc aggaagagct | 480 |
| gcagacaaag atggttaaac tatctgaagc caaatatcaa gagaggagac tttaaagagg | 540 |
| atgaagtaga tcttataatt agacttcaca ggcttttggg aaacaggtac taataaataa | 600 |
| gtgtcatttt caattcatgt cgtcgttttc attgtacgga aattggacct attaacagtg | 660 |
| agattataat catagacctc aaattacttt ttccactctt ttaatatttt aatgttttc | 720 |
| aatgaagtat tagtggtgtg tagaatataa aaaaaaataa aaggtgttgt gtaagtaatt | 780 |
| tggagtgtgt gaatataatc tttcttgtta atatattctg gctccccata ttttcagtat | 840 |
| tttctaatac ttcctaattt atatgtcatt ttattttttca tttagacatc aagcaaaaag | 900 |
| ttttcaattt tgtagtattt tttttagatt tattaaaaca attatttccc aaatttttt | 960 |
| tgtgggccaa tggcctacca catcattgtt tatggagaac ttaaaggcta gagtacgaag | 1020 |
| tatgatttta gagtaatcgt atttaggaat aaagtgagag gagaaaaact aagggtagca | 1080 |
| acttgcaaat ttcatgatac ttgagtatag taaagtgagg attactctta tttttagct | 1140 |
| atagtctagc atgagaatct aaactacaaa atcattagag agggcaagcg ttataaacat | 1200 |
| tcattttaaa ttttttaata ttataatatt ctaccttaag gggcagagtt gttttttggt | 1260 |
| taagcaaaac aaaaaatcat tcgtatcaaa tgtggtatca ttgaaaatca aacttcagac | 1320 |
| ttagtctcta atttttaaaa tgaagacaaa tatcgagtgc taatagcaat aaaccaaaaa | 1380 |
| ttttaggaac tgtttggtat cttatttgaa atttttatc atttctcaaa acattttta | 1440 |
| aaaacatttc ttgaaaacaa ttttctttaa gactcaaaaa cttgatgggt atgcaaatta | 1500 |

```
aaaatttcaa atcttacgac tttaactaga caaagagatc taaacagagg gggtcacggt    1560
agagggagaa agaagagaga ggaggaaaaa aagtaagaga tgattgaatg aaagagaaag    1620
aagagagatg atcggatgaa atagagagga atatgagtga gagaaagaac tgagaggata    1680
aaaagagcag attggagaaa agacgaaaaa ggtaataaaa aaaaggagag agaaagaaga    1740
aaagagagag atagatttgg agagagagag gaggaaggag agaaaataaa taagagagtt    1800
taagtttaaa aactctaaaa ctcactttt atgttttag ataatagact atattttga       1860 gttagtcttg agttcaattt ttaaaaatag tcctaccaaa aaagttttta aggcctaaaa    1920
cttgaaaatt gttttgagt ttaaaagtt ggattcaaat aaagtatcaa acaggtcctt      1980
agttttttct tgaccgaaaa aataaaaatc tttatccgga agggcattag taaactcaaa    2040
caacctttct tcgtaatgat ttttgtatgt aaagtcattt tcatgctttt aatccctagt   2100
cgactgagca aacctttaag attgtgtatt cggccaacag aggcttggat cagaatagat    2160
aagaagttat acattcaaaa tttcacaatt aatagaatta aagggagaa ctttggtaat     2220 aaatacacgc agtaatttta ttttttgtat taaaactaat gttcgggcaa ggatttggcc    2280
ttggcacagc tcccttggag tgttggcact tggcgttgat gttggttgtt ggtcgagttc    2340
ttgctacttg gtgtgctaca agaagagtac aaagttagtt ttgaaatgtg cctttgtggg    2400
gccttagatg taggtcttga ggctcacaat caaaactaac aaaaagttag gcgtgccact    2460
gttatctcaa tataatagat gttgaatata tttgatctaa gtcgattact tgcgcccaa     2520 gatgcttaaa cttcttatta tcaaaggatt gtcacaaatg ggttaagtct gcattaagtt    2580 cttttcttg ccttgtgacc aaggactttt tcttatagtt ttgtatgtta gatgaaggag     2640 tccatacct ttatcattcg ctgattacaa ttcgacgcta aagaagtgaa gttacttgct     2700
tagccaaatt gatcataaat gggtcttaga gcgagaacaa tgtaagtgag ttaaaacata    2760
acataatatg catttaaaca acaaatctac aaactgtaag tacaacacaa ggaagttggg    2820
caagatttca tcttgtcggg caaggttcaa acctcttgca accacttctc cttgagtttg    2880
tagaagagtt gtgggtactg caaaatgaaa atgtaagcag gaaatacaaa caaggtttcc    2940
taaagggaat ctattctacg aatctaggat aaggtagcag agctttgcca aaagatggct    3000
ttctgcgtgg aatctatggc taaaaggtgc ataatctgga cgaagtgcag cttttggtt    3060 atttgcttgt ctgagaggca agtttgtatg tcttttgttt gattggttga gtgtccttgt    3120
ctctgttgtc tctttctcct tttatagacg atttggcccg actgcttttg gctctattct    3180
tgtccgaaag ctcttggagg gcaatgagtc atcatctttt tacttgtagt gccattagaa    3240 agtgttttt ggctaatagt gagttgatct ctgtcacttg tcacttcact cctacacatg     3300
tggcctatat tttaattgag gaggcaccaa tttgttccag gcttgtcgac tgggcctcgg    3360
gcaagtcttc acttaatttg acatccatgg gtcttggcta tttacaaaac cttatgttaa    3420
atattaactc aaacaactag tccactccat ttaattctaa agaagaaaat cgtttatgca    3480
atctctgttc ctttttttt cttttattcat cttattttc aggcaaatgt attcatcatt    3540 tttcttcat gcatgtaatg tacttaggtg gtcattgatt gctagaagac ttccaggaag    3600
aacagcaaat gctgtgaaaa attattggaa cactcgattg cggatcgatt ctcgcatgaa    3660
aacggtgaaa aataaatctc aagaaatgag aaagaccaat gtgataagac ctcagccca    3720 aaaattcaac agaagttcat attacttaag cagtaaagaa ccaattctag accatattca    3780
atcagcagaa gatttaagta cgccaccaca aacgtcgtcg tcaacaaaga atggaaatga    3840
ttggtgggag accttgttag aaggcgagga tactttgaa agagctgcat atcccagcat     3900
```

| | |
|---|---|
| tgagttagag gaagaactct tcacaagttt ttggtttgat gatcgactgt cgccaagatc | 3960 |
| atgcgccaat tttcctgaag gacaaagtag aagtgaattc tcctttagca cggacctttg | 4020 |
| gaatcattca aaagaagaat agctagagaa aatgattctc acttctgtgg taccatctag | 4080 |
| cttgtgta | 4088 |

<210> SEQ ID NO 24
<211> LENGTH: 735
<212> TYPE: DNA
<213> ORGANISM: Pyrus communis

<400> SEQUENCE: 24

| | |
|---|---|
| atggagggat ataacgttaa cttgagtgtg agaaaaggtg cctggactcg agaggaagac | 60 |
| aatcttctca ggcagtgcat tgagattcat ggagagggaa agtggaacca agtttcatac | 120 |
| aaagcaggct taaacaggtg taggaagagc tgcagacaaa gatggttaaa ctatctgaag | 180 |
| ccaaatatca agagaggaga cttttaaagag gatgaagtag atcttatact tagacttcac | 240 |
| aggcttttgg gaaacaggtg gtcattgatt gctagaagac ttccaggaag aacagcgaat | 300 |
| gatgtgaaaa attattggta cactcgattg cggatcgatt ctcgcatgaa aacggtgaaa | 360 |
| aataaatctc aagaaacgag aaagaccaat gtgataagac ctcagcccca aaaatttatc | 420 |
| aaaagttcat attacttaag cagtaaagaa ccaattctag aacatattca atcagcagaa | 480 |
| gatttaagta cgccatcaca aacgtcgtcg tcaacaaaga acggaaatga ttggtgggag | 540 |
| accttgttcg aaggcgagga tacttttgaa agggctgcat gtcccagcat tgagttagag | 600 |
| gaagaactct tcacaagttt ttggtttgat gatcgactgt cggcaagatc atgtgccaat | 660 |
| tttcctgaag aaggacaaag tagaagtgaa ttctcccttta gcatggacct ttggaatcat | 720 |
| tcaaaagaag aatag | 735 |

<210> SEQ ID NO 25
<211> LENGTH: 1595
<212> TYPE: DNA
<213> ORGANISM: Pyrus communis

<400> SEQUENCE: 25

| | |
|---|---|
| taagagatgg agggatataa cgttaacttg agtgtgagaa aaggtgcctg gactcgagag | 60 |
| gaagacaatc ttctcaggca gtgcattgag attcatggag agggaaagtg gaaccaagtt | 120 |
| tcatacaaag caggtatata tgttaatgtg tatatttaac tgtgaaagat ggatatgtgt | 180 |
| attattttaa agcatttcac tagtatttca ttctaagacc ttttattaaa tagtttcaag | 240 |
| tttcaagttt tacttttatt aatgttttag aacatgttaa tgtgtttaac ggtcatactt | 300 |
| gctctcactt cagtaatcta ttgtgtttac atatatggct aaaatgacct ctgcgtgtgt | 360 |
| gaggagggcc atgttgagag acttagtccc tcataaatat gtattgttca cgtagaaaga | 420 |
| tgttatgcga atataaactt tgaattatgt atgcaggctt aaacaggtgt aggaagagct | 480 |
| gcagacaaag atggttaaac tatctgaagc caaatatcaa gagaggagac ttttaaagag gagac | 540 |
| atgaagtaga tcttatactt agacttcaca ggcttttggg aaacaggtac taataaatgg | 600 |
| atcaggatcg caaatggtga ggatcctcct gaacaggccc atcgggccat tcaaattta | 660 |
| tctaacggct acaaacagga gattcctcta aaagttatag cagtgggtc atcatttttt | 720 |
| tacttgtagt gccactagaa aatgcttttt ggttgatagt gagttgatct ccatgacttg | 780 |
| tcacttcact cctaagcatg tggcctatat tttaattgag gaggcgccaa tttgttccaa | 840 |
| gcttgtcgac ggggccttgg gcaagtcttc acttaatttg acatccatgg gccttggcta | 900 |

| | |
|---|---:|
| tttacaaaac cctatgttaa atattaaacc aaacaaccag tccactccat ttaattctaa | 960 |
| agaagaaaat cgtttaagca atctctgttc ttttttttt ggtcgcttta ttcatcttat | 1020 |
| ttttcagcca aatgtattca tcattttttt cttcatgcat gtaatgtact caggtggtca | 1080 |
| ttgattgcta gaagacttcc aggaagaaca gcgaatgatg tgaaaaatta ttggtacact | 1140 |
| cgattgcgga tcgattctcg catgaaaacg gtgaaaaata atctcaaga acgagaaag | 1200 |
| accaatgtga taagacctca gccccaaaaa tttatcaaaa gttcatatta cttaagcagt | 1260 |
| aaagaaccaa ttctagaaca tattcaatca gcagaagatt taagtacgcc atcacaaacg | 1320 |
| tcgtcgtcaa caaagaacgg aaatgattgg tgggagacct tgttcgaagg cgaggatact | 1380 |
| tttgaaaggg ctgcatgtcc cagcattgag ttagaggaag aactcttcac aagttttttgg | 1440 |
| tttgatgatc gactgtcggc aagatcatgt gccaattttc ctgaagaagg acaaagtaga | 1500 |
| agtgaattct cctttagcat ggacctttgg aatcattcaa agaagaata gctagagaaa | 1560 |
| atgattctca cttctgtggt accatctagc ttgtg | 1595 |

<210> SEQ ID NO 26
<211> LENGTH: 732
<212> TYPE: DNA
<213> ORGANISM: Pyrus communis

<400> SEQUENCE: 26

| | |
|---|---:|
| atggagggat ataacgttaa cttgagtgtg agaaaaggtg cctggactcg agaggaagac | 60 |
| aatcttctca ggcagtgcat tgagattcat ggagaggaa agtggaacca ggtttcatac | 120 |
| aaagcaggct taaacaggtg caggaagagc tgcagacaaa gatggttaaa ctatctgaag | 180 |
| ccaaatatca agagaggaga cttaaagag gatgaagtag atcttatact tagacttcac | 240 |
| aggcttttgg gaaacaggtg gtcattgatt gctagaagac ttccaggaag aacagcgaat | 300 |
| gatgtgaaaa attattggaa cactcgattg gggatcgatt ctcgcatgaa aacgttgaaa | 360 |
| aataaatctc aagaaacgag aaagaccaat gtgataagac ctcagcccca aaaattcatc | 420 |
| aaaagttcat attacttaag cagtaaagaa ccaattctag aacatattca atcagcagaa | 480 |
| gatttaagta cgccatcaca aacgtcgtcg tcaacaaaga acggaaatga ttggtgggag | 540 |
| accttgttcg aaggcgagga tacttttgaa agggctgcat gtcccagcat tgagttagag | 600 |
| gaagaacttt tcacaacttt tggtttgat gatcgactgt cggcaagatc atgtgccaat | 660 |
| tttcctgaag aaggacaaag tagaagtgaa ttctccttta gcatggacct ttggaatcat | 720 |
| tcaaaagaag aa | 732 |

<210> SEQ ID NO 27
<211> LENGTH: 1591
<212> TYPE: DNA
<213> ORGANISM: Pyrus pyrifolia

<400> SEQUENCE: 27

| | |
|---|---:|
| taagagatgg agggatataa cgttaacttg agtgtgagaa aaggtgcctg gactcgagag | 60 |
| gaagacaatc ttctcaggca gtgcattgag attcatggag agggaaagtg gaaccaggtt | 120 |
| tcatacaaag caggtatata tgttaatgtg tatatttaac tgtgaaagat ggatatgtgt | 180 |
| attattttaa agcatttcac tagtatttca ttctaagacc ttttattaaa tagttttcaag | 240 |
| ttgaaagttt tacttttatt aatgtttttag aacatgttaa tgtgtttaac ggtcatactt | 300 |
| gctctcactt cagtaatcta ttgtgtttac atatatggct aaaatgacct ctgcgtgtgt | 360 |
| gaggagggcc atgttgagag acttagtccc tcataaatat gtattgttca cgtagaaaga | 420 |

```
tgttatgcga atttaaactt tgaattatgt atgcaggctt aaacaggtgc aggaagagct    480
gcagacaaag atggttaaac tatctgaagc caaatatcaa gagaggagac tttaagagg    540 atgaagtaga tcttatactt agacttcaca ggcttttggg aaacaggtac taataaatgg    600
atcaggatcg caaatggtga ggatcctcct gaccaggctc atcgggccat tcaaatttta    660
tccaacagat acaaataggg ggtccctcta aaagttatag gcagtgagtc atcatctttt    720
tatttgtagt gctactagaa agtactttt  ggttgatagt gagttgatct ccatcacttg    780
tcacttcatt gcatgtggcc tataattaa  ttgaggtggt gccaatttgt tccaggcttg    840
tcgactgggc cttgggcaag tcttcactta atttgacatc catgggcctt ggctatttac    900
aaaaccctat gttaaatatt aaccaaaca  gccagtccac tacatttaat tctaaagaag    960
aaaatcattt aagcaatctc tgttcttttt  tttttggtcg ctttattcat cttatttttc   1020
agccaaatgt attcatcatc tttttctc   atgcatgtaa tgtactcagg tggtcattga   1080
ttgctagaag acttccagga agaacagcga atgatgtgaa aaattattgg aacactcgat   1140
tggggatcga ttctcgcatg aaaacgttga aaaataaatc tcaagaaacg agaaagacca   1200
atgtgataag acctcagccc caaaaattca tcaaagttc  atattactta agcagtaaag   1260
aaccaattct agaacatatt caatcagcag aagatttaag tacgccatca caaacgtcgt   1320
cgtcaacaaa gaacggaaat gattggtggg agaccttgtt cgaaggcgag gatacttttg   1380
aaagggctgc atgtcccagc attgagttag aggaagaact tttcacaact ttttggtttg   1440
atgatcgact gtcggcaaga tcatgtgcca attttcctga agaaggacaa agtagaagtg   1500
aattctcctt tagcatggac ctttggaatc attcaaaaga agaatagcta gagaaaatga   1560
ttctcacttc tgtggtacca tctagcttgt g                                  1591

<210> SEQ ID NO 28
<211> LENGTH: 732
<212> TYPE: DNA
<213> ORGANISM: Pyrus bretschneideri

<400> SEQUENCE: 28
atggagggat ataacgttaa cttgagtgtg agaaaaggtg cctggactcg agaggaagac     60
aatcttctca ggcagtgcat tgagattcat ggagagggaa agtggaacca ggtttcatac    120
aaagcaggct taaacaggtg caggaagagc tgcagacaaa gatggttaaa ctatctgaag    180
ccaaatatca agagaggaga ctttaaagag gatgaagtag atcttatact tagacttcac    240
aggcttttgg gaaacaggtg gtcattgatt gctagaagac ttccaggaag aacagcgaat    300
gatgtgaaaa attattggaa cactcgactg gggatcgatt ctcgcatgaa aacgttgaaa    360
aataaatctc aagaaacgag aaagaccaat gtgataagac ctcagcccca aaaattcatc    420 aaagttcat  attacttaag cagtaaagaa ccaattctag aacatattca atcagcagaa    480
gatttaagta cgccatcaca aacgtcgtcg tcaacaaaga acggaaatga ttggtgggag    540
accttgttcg aaggcgagga tacttttgaa agggctgcat gtcccagcat tgagttagag    600
gaagaacttt tcacaacttt ttggtttgat gatcgactgt cggcaagatc atgtgccaat    660
tttcctgaag aaggacaaag tagaagtgaa ttctccttta gcatggacct ttggaatcat    720
tcaaaagaag aa                                                        732

<210> SEQ ID NO 29
<211> LENGTH: 1596
<212> TYPE: DNA
<213> ORGANISM: Pyrus bretschneideri
```

<400> SEQUENCE: 29

```
taagagatgg agggatataa cgttaacttg agtgtgagaa aaggtgcctg gactcgagag      60
gaagacaatc ttctcaggca gtgcattgag attcatggag agggaaagtg gaaccaggtt     120
tcatacaaag caggtatata tgttaatgtg tatatttaac tgtgaaagat ggatatgtgt     180
attatttta  agcatttcac tagtatttca ttctaagacc ttttattaaa tagtttcaag     240
ttgaaagttt tacttttatt aatgttttag aacatgttaa tgtgtttaac ggtcatactt     300
gctctcactt cagtaatcta ttgtgtttac atatatggct aaaatgacct ctgcgtgtgt     360
gaggagggcc atgttgagag acttagtccc tcataaatat gtattgttca cgtagaaaga     420
tgttatgcga atttaaactt tgaattatgt atgcaggctt aaacaggtgc aggaagagct     480
gcagacaaag atggttaaac tatctgaagc caaatatcaa gagaggagac tttaagagg      540
atgaagtaga tcttatactt agacttcaca ggcttttggg aaacaggtac taataaatgg     600
atcaggatcg caaatggtga ggatcctcct gaccaggctc atcgggccat tcaaatttta     660
tccaacagat acaaataggg ggtccctcta aaagttatag gcagtgagtc atcatctttt     720
tatttgtagt gttactagaa agtacttttt ggttgatagt gagttgatct ccatcacttg     780
tcacttcgct cgtaggcatg tggcctataa tttaattgag gtggtgccaa tttgttccag     840
gcttgtcaac tgggccttgg gcaagtcttc acttaatttg acatccatgg gccttggcta     900
tttacaaaac cctatgttaa atattaaacc aaacagccag tccactacat ttaattctaa     960
agaagaaaat catttaagca atctctgttc tttttttttt ggtcgcttta ttcatcttat    1020
ttttcagcca aatgtattca tcatcttttt tcttcatgca tgtaatgtac tcaggtggtc    1080
attgattgct agaagacttc caggaagaac agcgaatgat gtgaaaaatt attggaacac    1140
tcgactgggg atcgattctc gcatgaaaac gttgaaaaat aaatctcaag aaacgagaaa    1200
gaccaatgtg ataagacctc agccccaaaa attcatcaaa agttcatatt acttaagcag    1260
taaagaacca attctagaac atattcaatc agcagaagat ttaagtacgc catcacaaac    1320
gtcgtcgtca acaaagaacg gaaatgattg gtgggagacc ttgttcgaag gcgaggatac    1380
ttttgaaagg gctgcatgtc ccagcattga gttagaggaa gaacttttca caacttttg     1440
gtttgatgat cgactgtcgg caagatcatg tgccaatttt cctgaagaag gacaaagtag    1500
aagtgaattc tcctttagca tggaccttg gaatcattca aaagaagaat agctagagaa     1560
aatgattctc acttctgtgg taccatctag cttgtg                              1596
```

<210> SEQ ID NO 30
<211> LENGTH: 735
<212> TYPE: DNA
<213> ORGANISM: Cydonia oblonga

<400> SEQUENCE: 30

```
atggagggat ataacgttaa cttgagtgtg atgagaaaag gtgcctggac tcgagaggaa      60
gatgatcttc tcaggcagtg cattgggatt cttggagaag gaaagtggca ccaagttcct     120
tacaaaacag gcttaaacag gtgcaggaag agctgcagac taagatggtt gaactatctg     180
aagccaaata tcaagagagg agactttaca gaggatgaag tagatcttat aattaggctt     240
cacaagcttt taggaaacag gtggtcgttg attgctggaa gacttccagg aagaacagcg     300
aatgatgtga aaattattg  gaacactcga ttacggatca attctcgcat gaaaacattg     360
aaaaataaat ctcaagaaac gagaagacc  aatgtgataa gacctcagcc ccgaaaattc     420
atcaaaagtt catattactt aagcagtaaa ggaccaattc tagaccatat tcaatcagca    480
```

```
gaagatttaa gtacgccacc acaaacgtcg tcgtcaacaa agaatggaaa tgattggtgg    540
gagaccttgt ttgaaggcga ggatactttt gaaagagctg catgtcccag cattgagtta    600
gaggaagaac tcttcacaag ttttggtttt gatgatcgac tgtcagcaag atcatgtgcc    660
aattttcctg aagaaggaca agtagaagt gaattctccg ttagcatgga cctttggaat     720
cattcaaaag aagaa                                                     735

<210> SEQ ID NO 31
<211> LENGTH: 2488
<212> TYPE: DNA
<213> ORGANISM: Cydonia oblonga

<400> SEQUENCE: 31
taagagatgg agggatataa cgttaacttg agtgtgatga gaaaaggtgc ctggactcga     60
gaggaagatg atcttctcag gcagtgcatt gggattcttg agaaggaaa gtggcaccaa    120 gttccttaca aaacaggtat atatgttaat gtgtatatat aactgagaaa gatggatacg   180
tgtattgcta ggaaagcatt tcattagtat atttcattct aagaccttct gccaattggt   240
ttcaagttgg atgttatgct tttattaatg ctttagaaca tgctaacgcg tctaacagtt   300
atacatggcc cacgtcgaga gagttcatcc cacattggaa acctcctcat gaaaacacat   360
tgcggacata tttgcagtac ataaatgtta tcaatttgca ttctgtgtct atgcaggctt   420
aaacaggtgc aggaagagct gcagactaag atggttgaac tatctgaagc caaatatcaa   480
gagaggagac tttacagagg atgaagtaga tcttataatt aggcttcaca agctttttagg  540 aaacaggtac taattaataa ataaacttca gtttcaattc ctatcctagc tgaaggacac   600
tccacacatc gtcctcatta ttgaacttgt tgataccctt aattaatcga gcttatgctc   660
taagagactc ttcagtgtgc cgggaacaca ggaacattcg tcatatatca attatacaag   720
tgaatggaca cttgaaaaaa aaaaaaaaaa gtttatccac ttgtataata acataagatg   780
tactgtcctg tgtttcacgc acattgaaaa tttcaccatg ctttattatt actttcatta   840
cacagtttaa taaataaaa aatttgatgt ggataatcag tgaatggacc taacaaacca    900
aaccaataat aactcacaaa atgaacttat aataagttta ctcttcattt tatgatatat   960
atatatatct taagggaat agttctttt ggttagcaaa taataaataa tcgtaataaa    1020
cagtatctca ctcgctattt tgaaatcgac tcagactcat attacatgtg aaaaaaaata  1080
tcaagtgcta gtagcaataa atcatgaatc ttagtgaccg aaaaattaaa tctttgtcca  1140
aaagggcatg agtaaactca aacaatgctt cctatggaag ataagtatct cgtaataaga  1200
ttttgtacgt agtcattttc atgcttttaa tcctactcgg ctcgacaaat cttttgtgatt 1260 ttgtacgttc ggcctggtac agaggcttgg atcagaattg gtaaaaacta taaaaacaaa  1320
tatgctgact ccatttctta ctgctgaccg tcaagtttct cttttgattgt caatgtaagt 1380 tttcagtcac atgaaaaaaa aatgtttgtc gtaccagtat atgccacgag ccaaacaaaa  1440
ttggaaaatc ttggatgtaa atatccttga tatatataag atcttatata tcaactgggg  1500
cgtagaaact cccccattaa accgatggcg actactcctc aaacaatttt tttattacat  1560
gttctcggat gagggagagt ttgaacgcaa tatggcagtc aaatactatc ttgaaattaa  1620
tagattttag agcctcgata aattccttct ttttttttt tacaataatg ttagtgaatt   1680
aaattgtttg ttgttaggga ggagagagtt gagtggaaat cgaacccgca ccaaggcaca  1740
tatatgcatg attgctttcc accactacta taaagcgtca tctgctaaat taattctcac  1800
caatctatat tgttatcact ttatgtatta aattagttca ctccatttaa ttctaaagaa  1860
```

```
gaaaaatgtt aacgcaatct aacatttttt ttatttatt tttgctttgt tcctcttatt    1920
tttcatccga agtattcatg attttttttc ttgtatatac tcaggtggtc gttgattgct    1980
ggaagacttc caggaagaac agcgaatgat gtgaaaaatt attggaacac tcgattacgg    2040
atcaattctc gcatgaaaac attgaaaaat aaatctcaag aaacgagaaa gaccaatgtg    2100
ataagacctc agccccgaaa attcatcaaa agttcatatt acttaagcag taaaggacca    2160
attctagacc atattcaatc agcagaagat ttaagtacgc caccacaaac gtcgtcgtca    2220
acaaagaatg gaaatgattg gtgggagacc ttgtttgaag gcgaggatac ttttgaaaga    2280
gctgcatgtc ccagcattga gttagaggaa gaactcttca caagtttttg gtttgatgat    2340
cgactgtcag caagatcatg tgccaatttt cctgaagaag gacaaagtag aagtgaattc    2400
tccgttagca tggacctttg gaatcattca aaagaagaat agctagagaa aatgattctc    2460
acttctgtgg taccatctag cttgtgta                                      2488
```

<210> SEQ ID NO 32
<211> LENGTH: 729
<212> TYPE: DNA
<213> ORGANISM: Prunus salicina

<400> SEQUENCE: 32

```
atggagggat ataacttggg tgtgagaaaa ggagcttgga ctagaaagga agatgatctt      60
ctgaggcagt gcattgagaa acacggagaa ggaaagtggc accaagttcc ttacaaagca    120
ggattaagca gatgcaggaa gagctgtaga ctaaggtggt tgaactattt gaagccaaat    180
atcaagagag gagactttat ggaagatgaa gtagatctaa taattaggct tcacaagctt    240
ttaggaaaca ggtggtcatt gattgctcga agacttccgg gaaggactgc caatgatgtg    300
aaaaattact ggaacacccg attgcggacg gattattgca tgaaaaagat gaaagacaaa    360
tcccaagaaa cataaagac cataataagg ccacaaccaa gaagattcac caaaagttca    420
aattgtttga gttttaaaga accaattttg gaccatactc aactagaaga gaattttagt    480 acgcatcac aaatatcaac atcaacaagg attggaagtg attggtggga gaccttttta    540
gatgacaagg atgctactga aacagctaca ggttctggtc ttgggttaga tgaagaactg    600
ctcgcaagtt tttgggttga tgatgatatg ccacaatcga caagaacatg cgtcaatttt    660
tctgaggaag gattaagtag aggtgatttc tcttttagcg tggacctttg gaatcattca    720
aaagaagaa                                                            729
```

<210> SEQ ID NO 33
<211> LENGTH: 1890
<212> TYPE: DNA
<213> ORGANISM: Prunus salicina

<400> SEQUENCE: 33

```
taagagatgg agggatataa cttgggtgtg agaaaaggag cttggactag aaaggaagat      60
gatcttctga ggcagtgcat tgagaaacac ggagaaggaa agtggcacca agttccttac    120
aaagcaggta ttaatgtgaa atataactcc aaaagaggga tagatatatg gtatatagag    180
ctacagctta attaagtagt gaagcgttgt cttagtattg tttcttaaca cacacaaaaa    240
caacatcctg aacttctcca ctcactgtta attggttttc tgtacgtgtt ctgctcaagg    300
gatgtcatac ataaaaggcc attttgatat gcatgttgta acaaagacaa aaacgaagtt    360
taagacgcag cctgagaatt tcatgacaag ttttgtgata aaaactcaat ttttgcaata    420
tgcacgtgtg caggattaag cagatgcagg aagagctgta gactaaggtg gttgaactat    480
```

```
ttgaagccaa atatcaagag aggagacttt atggaagatg aagtagatct aataattagg      540
cttcacaagc ttttaggaaa caggtaccaa taaataaatg tctctttcct cgctcataac      600
acacatggta caagcaagca tgtgccagca tatcccgcgc ttttttattt tttttattt       660 ttgtctcgga aggacaaaat aaatggagag tttggtgcga caccaattta aggatggcac      720
aataatattc tccccaacat tattgtttcc cgtacttagc aaaaattaaa ttaatatatc      780
aatccatagg aaatttattt gctctttgtt ttcttgggtg aaatttttata cctatgttgg     840 gatccttttc cttttacttt attcatcttt gttattggta aaatctttca aacacaaacc      900
agcatacaaa aagttggctc cctttgagat agtttggagc tctaaagagg ggaagatgtt      960
cggttgtgtt gggttcaggc ttagccaata cgggattatg ggtttagtcg gtatgacggt     1020
atgacgctat gattttcttc aggttgcctg gaagatgtgg agtagttgtc ttatatttct     1080
tagttttgtt ttagattaat aattttcaaa aactctttag gagtttgctg tgaattttttt    1140 ttttatattt aaaatgttta gttctttttta gcttttggct ttcaatacga atttactgtt    1200
tctaccgttt gcgcggcaaa tttatattgt atgtctaagt acatgtactg cttatagttt     1260
gctggatcga ggatttagtc attatttaag ttatgcgtga ttctctccag atcaattcaa     1320
tatgttgttg tgtttagtca ctggagaaga tttactcata ttcggcactt agttgttttg     1380
tactttctca tgctatgtgt tgaaggtggt cattgattgc tcgaagactt ccgggaagga     1440
ctgccaatga tgtgaaaaat tactggaaca cccgattgcg gacggattat tgcatgaaaa     1500
agatgaaaga caaatcccaa gaaacaataa agaccataat aaggccacaa ccaagaagat     1560
tcaccaaaag ttcaaattgt ttgagtttta agaaccaat tttggaccat actcaactag      1620
aagagaattt tagtacgaca tcacaaatat caacatcaac aaggattgga agtgattggt     1680 gggagaccctt tttagatgac aaggatgcta ctgaaacagc tacaggttct ggtcttgggt    1740
tagatgaaga actgctcgca agttttttggg ttgatgatga tatgccacaa tcgacaagaa    1800
catgcgtcaa ttttttctgag gaaggattaa gtagaggtga tttctctttt agcgtggacc    1860
tttggaatca ttcaaaagaa gaatagctag                                      1890
```

<210> SEQ ID NO 34
<211> LENGTH: 729
<212> TYPE: DNA
<213> ORGANISM: Prunus cerasifera

<400> SEQUENCE: 34

```
atggagggat ataacttggg tgtgagaaaa ggagcttgga ctagaaagga agatgatctt       60
ctgaggcagt gcattgagaa acacggagaa ggaaagtggc accaagttcc ttacaaagca      120
ggattaagca gatgcaggag gagctgtaga ctaaggtggt tgaactattt gaagccaaat      180
atcaagagag gagactttat ggaagatgaa gtagatctaa taattaggct tcacaagctt      240
ttaggaaaca ggtggtcatt gattgctcga agacttccgg gaaggactgc gaatgatgtg      300
aaaaattact ggaacacccg attgcggaag gattattgca tgaaaagat gaaagacaaa       360 tcccaagaaa caataaagac cataataagg ccacaaccaa gagcttcac caaaagttca      420 aattgtttga gttttaaaga accaattttg gaccatactc aactagaaga gaattttagt      480
acgccatcac aaacatcaac ttcaacaagg attgaagtg attggtggga gacctttta        540 gatgacaagg atgctactga aagagataca ggttctggtc ttgggttaga tgaagaactg      600
ctcgcaagtt ttggggttga tgatgatatg ccacaatcga caagaacatg cgtcaatttt      660
tctgaagaag gattaagtag aggtgatttc tcttttagcg tggacctttg gaatcattca      720
```

```
aaagaagaa                                                              729

<210> SEQ ID NO 35
<211> LENGTH: 1970
<212> TYPE: DNA
<213> ORGANISM: Prunus cerasifera

<400> SEQUENCE: 35
taagagatgg agggatataa cttgggtgtg agaaaaggag cttggactag aaaggaagat        60
gatcttctga ggcagtgcat tgagaaacac ggagaaggaa agtggcacca agttccttac       120
aaagcaggta ttaatgtgaa atataactcc aaaagaggga cagatatatg gtatatagag       180
ctacagctta attaagtagt gaagcgttgt cttagtattg tttcttaaca cacacaaaaa       240
cgacatcctg aacttctcca ctcatgttaa ttggttttct atacgtgttc tgcttaaggg       300
atgtcatgca taaaggccat tttaatatgc atgctaaac aaagacaaaa acgaagttta        360
agacagcctg ataatttcat gacaagtttt gtgacaaaaa ctcaattttt gcaatatgca       420
cgtgtgcagg attaagcaga tgcaggagga gctgtagact aaggtggttg aactatttga       480
agccaaatat caagagagga gactttatgg aagatgaagt agatctaata attaggcttc       540
acaagctttt aggaaacagg taccaataaa taaatgtctc tttcctcgct cataacacac       600
atggtacaag catgtgccag cgtatcccgt gcttttttt atgtttttt attttgtctc         660
ggaaggacaa aataaatgga gagtttggtg cgacaccaat taaaggatgg cacaataata       720
ttctccccaa cattattgtt tcccgtacct agcaaaaatt aaattaatat atccatccat       780
aggaaattta tttgctcttt gttttcttgg gtgaaatttt atacctatgt tgggctcctt       840
ttccttttac tttattcatc tttgttatcg gtaaatctt tcaaacacaa actagcatac        900
aaggagttgg ctccctttga cataatttga agttctaaag aggagaaaat gtttggttgt       960
gttgggttcg ggcttagcca gtacgggact atgggtttag ctggtatgac gctatgattt      1020
tcttcggatt gcctggaaga tgtggagcaa ttgtcttata tttcttagta atgttttaga      1080
ttaataattt tcaaaaactc tttaggagtt tgctgtgaat tttttttttt ctatttaaac      1140
tgtttatttc ttttttagctt ttggcttttcg atacgaattt gctgtttcta ccgtttgcgc    1200
ggcaaatttg tattgtatgt ctgagtacat attcttatgg ttgctggatc gaggatttag      1260
tcattattta agttgtgtgt gattctctcc agatcaattc aatatgttgt tgtgtttagt      1320
cactggagaa gatttactca tattcggcaa atagttgctt tgtacttta cttgttcatc       1380
aataatatac tatcgcttga ctttaaaaa aaatttaaaa aaaatttaaa aaaataaaaa        1440
ctagcataca aatgtattaa cttctcatg ctatatgtgt tgaaggtggt cattgattgc       1500
tcgaagactt ccgggaagga ctgcgaatga tgtgaaaaat tactggaaca cccgattgcg      1560
gaaggattat tgcatgaaaa agatgaaaga caaatcccaa gaaacaataa agaccataat      1620
aaggccacaa ccaagaagct tcaccaaaag ttcaaattgt ttgagtttta aagaaccaat      1680
tttggaccat actcaactag aagagaattt tagtacgcca tcacaaacat caacttcaac      1740
aaggattgga agtgattggt gggagacctt tttagatgac aaggatgcta ctgaaagaga      1800
tacaggttct ggtcttgggt tagatgaaga actgctcgca agtttttggg ttgatgatga      1860
tatgccacaa tcgacaagaa catgcgtcaa ttttctgaa gaaggattaa gtagaggtga      1920
tttctctttt agcgtggacc tttggaatca ttcaaaagaa gaatagctag              1970

<210> SEQ ID NO 36
<211> LENGTH: 729
```

```
<212> TYPE: DNA
<213> ORGANISM: Prunus persica

<400> SEQUENCE: 36
atggagggat ataacttggg tgtgagaaaa ggagcttgga ctagagagga agatgatctt      60
ttgaggcagt gcattgagaa tcatggagaa ggaaagtggc accaagttcc taacaaagca     120
gggttgaaca ggtgcaggaa gagctgtaga ctaaggtgga tgaactattt gaagccaaat     180
atcaagagag gagagtttgc agaggatgaa gtagatctaa tcattaggct tcacaagctt     240
ttaggaaaca ggtggtcatt gattgctgga aggcttccag gaaggacagc gaatgatgtg     300
aaaaattatt ggaacactcg actgcggacg gattctcgcc tgaaaaaggt gaaagataaa     360
ccccaagaaa caataaagac catcgtaata agacctcaac cccgaagctt catcaagagt     420
tcaaattgtt tgagcagtaa agaaccaatt ttggatcata ttcaaacagt cgagaatttt     480
agtacgccgt cacaaacatc accatcaaca aagaatggaa atgattggtg gaaacccttt     540
ttagatgacg aggatgtttt tgaaagagct acatgctatg gtctagcatt agaggaagaa     600
gagttcacaa gttttgggt tgatgatatg ccacaatcga aaagacagtg taccaatgtt     660
tcagaagaag gactaggtag aggtgatttc tcttttagcg tggacctttg aatcattca      720 aaagaagaa                                                             729

<210> SEQ ID NO 37
<211> LENGTH: 1920
<212> TYPE: DNA
<213> ORGANISM: Prunus persica

<400> SEQUENCE: 37
taagagatgg agggatataa cttgggtgtg agaaaaggag cttggactag agaggaagat      60
gatcttttga ggcagtgcat tgagaatcat ggagaaggaa agtggcacca agttcctaac     120
aaagcaggta ttaatgtaaa tataactcag agagatatat gatatagatg gttaataaat     180
agctagagct taattaatag gcagtgaagc cttaaattag tgatgtttac aaggccttaa     240
acttctccac ttattgccaa ttggttgctt ttaattttgt ctttcaacgg ctaggcccaa     300
tagtcactag tgctcccata ttactcatta tttatgttgt ccacgtgctt agctcaaatg     360
atatcactcg tgggccgagg ggtgctaaga gacttatcca acatctggaa ttttttgcat     420
tatgcatgga tgcagggttg aacaggtgca ggaagagctg tagactaagg tggatgaact     480
atttgaagcc aaatatcaag agaggagagt ttgcagagga tgaagtagat ctaatcatta     540
ggcttcacaa gcttttagga acaggtacc aataaatgtc tctttcctta tcccacatgg     600
ttctttcatc ataccatt caaaaaaacc taaaatccac aattgccgac atgcatcccg      660
tgttgttttc tatattatat cttctcttgt ttatctcagt acgcatgcac aaccacaaaa     720
aagcactaga agggccatga agccatgcat gatgtatctt agtctctgtg aatcgtaaaa     780
catagtgatc atatatgtta caacatctac aaaaagcttt ttatcacaac tagccctgag     840
gttttgcgaa attatcgtct ttcgtcttta atgtttttta tgtgatatta atggtcctta     900
aggttatcat ccacaaatca aaatggtctc tatcgtcagt ttccgttaaa ttttctatta     960
aaatgatgat gtggtatata tatgggggcaa cacatctaat aatatagtgc cacgtagctt    1020
taataaaaga tttaaatccc aacccggttc tttgcttgcc tgaccatcac cctcaaatct    1080
gatgagagag agtgagtgag tggagggagg tgggtgccac ggtggggcga caggtttgaa    1140
ggaagagggc gagagagttt ttttcaaaaa aagaaaatt taagtttaa tcttatcttt    1200 tttaaatata ttaatacttt atttaaaatc acgtggctat atattgttgg atgtgtggct    1260
```

```
cacatatatg ccatatcatc ttttaatag aaaatttgac ggaagttgac ggcagggttt    1320
gatttatttc ctactttgtg tgtgtgtatc atagcacaaa tgtattgatt tattttctca    1380
tgctatctgt cgaaggtggt cattgattgc tggaaggctt ccaggaagga cagcgaatga    1440
tgtgaaaaat tattggaaca ctcgactgcg gacggattct cgcctgaaaa aggtgaaaga    1500
taaaccccaa gaaacaataa agaccatcgt aataagacct caaccccgaa gcttcatcaa    1560
gagttcaaat tgtttgagca gtaaagaacc aattttggat catattcaaa cagtcgagaa    1620
ttttagtacg ccgtcacaaa catcaccatc aacaaagaat ggaaatgatt ggtgggaaac    1680 cttttttagat gacgaggatg ttttttgaaag agctacatgc tatggtctag cattagagga    1740
agaagagttc acaagttttt gggttgatga tatgccacaa tcgaaaagac agtgtaccaa    1800
tgtttcagaa gaaggactag gtagaggtga tttctctttt agcgtggacc tttggaatca    1860
ttcaaaagaa gaatagctag agaaaatgat tctcacttct gtggtaccat ctagcttgtg    1920
```

<210> SEQ ID NO 38
<211> LENGTH: 738
<212> TYPE: DNA
<213> ORGANISM: Eriobotrya japonica

<400> SEQUENCE: 38

```
atggagggat ataacgttaa cttgagggtg aagagaaaag gtgcctggac tcgagaggaa      60
gacaatcttc tcaggcagtg cattgagatt cttggagaag gaaagtggca ccaagttcct     120
tacaaagcag gcttaaacag gtgcaggaag agctgcagac taagatggtt gaactatgtg     180
aagccaaata tcaagagagg agactttaca gaggatgaag tagatcttat aattaggctt     240
cacaagcttt taggaaacag gtggtcgttg attgctggaa gacttcaagg aagaacagcg     300
aatgatgtga aaaattattg taacactcga ttacggatca attctcgcat gaaaacatcg     360
caaaataaat cccaagagac gagaaagacc attgtgatca gacctcaacc ccgaagtttc     420
ataaaaagtt cgaattactt gagcagcaaa gaaccaattt tggaccatat tcaatcagaa     480
gaggattcaa gtacgccatc acaaacatcg ttgacaaaga atggaaatga taggtgggag     540
accttgttaa aagacgaggg tactttttgaa agaactgcat atcccagctt tgagttagaa     600
gaagaactct tcacaagctt tgggctgat gaaatgcaac agtcggcaag atcatgtaca     660
gtcagttttc ctgaagaagg accaagtaaa agtaatttat cctttaacat ggagctttgg     720
aatcattcaa aagaagaa                                                    738
```

<210> SEQ ID NO 39
<211> LENGTH: 1570
<212> TYPE: DNA
<213> ORGANISM: Eriobotrya japonica

<400> SEQUENCE: 39

```
taagagatgg agggatataa cgttaacttg agggtgaaga gaaaaggtgc ctggactcga      60
gaggaagaca atcttctcag gcagtgcatt gagattcttg gagaaggaaa gtggcaccaa     120
gttccttaca aagcaggtat atatgttaat gtgtatatat aactgagaaa gatggatatg     180
tgtattgcta ggaaagcatt tcattagtat atttcattct aagaccttct gccaattggt     240
ttcaagttgg atgttatgct tttattaatg ctttagaaca tgctaacgcg tctaacagtt     300
acacatggcc cacgtcgaga gagttcgtcc cgcatcggaa acttcctcat gaaaacacat     360
tgcggacata tttgcagtac ataaatgtta taaattatgc attctgtgca tatgcaggct     420
taaacaggtg caggaagagc tgcagactaa gatggttgaa ctatgtgaag ccaaatatca     480
```

```
agagaggaga ctttacagag gatgaagtag atcttataat taggcttcac aagcttttag    540
gaaacaggta ctaattaata aataaacatc actttcaatt cctatcctag ccgaaggaca    600
ctccacatcg tcctcattat cgaacttgtt gatgcccta  attaatcgag cttatgctct    660
aagagtctct tcagtgtgcc aggaacatat gcacagttgt catatgtcat tatacaagtg    720
aatggacgct tgaaaaaaaa aaaagtttta tccacttgta taataacata tgatgtactg    780
ccctgtgttt caggcacatt gaaaatatct ccatgtttta ttattacttt cattacacag    840
tttagtaaat aaataaataa tttgatgtgg ataatcagtg aatggaccta accaaacaaa    900
gtaattcgtt cactccattt aattctaaaa aagaaaattg ttaatgcaat ctaacttctt    960 ttttttttctt tttttttttt tttgctttgt tcctcttatt tttcatccga agtattcatg   1020 atttttttt  cgtgtacgta ctcaggtggt cgttgattgc tggaagactt caaggaagaa   1080
cagcgaatga tgtgaaaaat tattgtaaca ctcgattacg gatcaattct cgcatgaaaa   1140
catcgcaaaa taaatcccaa gagacgagaa agaccattgt gatcagacct caaccccgaa   1200
gtttcataaa aagttcgaat tacttgagca gcaagaacc  aattttggac catattcaat   1260
cagaagagga ttcaagtacg ccatcacaaa catcgttgac aaagaatgga aatgataggt   1320
gggagacctt gttaaaagac gagggtactt ttgaaagaac tgcatatccc agctttgagt   1380
tagaagaaga actcttcaca agcttttggg ctgatgaaat gcaacagtcg gcaagatcat   1440
gtacagtcag ttttcctgaa gaaggaccaa gtaaaagtaa tttatccttt aacatggagc   1500
tttggaatca ttcaaaagaa gaatagctag agaaaatgat tctcacttct gtggtaccat   1560
ctagcttgtg                                                          1570

<210> SEQ ID NO 40
<211> LENGTH: 678
<212> TYPE: DNA
<213> ORGANISM: Prunus dulcis

<400> SEQUENCE: 40
atggagggat ataacttggg tgtgagaaaa ggagcttgga ctagagagga agatgatctt     60
ctgaggcagt gcattgagaa tcaaggtgaa ggaaagtggc accaagttcc ttacaaagca    120
gggttgaaga ggtgcaggaa gagctgtaga ctaaggtggg tgaactattt gaagccaaat    180
atcaagagag gagagtttgc agaggatgaa gtagatctaa tcattaggct tcacaagctt    240
ttaggaaaca ggtggtcatt gattgctgga aggcttccag gaaggacagc gaatgatgtg    300
aaaaattatt ggaacactcg actgcggacg gattctcgcc tgaaaaaggt gaaagataaa    360
ccccaagaaa caataaagac catcgtaata agacctcaac cccgaagatt caccaaaagt    420
tcaaattgtt tgagttttaa agaaccaatt ttggaccata ctcaacgtga ttggtgggag    480
acctttttag atgacaagga tgctactgaa agagctacag gttctggtct tgggttagat    540
gaagaactgc tcgcaagttt ttgggttgat gatgatatgc cacaatcgac aagaaaatgc    600
atcaattttt ctgaaggact aattagaggt gatttctctt ttagcgtgga cccttggaat    660
cattcaaaag aagaatag                                                 678

<210> SEQ ID NO 41
<211> LENGTH: 1806
<212> TYPE: DNA
<213> ORGANISM: Prunus dulcis

<400> SEQUENCE: 41
taagagatgg agggatataa cttgggtgtg agaaaggag  cttggactag agaggaagat     60
```

-continued

| | |
|---|---|
| gatcttctga ggcagtgcat tgagaatcaa ggtgaaggaa agtggcacca agttccttac | 120 |
| aaagcaggta ttgatgtgaa ataactcc aaaagagaga tagatatatg atatatatag | 180 |
| ctacagctta attaagtagt gaagcgttgt cttggtgttg tttcttaaca cacacaaaaa | 240 |
| cgacatcctg aacttctcca ctcattgtta attggttttc tgtacgtgtt ttgctcaagg | 300 |
| gatgtcatac ataaaaggac attttgatat gcatgctgta acaaagacaa aaacgaagtt | 360 |
| taaaacgcaa cctgataatt tgtgacaag ttttgtgata aaaactcaat ttttgcatta | 420 |
| tgcatggatg cagggttgaa gaggtgcagg aagagctgta gactaaggtg ggtgaactat | 480 |
| ttgaagccaa atatcaagag aggagagttt gcagaggatg aagtagatct aatcattagg | 540 |
| cttcacaagc ttttaggaaa caggtaccaa taaatgtctc tttccttatc ccacatggtt | 600 |
| ctttcatcac ataccattca aaaaaaccta aaatccacaa tcgccgacat gcatcccgtg | 660 |
| ttttctatat tatatcttct gttgtttatc tcagtacgca tgcacaacca caaaaaagca | 720 |
| ctagaagggc catgaagcca tgcatgatgt atcttagtct ctgtgaatcg taaaacatag | 780 |
| tgatcatata tgttacaaca tctacaaaaa gcttttttatc acaaatagcc ctgacgtttt | 840 |
| gcgaaattat cgtctttcgt ctttaatatt ttttatgtga tattaatgat tcttaaaatt | 900 |
| atccgtcaca aatcagaata ttctctatcg tcagtttccg tcaaattatt tattaaaata | 960 |
| atgatgtggt atatatttag ggcaacacat ctaataatat agtaccacgt agctttaata | 1020 |
| aaagatttaa atcccaaccc ggttctttgc ttgcctaacc atcaccatca aatctgatga | 1080 |
| gagagagtga gtgagtggag ggaggtgggt gccacggtga ggcgacaggt ttgaaggaag | 1140 |
| aggacgagag agttttttta aagttttaat cttatctttt ttaaatatat taatactta | 1200 |
| tttaaaatca tgtgactata tattattgaa tgtgtggccc acatatatgt catatcatct | 1260 |
| ttttaacaga aaatttcacg aaaattgacg gcagggtttg atttatttcc tacttttttgt | 1320 |
| gtgtgtgtat catagcacaa atgtattgat tattttctca tgctatctgt cgaaggtggt | 1380 |
| cattgattgc tggaaggctt ccaggaagga cagcgaatga tgtgaaaaat tattggaaca | 1440 |
| ctcgactgcg gacggattct cgcctgaaaa aggtgaaaga taaacccaa gaaacaataa | 1500 |
| agaccatcgt aataagacct caaccccgaa gattcaccaa aagttcaaat tgtttgagtt | 1560 |
| ttaaagaacc aattttggac catactcaac gtgattggtg ggagacctt ttagatgaca | 1620 |
| aggatgctac tgaaagagct acaggttctg gtcttgggtt agatgaagaa ctgctcgcaa | 1680 |
| gttttttgggt tgatgatgat atgccacaat cgacaagaaa atgcatcaat ttttctgaag | 1740 |
| gactaattag aggtgatttc tcttttagcg tggacccttg aatcattca aagaagaat | 1800 |
| agctag | 1806 |

<210> SEQ ID NO 42
<211> LENGTH: 735
<212> TYPE: DNA
<213> ORGANISM: Prunus avium

<400> SEQUENCE: 42

| | |
|---|---|
| atggaggat ataacttggg tgtgagaaaa ggagcttgga caagacagga agatgatctt | 60 |
| ctgaggcagt gcattgagaa tcaaggagaa ggaaagtggc accaagttcc ttacaaagca | 120 |
| gggttgaaca ggtgccggag gagctgtaga ctaaggtggt tgaactattt gaagccaaat | 180 |
| atcaagagag gagactttat ggaagatgaa gtagatctaa taattaggct tcacaagctt | 240 |
| ttaggaaaca ggtggtcatt gattgctcaa agacttccag gaaggactgc gaatgatgtg | 300 |
| aaaaattact ggaacacccg attgcggatg gattattccc tgaaaaagat gaaagacaaa | 360 |

| | |
|---|---|
| tcccaagaaa caataaagac catcataata aggccacaac caaggagctt caccaaaagt | 420 |
| tcaaattgtt tgagttttaa agaaccaatt ttggaccata ctcaactaga agagaatttt | 480 |
| agtacgccat cacaaacatc aacatcaaca aggattggaa gtgattggtg ggagaccttt | 540 |
| ttagatgaca aggatgctac tgaaagagct acaggttctg gtcttgggtt agatgaagaa | 600 |
| ttgctcgcaa gtttttgggt tgatgatgat atgccacaat cgacaagaac gtgcatcaat | 660 |
| ttttctgaag aaggactaag tagaggtgat ttctctttta gcgtggacct ttggaatcat | 720 |
| tcaaaagaag aatag | 735 |

<210> SEQ ID NO 43
<211> LENGTH: 2262
<212> TYPE: DNA
<213> ORGANISM: Prunus avium

<400> SEQUENCE: 43

| | |
|---|---|
| taagagatgg agggatataa cttgggtgtg agaaaaggag cttggacaag acaggaagat | 60 |
| gatcttctga ggcagtgcat tgagaatcaa ggagaaggaa agtggcacca agttccttac | 120 |
| aaagcaggta ttaatgtgaa atataactcc aaaagagata gatatatggt atatatagct | 180 |
| acagcttaat taagtagtga agcgttgtct tagtgttgtt tcttagcaca cacaaaaacg | 240 |
| acatcctgaa cttctccact cattgttaat tggttttctg tacgtgttct gctcaaggga | 300 |
| tgtcatacat aaaaaggcca ttttgatatc caacattggg aacttcctca agaaaacaca | 360 |
| ttgtagatat gcatgatata acaaagacaa aaacgaagtt taagacgcag cctgataatt | 420 |
| tcatgacaag ttttgtgata aaaactcaat ttttctgcat tatgcatgga tgcagggttg | 480 |
| aacaggtgcc ggaggagctg tagactaagg tggttgaact atttgaagcc aaatatcaag | 540 |
| agaggagact ttatggaaga tgaagtagat ctaataatta ggcttcacaa gcttttagga | 600 |
| aacaggtacc aatatataaa tgtctctttc ttcgctgtca acctccacat ccacttattt | 660 |
| tgtccttaat taattgagct cataacacac atggtcatgg tgttgccgtt ggttgaaccc | 720 |
| tagcccccaa aaacaaaaca aaaatacaaa atacgaacat gtgccagcat atcccgtgct | 780 |
| ttttttatttt attttatttt gtctcagaag gacaaaacat gttggcagct tctcataccc | 840 |
| tctctgcaaa gataaacatt aaaattcccg ttgaaatctc attatacttt cagctagtca | 900 |
| tacaagaaac attacttcgg aaatatttaa ttttatcat tttttaattt cttagtactt | 960 |
| tggttaatgt atattaagtg gagagttttt ctatgttaca agaaaaaaa aaatcataca | 1020 |
| gtataattat tggggtatta aagcgtggca caataatatt gtctccctaa cattattgtt | 1080 |
| tcccatacct agcaaaaatt aaattaatat atccatccat aggaaattta tttgctcttt | 1140 |
| gttttcttgg ctgaaatttt atacctatgt tgggctcctt ttccttttac tttattcatc | 1200 |
| tttgttatta gtaaaatctt tcaaacacaa actagcatac aaggagttgg ctcccctttga | 1260 |
| catagtttgg agctctaaag aggggaagat gtttggttgc gttgggttcg ggtttagcca | 1320 |
| gtacgggact atgggtttgg cttagaagat gtggagcggt ggtcttatat ttctttattt | 1380 |
| tgttttagac taataatttt caaaaactct ttaccagttt gctgtgatt gttttctttt | 1440 |
| tttaaaaaaa aaaattcttt ttagcttttg gttttaata cgaatttgcc gtttctacca | 1500 |
| tttgcacgtc gaatttgtat tgtatgtctg agtacatgtg cttctggttg ctgaatgggg | 1560 |
| gatttagtca ttatttggat tgtgtgtgat tctctctaga tcaattcaat atgttgttgt | 1620 |
| gtttggtcac tggagaagat ttactcatat tcggcacata attgttttgt acttttattt | 1680 |
| gttcatcaat aatatactgt cgcttatttt caacccaaaa aaaaaaaat aataacatac | 1740 |

```
aaatgtatta actttctcat gctatgtgtg gaaggtggtc attgattgct caaagacttc    1800
caggaaggac tgcgaatgat gtgaaaaatt actggaacac ccgattgcgg atggattatt    1860
ccctgaaaaa gatgaaagac aaatcccaag aaacaataaa gaccatcata taaggccac     1920 aaccaaggag cttcaccaaa agttcaaatt gtttgagttt aaagaaccaa attttggacc    1980
atactcaact agaagagaat tttagtacgc catcacaaac atcaacatca acaaggattg    2040
gaagtgattg gtgggagacc tttttagatg acaaggatgc tactgaaaga gctacaggtt    2100
ctggtcttgg gttagatgaa gaattgctcg caagtttttg ggttgatgat gatatgccac    2160
aatcgacaag aacgtgcatc aattttttctg aagaaggact aagtagaggt gatttctctt    2220
ttagcgtgga cctttggaat cattcaaaag aagaatagct ag                        2262

<210> SEQ ID NO 44
<211> LENGTH: 744
<212> TYPE: DNA
<213> ORGANISM: Mespilus germanica

<400> SEQUENCE: 44 atggaggat ataacgttaa cttgagtgtg agaaaaggtg cctggactcg agaggaagac      60
aatcttctca ggcagtgcat tgagattcat ggagagggaa agtggaacca agtttcatac    120
aaagcaggct taaacaggtg caggaagagc tgcagactaa gatggttaaa ctacctgaag    180
ccaagtatca agagaggga ctttaaagag gatgaagtag atcttataat tagacttcac     240
aagcttttag gaaacaggtg gtcattgatt gctcaaagac ttccaggaag gactgcgaat    300
gatgtgaaaa attactggaa cacccgattg cggatggatt attccctgaa aaagatgaaa    360
gacaaatccc aagaaacaat aaagaccatc ataataaggc cacaaccaag gagcttcacc    420
aaaagttcaa attgtttgag ttttaaagaa ccaatttttgg accatactca actagaagag    480
aattttagta cgccatcaca acatcaaca tcaacaagga ttggaagtga ttggtgggag      540
acctttttag atgacaagga tgctactgaa agagctacag gttctggtct tgggttagat     600
gaagaattgc tcgcaagttt ttgggttgat gatgatatgc cacaatcgac aagaacgtgc    660
atcaattttt ctgaagaagg actaagtaga ggtgaattat cctttagcac ggacctttgg    720
aatcattcaa agaagaatag ctag                                           744

<210> SEQ ID NO 45
<211> LENGTH: 2287
<212> TYPE: DNA
<213> ORGANISM: Mespilus germanica

<400> SEQUENCE: 45
taagagatgg agggatataa cgttaacttg agtgtgagaa aaggtgcctg gactcgagag     60
gaagacaatc ttctcaggca gtgcattgag attcatggag agggaaagtg gaaccaagtt    120
tcatacaaag caggtatata tgttaatgat gtgtatattt aactgtgaaa gatgtatatg    180
tgtattattt taaagcattt cactagtatt tcattctaag accttttgtt aattagtttc     240
aagttgaatg tttttacttt tattagtgttt tagaacatgt taatgtgtct aacggccata    300
cctgccctca cctcactaat ctatggtgtt tacatatatg ctaaaatga cctttgcgtg      360 tgtgagcagg gccatgttga gagacttagt cctttacaag tatgtgttgt tcacgtagaa    420
agatgttata tgaatataaa ctttgaatta tgtatgcagg cttaaacagg tgcaggaaga    480
gctgcagact aagatggtta aactacctga agccaagtat caagagaggg gactttaaag    540
aggatgaagt agatcttata attagacttc acaagctttt aggaaacagg taccaatata    600
```

```
taaatgtctc tttcttcgct gtcaacctcc acatccactt attttgtcct taattaattg    660
agctcataac acacatggtc atggtgttgc cgttggttga accctagccc ccaaaaacaa    720
aacaaaaata caaaatacga acatgtgcca gcatatcccg tgctttttta ttttatttta    780
ttttgtctca gaaggacaaa acatgttggc agcttctcat accctctctg caaagataaa    840
cattaaaatt cccgttgaaa tctcattata ctttcagcta gtcatacaag aaacattact    900
tcggaaatat ttaattttta tcatttttta atttcttagt actttggtta atgtatatta    960
agtggagagt ttttctatgt tacaaagaaa aaaaaaatca tacagtataa ttattgggt    1020 attaaagcgt ggcacaataa tattgtctcc ctaacattat tgtttcccat acctagcaaa    1080
aattaaatta atatatccat ccataggaaa tttatttgct ctttgttttc ttggctgaaa    1140
ttttatacct atgttgggct cctttccctt ttactttatt catctttgtt attagtaaaa    1200
tctttcaaac acaaactagc atacaaggag ttggctccct ttgacatagt ttggagctct    1260
aaagagggga agatgtttgg ttgcgttggg ttcgggttta gccagtacgg gactatgggt    1320
ttggcttaga agatgtggag cggtggtctt atatttcttt attttgtttt agactaataa    1380
ttttcaaaaa ctcttacca gtttgctgtg atttgttttc ttttttaaaa aaaaaaattc    1440
tttttagctt ttggttttta atacgaattt gccgtttcta ccatttgcac gtcgaatttg    1500
tattgtatgt ctgagtacat gtgcttctgg ttgctgaatg ggggatttag tcattatttg    1560
gattgtgtgt gattctctct agatcaattc aatatgttgt tgtgtttggt cactggagaa    1620
gatttactca tattccggcac ataattgttt tgtactttta tttgttcatc aataatatac    1680
tgtcgcttat tttcaaccca aaaaaaaaaa aataataaca tacaaatgta ttaactttct    1740
catgctatgt gtggaaggtg gtcattgatt gctcaaagac ttccaggaag gactgcgaat    1800
gatgtgaaaa attactggaa cacccgattg cggatggatt attccctgaa aaagatgaaa    1860
gacaaatccc aagaaacaat aaagaccatc ataataaggc cacaaccaag gagcttcacc    1920
aaaagttcaa attgtttgag ttttaaagaa ccaattttgg accatactca actagaagag    1980
aattttagta cgccatcaca aacatcaaca tcaacaagga ttggaagtga ttggtgggag    2040 accttttag atgacaagga tgctactgaa agagctacag gttctggtct tgggttagat    2100
gaagaattgc tcgcaagttt ttgggttgat gatgatatgc cacaatcgac aagaacgtgc    2160
atcaattttt ctgaagaagg actaagtaga ggtgaattat cctttagcac ggacctttgg    2220
aatcattcaa agaagaatag ctagagaaaa tgattctcac ttctgtggta ccatctagct    2280
tgtgtaa                                                              2287
```

<210> SEQ ID NO 46
<211> LENGTH: 714
<212> TYPE: DNA
<213> ORGANISM: Prunus domestica

<400> SEQUENCE: 46

```
atggagggat ataacgtggg tgtgagaaaa ggagcttgga ctagagagga agatgatctt     60
ttgaggcagt gcattgagaa tcatggagaa ggaaagtggc accaagttcc taacaaagca    120
gggttgaaca ggtgcaggaa gagctgtaga ctaaggtggt tgaactattt gaagccaaat    180
atcaagagag gagagtttgc agaggatgaa gtagatctaa taattaggct tcacaagctt    240
ttaggaaaca ggtggtcatt gattgctgga aggcttccag ggaggacagc gaatgatgtg    300
aaaaattatt ggaacactcg actgcgaaag gtgaaagata aaccccaaga acaataaag    360 accatcgtaa taagacctca accccgaagc ttcatcaaga gttcaaattg tttgagcagt    420
```

```
aaagaaccaa ttttggacca tattcaaaca gtcgagaatt ttagtacgcc gtcacaatca    480
tcaccatcaa caaagaacgg aaatgattgg tgggaaacct ttttagatga cgaggatgtt    540
tttgaaaaag ctacatgcta tggtctagcg ttagaggaag aagagttcac aagttttggg   600
gttgatgata tgccacaatc gaaaagacag tgtaccaatg ttacagaaga aggactaggt    660
acaggtgatt tctcttttaa cgtggaccct tggaatcatt caaagaaga atag           714
```

<210> SEQ ID NO 47
<211> LENGTH: 1916
<212> TYPE: DNA
<213> ORGANISM: Prunus domestica
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t

<400> SEQUENCE: 47

```
taagagatgg agggatataa cgtgggtgtg agaaaggag cttggactag agaggaagat      60
gatcttttga ggcagtgcat tgagaatcat ggagaaggaa agtggcacca agttcctaac    120
aaagcaggta ttaatgtaaa tataactcag agagatatat gatatataga tggttaataa    180
aaagctagag cttaattaat aggcagtgaa gccttaaatt agtgatgttt acaaggcctt    240
aaacttctcc acttattccc aattggttgc ttttgatttt atgttcact ggctaggccc    300 aatagtcact agtgctccca tattactcac tatttatgtt gtctatgtgt ttagctcaaa    360
tgatattgct cttgagccga ggggtgctaa gagacttatc ccacatcggg aattttttgc    420
attatgcatg gatgcagggt tgaacaggtg caggaagagc tgtagactaa ggtggttgaa    480
ctatttgaag ccaaatatca agagaggaga gtttgcagag gatgaagtag atctaataat    540
taggcttcac aagcttttag gaaacaggta ccaataaacg tctctttcct tatcccatat    600
ggctctttca tcacatacca ttaaaaaaaa aaaaaactaa atccacaat cgccgacatg    660 tatcctgtgt tgtttttctat attatatctt ctgttgttta tctcagtacg catgcacaac    720
cacaaaaagc actagaaggg ccatgtaagc atgcacgatg tatcttagtc tctgtgaatc    780
gtaaaatata gtgatcatat atgttagaac atttacagaa grwtttatc acaaatagtc    840 ctgaggttna taaatnatc gtctttngtc tttaatatat atattatttt atttttttg    900 tgatactaat ggtcttttaag tttatccttc acacatcaaa atggtctccg tcgtcaattt    960
ccgtcaaatt ttctgttaaa atgctgatgt ggcatatatg tagggccaca catctaataa   1020
tatagtgcca catagcttta ataaaagatt taaatcccga cctggttctt tgcttgcctg   1080
accatcatcc tcaaatctga tgtgagagag agagagagag agagagagag agagagagaa   1140
agagagaggg ntggagggan ggtgggggtgc cacggtgggg cgacaggttt gaaggaagag   1200
gacgagagag agttttttttt aaaaaaaaaa tttaagtttt aatcttatct tttttaaata   1260
```

-continued

```
tattaacatt ttatttaaaa ccacgtggct atatattatt ggatttgtgg cccacatata    1320
tgctatatca tctttttaac agaaaatttg acggaagttg acggcagggt ttgatttatt    1380
ttcttctttt tttgcgtctg tatcataaca caaatgtatt gatttatttt ctcatgctat    1440
ctgtcgaagg tggtcattga ttgctggaag gcttccaggg aggacagcga atgatgtgaa    1500
aaattattgg aacactcgac tgcgaaaggt gaaagataaa ccccaagaaa caataaagac    1560
catcgtaata agacctcaac cccgaagctt catcaagagt tcaaattgtt tgagcagtaa    1620
agaaccaatt ttggaccata ttcaaacagt cgagaatttt agtacgccgt cacaatcatc    1680
accatcaaca aagaacggaa atgattggtg ggaaaccttt ttagatgacg aggatgtttt    1740
tgaaaaagct acatgctatg gtctagcgtt agaggaagaa gagttcacaa gttttttgggt   1800 tgatgatatg ccacaatcga aaagacagtg taccaatgtt acagaagaag gactaggtac    1860
aggtgatttc tcttttaacg tggaccttttg gaatcattca aaagaagaat agctag       1916
```

<210> SEQ ID NO 48
<211> LENGTH: 38
<212> TYPE: DNA
<213> ORGANISM: Artificial
<220> FEATURE:
<223> OTHER INFORMATION: Synthetic construct useful as a primer

<400> SEQUENCE: 48

```
aaaagttgca gacttagatg gttgaattat ttgaagcc                              38
```

<210> SEQ ID NO 49
<211> LENGTH: 27
<212> TYPE: DNA
<213> ORGANISM: Artificial
<220> FEATURE:
<223> OTHER INFORMATION: Synthetic construct useful as a primer

<400> SEQUENCE: 49

```
gagaatcgat ccgcaatcga gtgttcc                                          27
```

<210> SEQ ID NO 50
<211> LENGTH: 31
<212> TYPE: DNA
<213> ORGANISM: Artificial
<220> FEATURE:
<223> OTHER INFORMATION: Synthetic construct useful as a primer

<400> SEQUENCE: 50

```
accacctgtt tcccaaaagc ctgtgaagtc t                                     31
```

<210> SEQ ID NO 51
<211> LENGTH: 33
<212> TYPE: DNA
<213> ORGANISM: Artificial
<220> FEATURE:
<223> OTHER INFORMATION: Synthetic construct useful as a primer

<400> SEQUENCE: 51

```
cacaagctag atggtaccac agaagtgaga atc                                   33
```

<210> SEQ ID NO 52
<211> LENGTH: 22
<212> TYPE: DNA
<213> ORGANISM: Artificial
<220> FEATURE:
<223> OTHER INFORMATION: Synthetic construct useful as a primer

<400> SEQUENCE: 52
taagagatgg agggatataa cg    22

<210> SEQ ID NO 53
<211> LENGTH: 26
<212> TYPE: DNA
<213> ORGANISM: Artificial
<220> FEATURE:
<223> OTHER INFORMATION: Synthetic construct useful as a primer

<400> SEQUENCE: 53
ctagctattc ttcttttgaa tgattc    26

<210> SEQ ID NO 54
<211> LENGTH: 24
<212> TYPE: DNA
<213> ORGANISM: Artificial
<220> FEATURE:
<223> OTHER INFORMATION: Synthetic construct useful as a primer

<400> SEQUENCE: 54
gatcgattct cgcatgaaaa cggt    24

<210> SEQ ID NO 55
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 55
gacgacgttt gtggtggcgt act    23

<210> SEQ ID NO 56
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 56
tgcctggact cgagaggaag aca    23

<210> SEQ ID NO 57
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 57
cctgtttccc aaaagcctgt gaa    23

<210> SEQ ID NO 58
<211> LENGTH: 22
<212> TYPE: DNA
<213> ORGANISM: Artificial
<220> FEATURE:
<223> OTHER INFORMATION: Synthetic construct useful as a primer

<400> SEQUENCE: 58
cttataatta gacttcacag gc    22

<210> SEQ ID NO 59
<211> LENGTH: 20
<212> TYPE: DNA
<213> ORGANISM: Artificial

```
<220> FEATURE:
<223> OTHER INFORMATION: Synthetic construct useful as a primer

<400> SEQUENCE: 59
caccgttttc atgcgagaat                                                    20

<210> SEQ ID NO 60
<211> LENGTH: 37
<212> TYPE: DNA
<213> ORGANISM: Artificial
<220> FEATURE:
<223> OTHER INFORMATION: Synthetic construct useful as a primer

<400> SEQUENCE: 60
gcagataaga gatggaggga tataacgaaa acctgag                                 37

<210> SEQ ID NO 61
<211> LENGTH: 35
<212> TYPE: DNA
<213> ORGANISM: Artificial
<220> FEATURE:
<223> OTHER INFORMATION: Synthetic construct useful as a primer

<400> SEQUENCE: 61
tacacaagct agatggtacc acagaagtga gaatc                                   35

<210> SEQ ID NO 62
<211> LENGTH: 25
<212> TYPE: DNA
<213> ORGANISM: Artificial
<220> FEATURE:
<223> OTHER INFORMATION: Synthetic construct useful as a primer

<400> SEQUENCE: 62
gactttatgg aagatgaagt agatc                                              25

<210> SEQ ID NO 63
<211> LENGTH: 25
<212> TYPE: DNA
<213> ORGANISM: Artificial
<220> FEATURE:
<223> OTHER INFORMATION: Synthetic construct useful as a primer

<400> SEQUENCE: 63
aagcgatagt atattattga tgaac                                              25

<210> SEQ ID NO 64
<211> LENGTH: 20
<212> TYPE: DNA
<213> ORGANISM: Artificial
<220> FEATURE:
<223> OTHER INFORMATION: Synthetic construct useful as a primer

<400> SEQUENCE: 64
cttgggtgtg agaaaaggag                                                    20

<210> SEQ ID NO 65
<211> LENGTH: 20
<212> TYPE: DNA
<213> ORGANISM: Artificial
<220> FEATURE:
<223> OTHER INFORMATION: Synthetic construct useful as a primer

<400> SEQUENCE: 65
cacgctaaaa gagaaatcac                                                    20
```

```
<210> SEQ ID NO 66
<211> LENGTH: 20
<212> TYPE: DNA
<213> ORGANISM: Artificial
<220> FEATURE:
<223> OTHER INFORMATION: Synthetic construct useful as a primer

<400> SEQUENCE: 66
gcttgtgaag cctaattatt                                              20

<210> SEQ ID NO 67
<211> LENGTH: 20
<212> TYPE: DNA
<213> ORGANISM: Artificial
<220> FEATURE:
<223> OTHER INFORMATION: Synthetic construct useful as a primer

<400> SEQUENCE: 67
gaaagataaa ccccaagaaa                                              20

<210> SEQ ID NO 68
<211> LENGTH: 20
<212> TYPE: DNA
<213> ORGANISM: Artificial
<220> FEATURE:
<223> OTHER INFORMATION: Synthetic construct useful as a primer

<400> SEQUENCE: 68
tttgaactct tgatgaagct                                              20

<210> SEQ ID NO 69
<211> LENGTH: 22
<212> TYPE: DNA
<213> ORGANISM: Artificial
<220> FEATURE:
<223> OTHER INFORMATION: Synthetic construct useful as a primer

<400> SEQUENCE: 69
ctgcgaattt gtattgtatg tc                                           22

<210> SEQ ID NO 70
<211> LENGTH: 20
<212> TYPE: DNA
<213> ORGANISM: Artificial
<220> FEATURE:
<223> OTHER INFORMATION: Synthetic construct useful as a primer

<400> SEQUENCE: 70
ttcccaccaa tcatttccat                                              20

<210> SEQ ID NO 71
<211> LENGTH: 22
<212> TYPE: DNA
<213> ORGANISM: Artificial
<220> FEATURE:
<223> OTHER INFORMATION: Synthetic construct useful as a primer

<400> SEQUENCE: 71
aagagaggag agtttgcaga gg                                           22

<210> SEQ ID NO 72
<211> LENGTH: 22
<212> TYPE: DNA
<213> ORGANISM: Artificial
<220> FEATURE:
<223> OTHER INFORMATION: Synthetic construct useful as a primer

<400> SEQUENCE: 72
```

```
tagttcttca catcattggc ag                                              22

<210> SEQ ID NO 73
<211> LENGTH: 25
<212> TYPE: DNA
<213> ORGANISM: Artificial
<220> FEATURE:
<223> OTHER INFORMATION: Synthetic construct useful as a primer

<400> SEQUENCE: 73
aatatgcacc aggaagtctt aaaga                                           25

<210> SEQ ID NO 74
<211> LENGTH: 25
<212> TYPE: DNA
<213> ORGANISM: Artificial
<220> FEATURE:
<223> OTHER INFORMATION: Synthetic construct useful as a primer

<400> SEQUENCE: 74
aaatctgctt aattttcatg gaggg                                           25

<210> SEQ ID NO 75
<211> LENGTH: 28
<212> TYPE: DNA
<213> ORGANISM: Artificial
<220> FEATURE:
<223> OTHER INFORMATION: Synthetic construct useful as a primer

<400> SEQUENCE: 75
tcagagagag agagatgggt ggtattcc                                        28

<210> SEQ ID NO 76
<211> LENGTH: 26
<212> TYPE: DNA
<213> ORGANISM: Artificial
<220> FEATURE:
<223> OTHER INFORMATION: Synthetic construct useful as a primer

<400> SEQUENCE: 76
cttcctcttg ttcaaagctc cctctc                                          26

<210> SEQ ID NO 77
<211> LENGTH: 25
<212> TYPE: DNA
<213> ORGANISM: Artificial
<220> FEATURE:
<223> OTHER INFORMATION: Synthetic construct useful as a primer

<400> SEQUENCE: 77
agaactattg gaattgtcac ttgag                                           25

<210> SEQ ID NO 78
<211> LENGTH: 25
<212> TYPE: DNA
<213> ORGANISM: Artificial
<220> FEATURE:
<223> OTHER INFORMATION: Synthetic construct useful as a primer

<400> SEQUENCE: 78
agaataaaat cactttcata accac                                           25

<210> SEQ ID NO 79
<211> LENGTH: 30
<212> TYPE: DNA
<213> ORGANISM: Artificial
```

```
<220> FEATURE:
<223> OTHER INFORMATION: Synthetic construct useful as a primer
<220> FEATURE:
<221> NAME/KEY: misc_feature
<222> LOCATION: (21)..(21)
<223> OTHER INFORMATION: n is a, c, g, or t

<400> SEQUENCE: 79
agacttccrg gaagracwgc naatgmtgtg                                         30

<210> SEQ ID NO 80
<211> LENGTH: 24
<212> TYPE: DNA
<213> ORGANISM: Artificial
<220> FEATURE:
<223> OTHER INFORMATION: Synthetic construct useful as a primer
<220> FEATURE:
<221> NAME/KEY: misc_feature
<222> LOCATION: (22)..(22)
<223> OTHER INFORMATION: n is a, c, g, or t

<400> SEQUENCE: 80
ccartaattt ttcacakcat tngc                                              24

<210> SEQ ID NO 81
<211> LENGTH: 25
<212> TYPE: DNA
<213> ORGANISM: Artificial
<220> FEATURE:
<223> OTHER INFORMATION: Synthetic construct useful as a primer

<400> SEQUENCE: 81
ggagacaact ggagaaggac tggaa                                             25

<210> SEQ ID NO 82
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 82
cgacattgat actggtgtct tca                                               23

<210> SEQ ID NO 83
<211> LENGTH: 20
<212> TYPE: DNA
<213> ORGANISM: Artificial
<220> FEATURE:
<223> OTHER INFORMATION: Synthetic construct useful as a primer

<400> SEQUENCE: 83
gggataacct cgcggccaaa                                                   20

<210> SEQ ID NO 84
<211> LENGTH: 22
<212> TYPE: DNA
<213> ORGANISM: Artificial
<220> FEATURE:
<223> OTHER INFORMATION: Synthetic construct useful as a primer

<400> SEQUENCE: 84
gcatccatgc cggaagctac aa                                                22

<210> SEQ ID NO 85
<211> LENGTH: 23
<212> TYPE: DNA
<213> ORGANISM: Artificial
```

```
<220> FEATURE:
<223> OTHER INFORMATION: Synthetic construct useful as a primer

<400> SEQUENCE: 85
tggaagcttg tgaggactgg ggt                                              23

<210> SEQ ID NO 86
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 86
ctcctccgat ggcaaatcaa aga                                              23

<210> SEQ ID NO 87
<211> LENGTH: 21
<212> TYPE: DNA
<213> ORGANISM: Artificial
<220> FEATURE:
<223> OTHER INFORMATION: Synthetic construct useful as a primer

<400> SEQUENCE: 87
gatagggttt gagttcaagt a                                                21

<210> SEQ ID NO 88
<211> LENGTH: 24
<212> TYPE: DNA
<213> ORGANISM: Artificial
<220> FEATURE:
<223> OTHER INFORMATION: Synthetic construct useful as a primer

<400> SEQUENCE: 88
tctcctcagc agcctcagtt ttct                                             24

<210> SEQ ID NO 89
<211> LENGTH: 21
<212> TYPE: DNA
<213> ORGANISM: Artificial
<220> FEATURE:
<223> OTHER INFORMATION: Synthetic construct useful as a primer

<400> SEQUENCE: 89
ccaagtgaag cgggttgtgc t                                                21

<210> SEQ ID NO 90
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 90
caaagcaggc ggacaggagt agc                                              23

<210> SEQ ID NO 91
<211> LENGTH: 22
<212> TYPE: DNA
<213> ORGANISM: Artificial
<220> FEATURE:
<223> OTHER INFORMATION: Synthetic construct useful as a primer

<400> SEQUENCE: 91
ccaccgccct tccaaacact ct                                               22
```

```
<210> SEQ ID NO 92
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 92
cacccttatg ttacgcggca tgt                                              23

<210> SEQ ID NO 93
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 93
tgcctggact cgagaggaag aca                                              23

<210> SEQ ID NO 94
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 94
cctgtttccc aaaagcctgt gaa                                              23

<210> SEQ ID NO 95
<211> LENGTH: 23
<212> TYPE: DNA
<213> ORGANISM: Artificial
<220> FEATURE:
<223> OTHER INFORMATION: Synthetic construct useful as a primer

<400> SEQUENCE: 95 atgttttgc gacggagaga gca                                               23

<210> SEQ ID NO 96
<211> LENGTH: 28
<212> TYPE: DNA
<213> ORGANISM: Artificial
<220> FEATURE:
<223> OTHER INFORMATION: Synthetic construct useful as a primer

<400> SEQUENCE: 96
taggcgagtg aacaccatac attaaagg                                         28

<210> SEQ ID NO 97
<211> LENGTH: 22
<212> TYPE: DNA
<213> ORGANISM: Artificial
<220> FEATURE:
<223> OTHER INFORMATION: Synthetic construct useful as a primer

<400> SEQUENCE: 97
agggttccag aagaccacgc ct                                               22

<210> SEQ ID NO 98
<211> LENGTH: 22
<212> TYPE: DNA
<213> ORGANISM: Artificial
<220> FEATURE:
<223> OTHER INFORMATION: Synthetic construct useful as a primer

<400> SEQUENCE: 98
```
ttggatgtgg agtgctcgga ga                                           22

<210> SEQ ID NO 99
<211> LENGTH: 25
<212> TYPE: DNA
<213> ORGANISM: Artificial
<220> FEATURE:
<223> OTHER INFORMATION: Synthetic construct useful as a primer

<400> SEQUENCE: 99
tgaccgaatg agcaaggaaa ttact                                        25

<210> SEQ ID NO 100
<211> LENGTH: 24
<212> TYPE: DNA
<213> ORGANISM: Artificial
<220> FEATURE:
<223> OTHER INFORMATION: Synthetic construct useful as a primer

<400> SEQUENCE: 100
tactcagctt tggcaatcca catc                                         24

<210> SEQ ID NO 101
<211> LENGTH: 249
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: V, L OR E
<220> FEATURE:
<221> NAME/KEY: MISC_FEATURE
<222> LOCATION: (7)..(7)
<223> OTHER INFORMATION: N OR G
<220> FEATURE:
<221> NAME/KEY: MISC_FEATURE
<222> LOCATION: (8)..(8)
<223> OTHER INFORMATION: L OR V
<220> FEATURE:
<221> NAME/KEY: MISC_FEATURE
<222> LOCATION: (9)..(9)
<223> OTHER INFORMATION: R OR S
<220> FEATURE:
<221> NAME/KEY: MISC_FEATURE
<222> LOCATION: (10)..(10)
<223> OTHER INFORMATION: V OR K
<220> FEATURE:
<221> NAME/KEY: MISC_FEATURE
<222> LOCATION: (11)..(11)
<223> OTHER INFORMATION: G, R, K OR M
<220> FEATURE:
<221> NAME/KEY: MISC_FEATURE
<222> LOCATION: (12)..(12)
<223> OTHER INFORMATION: R OR IS ABSENT
<220> FEATURE:
<221> NAME/KEY: MISC_FEATURE
<222> LOCATION: (13)..(13)
<223> OTHER INFORMATION: K OR IS ABSENT
<220> FEATURE:
<221> NAME/KEY: MISC_FEATURE
<222> LOCATION: (14)..(14)
<223> OTHER INFORMATION: G OR IS ABSENT
<220> FEATURE:
<221> NAME/KEY: MISC_FEATURE
<222> LOCATION: (19)..(19)
<223> OTHER INFORMATION: E, K OR Q
<220> FEATURE:
<221> NAME/KEY: MISC_FEATURE
<222> LOCATION: (22)..(22)
<223> OTHER INFORMATION: D OR N
<220> FEATURE:
<221> NAME/KEY: MISC_FEATURE

```
<222> LOCATION: (28)..(28)
<223> OTHER INFORMATION: I OR V
<220> FEATURE:
<221> NAME/KEY: MISC_FEATURE
<222> LOCATION: (29)..(29)
<223> OTHER INFORMATION: E OR G
<220> FEATURE:
<221> NAME/KEY: MISC_FEATURE
<222> LOCATION: (30)..(30)
<223> OTHER INFORMATION: I, H OR N
<220> FEATURE:
<221> NAME/KEY: MISC_FEATURE
<222> LOCATION: (30)..(30)
<223> OTHER INFORMATION: I, N OR K
<220> FEATURE:
<221> NAME/KEY: MISC_FEATURE
<222> LOCATION: (31)..(31)
<223> OTHER INFORMATION: H, L OR Q
<220> FEATURE:
<221> NAME/KEY: MISC_FEATURE
<222> LOCATION: (37)..(37)
<223> OTHER INFORMATION: H OR N
<220> FEATURE:
<221> NAME/KEY: MISC_FEATURE
<222> LOCATION: (40)..(40)
<223> OTHER INFORMATION: P OR S
<220> FEATURE:
<221> NAME/KEY: MISC_FEATURE
<222> LOCATION: (41)..(41)
<223> OTHER INFORMATION: Y OR N
<220> FEATURE:
<221> NAME/KEY: MISC_FEATURE
<222> LOCATION: (43)..(43)
<223> OTHER INFORMATION: A OR T
<220> FEATURE:
<221> NAME/KEY: MISC_FEATURE
<222> LOCATION: (46)..(46)
<223> OTHER INFORMATION: N, S OR K
<220> FEATURE:
<221> NAME/KEY: MISC_FEATURE
<222> LOCATION: (50)..(50)
<223> OTHER INFORMATION: K OR R
<220> FEATURE:
<221> NAME/KEY: MISC_FEATURE
<222> LOCATION: (54)..(54)
<223> OTHER INFORMATION: L OR Q
<220> FEATURE:
<221> NAME/KEY: MISC_FEATURE
<222> LOCATION: (57)..(57)
<223> OTHER INFORMATION: L, M OR V
<220> FEATURE:
<221> NAME/KEY: MISC_FEATURE
<222> LOCATION: (60)..(60)
<223> OTHER INFORMATION: L OR V
<220> FEATURE:
<221> NAME/KEY: MISC_FEATURE
<222> LOCATION: (63)..(63)
<223> OTHER INFORMATION: N OR S
<220> FEATURE:
<221> NAME/KEY: MISC_FEATURE
<222> LOCATION: (68)..(68)
<223> OTHER INFORMATION: D OR E
<220> FEATURE:
<221> NAME/KEY: MISC_FEATURE
<222> LOCATION: (70)..(70)
<223> OTHER INFORMATION: K, A, M OR T
<220> FEATURE:
<221> NAME/KEY: MISC_FEATURE
<222> LOCATION: (78)..(78)
<223> OTHER INFORMATION: I OR L
<220> FEATURE:
<221> NAME/KEY: MISC_FEATURE
<222> LOCATION: (82)..(82)
<223> OTHER INFORMATION: K OR R
<220> FEATURE:
<221> NAME/KEY: MISC_FEATURE
<222> LOCATION: (93)..(93)
<223> OTHER INFORMATION: R, G OR Q
<220> FEATURE:
<221> NAME/KEY: MISC_FEATURE
```

```
<222> LOCATION: (96)..(96)
<223> OTHER INFORMATION: P OR Q
<220> FEATURE:
<221> NAME/KEY: MISC_FEATURE
<222> LOCATION: (102)..(102)
<223> OTHER INFORMATION: D OR A
<220> FEATURE:
<221> NAME/KEY: MISC_FEATURE
<222> LOCATION: (107)..(107)
<223> OTHER INFORMATION: W OR C
<220> FEATURE:
<221> NAME/KEY: MISC_FEATURE
<222> LOCATION: (108)..(108)
<223> OTHER INFORMATION: N OR Y
<220> FEATURE:
<221> NAME/KEY: MISC_FEATURE
<222> LOCATION: (112)..(112)
<223> OTHER INFORMATION: R OR G
<220> FEATURE:
<221> NAME/KEY: MISC_FEATURE
<222> LOCATION: (113)..(113)
<223> OTHER INFORMATION: I, T, M OR K
<220> FEATURE:
<221> NAME/KEY: MISC_FEATURE
<222> LOCATION: (114)..(114)
<223> OTHER INFORMATION: D OR N
<220> FEATURE:
<221> NAME/KEY: MISC_FEATURE
<222> LOCATION: (115)..(115)
<223> OTHER INFORMATION: S OR Y
<220> FEATURE:
<221> NAME/KEY: MISC_FEATURE
<222> LOCATION: (116)..(116)
<223> OTHER INFORMATION: R, C OR S
<220> FEATURE:
<221> NAME/KEY: MISC_FEATURE
<222> LOCATION: (117)..(117)
<223> OTHER INFORMATION: M OR L
<220> FEATURE:
<221> NAME/KEY: MISC_FEATURE
<222> LOCATION: (118)..(118)
<223> OTHER INFORMATION: K OR IS ABSENT
<220> FEATURE:
<221> NAME/KEY: MISC_FEATURE
<222> LOCATION: (119)..(119)
<223> OTHER INFORMATION: K OR T
<220> FEATURE:
<221> NAME/KEY: MISC_FEATURE
<222> LOCATION: (120)..(120)
<223> OTHER INFORMATION: V, M, L OR S
<220> FEATURE:
<221> NAME/KEY: MISC_FEATURE
<222> LOCATION: (121)..(121)
<223> OTHER INFORMATION: K OR Q
<220> FEATURE:
<221> NAME/KEY: MISC_FEATURE
<222> LOCATION: (122)..(122)
<223> OTHER INFORMATION: D OR N
<220> FEATURE:
<221> NAME/KEY: MISC_FEATURE
<222> LOCATION: (124)..(124)
<223> OTHER INFORMATION: S OR P
<220> FEATURE:
<221> NAME/KEY: MISC_FEATURE
<222> LOCATION: (127)..(127)
<223> OTHER INFORMATION: T OR M
<220> FEATURE:
<221> NAME/KEY: MISC_FEATURE
<222> LOCATION: (128)..(128)
<223> OTHER INFORMATION: I OR R
<220> FEATURE:
<221> NAME/KEY: MISC_FEATURE
<222> LOCATION: (129)..(129)
<223> OTHER INFORMATION: K OR E
<220> FEATURE:
<221> NAME/KEY: MISC_FEATURE
<222> LOCATION: (131)..(131)
<223> OTHER INFORMATION: I OR N
<220> FEATURE:
<221> NAME/KEY: MISC_FEATURE
```

```
<222> LOCATION: (132)..(132)
<223> OTHER INFORMATION: V OR I
<220> FEATURE:
<221> NAME/KEY: MISC_FEATURE
<222> LOCATION: (133)..(133)
<223> OTHER INFORMATION: I OR R
<220> FEATURE:
<221> NAME/KEY: MISC_FEATURE
<222> LOCATION: (134)..(134)
<223> OTHER INFORMATION: R OR IS ABSENT
<220> FEATURE:
<221> NAME/KEY: MISC_FEATURE
<222> LOCATION: (138)..(138)
<223> OTHER INFORMATION: R OR Q
<220> FEATURE:
<221> NAME/KEY: MISC_FEATURE
<222> LOCATION: (139)..(139)
<223> OTHER INFORMATION: K, S OR R
<220> FEATURE:
<221> NAME/KEY: MISC_FEATURE
<222> LOCATION: (141)..(141)
<223> OTHER INFORMATION: I, T OR N
<220> FEATURE:
<221> NAME/KEY: MISC_FEATURE
<222> LOCATION: (142)..(142)
<223> OTHER INFORMATION: K OR R
<220> FEATURE:
<221> NAME/KEY: MISC_FEATURE
<222> LOCATION: (145)..(145)
<223> OTHER INFORMATION: N OR Y
<220> FEATURE:
<221> NAME/KEY: MISC_FEATURE
<222> LOCATION: (146)..(146)
<223> OTHER INFORMATION: C OR Y
<220> FEATURE:
<221> NAME/KEY: MISC_FEATURE
<222> LOCATION: (149)..(149)
<223> OTHER INFORMATION: S or F
<220> FEATURE:
<221> NAME/KEY: MISC_FEATURE
<222> LOCATION: (151)..(151)
<223> OTHER INFORMATION: E or G
<220> FEATURE:
<221> NAME/KEY: MISC_FEATURE
<222> LOCATION: (155)..(155)
<223> OTHER INFORMATION: D or E
<220> FEATURE:
<221> NAME/KEY: MISC_FEATURE
<222> LOCATION: (157)..(157)
<223> OTHER INFORMATION: I or T
<220> FEATURE:
<221> NAME/KEY: MISC_FEATURE
<222> LOCATION: (159)..(159)
<223> OTHER INFORMATION: S, L or T
<220> FEATURE:
<221> NAME/KEY: MISC_FEATURE
<222> LOCATION: (160)..(160)
<223> OTHER INFORMATION: A, E or V
<220> FEATURE:
<221> NAME/KEY: MISC_FEATURE
<222> LOCATION: (161)..(161)
<223> OTHER INFORMATION: E or is Absent
<220> FEATURE:
<221> NAME/KEY: MISC_FEATURE
<222> LOCATION: (162)..(162)
<223> OTHER INFORMATION: D OR N
<220> FEATURE:
<221> NAME/KEY: MISC_FEATURE
<222> LOCATION: (163)..(163)
<223> OTHER INFORMATION: F, L OR S
<220> FEATURE:
<221> NAME/KEY: MISC_FEATURE
<222> LOCATION: (164)..(164)
<223> OTHER INFORMATION: S OR IS ABSENT
<220> FEATURE:
<221> NAME/KEY: MISC_FEATURE
<222> LOCATION: (165)..(165)
<223> OTHER INFORMATION: T OR IS ABSENT
<220> FEATURE:
<221> NAME/KEY: MISC_FEATURE
```

```
<222> LOCATION: (166)..(166)
<223> OTHER INFORMATION: P OR T
<220> FEATURE:
<221> NAME/KEY: MISC_FEATURE
<222> LOCATION: (167)..(167)
<223> OTHER INFORMATION: S OR P
<220> FEATURE:
<221> NAME/KEY: MISC_FEATURE
<222> LOCATION: (168)..(168)
<223> OTHER INFORMATION: Q OR IS ABSENT
<220> FEATURE:
<221> NAME/KEY: MISC_FEATURE
<222> LOCATION: (169)..(169)
<223> OTHER INFORMATION: T, I OR S
<220> FEATURE:
<221> NAME/KEY: MISC_FEATURE
<222> LOCATION: (170)..(170)
<223> OTHER INFORMATION: S OR IS ABSENT
<220> FEATURE:
<221> NAME/KEY: MISC_FEATURE
<222> LOCATION: (171)..(171)
<223> OTHER INFORMATION: S, T, P OR L
<220> FEATURE:
<221> NAME/KEY: MISC_FEATURE
<222> LOCATION: (172)..(172)
<223> OTHER INFORMATION: S OR T
<220> FEATURE:
<221> NAME/KEY: MISC_FEATURE
<222> LOCATION: (173)..(173)
<223> OTHER INFORMATION: T OR K
<220> FEATURE:
<221> NAME/KEY: MISC_FEATURE
<222> LOCATION: (174)..(174)
<223> OTHER INFORMATION: K OR R
<220> FEATURE:
<221> NAME/KEY: MISC_FEATURE
<222> LOCATION: (175)..(175)
<223> OTHER INFORMATION: N, I OR R
<220> FEATURE:
<221> NAME/KEY: MISC_FEATURE
<222> LOCATION: (176)..(176)
<223> OTHER INFORMATION: G OR IS ABSENT
<220> FEATURE:
<221> NAME/KEY: MISC_FEATURE
<222> LOCATION: (177)..(177)
<223> OTHER INFORMATION: N OR S
<220> FEATURE:
<221> NAME/KEY: MISC_FEATURE
<222> LOCATION: (179)..(179)
<223> OTHER INFORMATION: W OR R
<220> FEATURE:
<221> NAME/KEY: MISC_FEATURE
<222> LOCATION: (183)..(183)
<223> OTHER INFORMATION: F OR L
<220> FEATURE:
<221> NAME/KEY: MISC_FEATURE
<222> LOCATION: (184)..(184)
<223> OTHER INFORMATION: L OR F
<220> FEATURE:
<221> NAME/KEY: MISC_FEATURE
<222> LOCATION: (185)..(185)
<223> OTHER INFORMATION: D, E OR K
<220> FEATURE:
<221> NAME/KEY: MISC_FEATURE
<222> LOCATION: (186)..(186)
<223> OTHER INFORMATION: D OR G
<220> FEATURE:
<221> NAME/KEY: MISC_FEATURE
<222> LOCATION: (187)..(187)
<223> OTHER INFORMATION: K OR E
<220> FEATURE:
<221> NAME/KEY: MISC_FEATURE
<222> LOCATION: (188)..(188)
<223> OTHER INFORMATION: E, D OR K
<220> FEATURE:
<221> NAME/KEY: MISC_FEATURE
<222> LOCATION: (189)..(189)
<223> OTHER INFORMATION: D, A, G OR V
<220> FEATURE:
<221> NAME/KEY: MISC_FEATURE
```

-continued

```
<222> LOCATION: (190)..(190)
<223> OTHER INFORMATION: T, A, F OR V
<220> FEATURE:
<221> NAME/KEY: MISC_FEATURE
<222> LOCATION: (191)..(191)
<223> OTHER INFORMATION: F OR T
<220> FEATURE:
<221> NAME/KEY: MISC_FEATURE
<222> LOCATION: (193)..(193)
<223> OTHER INFORMATION: R, K OR T
<220> FEATURE:
<221> NAME/KEY: MISC_FEATURE
<222> LOCATION: (194)..(194)
<223> OTHER INFORMATION: A, D OR T
<220> FEATURE:
<221> NAME/KEY: MISC_FEATURE
<222> LOCATION: (195)..(195)
<223> OTHER INFORMATION: A OR T
<220> FEATURE:
<221> NAME/KEY: MISC_FEATURE
<222> LOCATION: (196)..(196)
<223> OTHER INFORMATION: C, G OR Y
<220> FEATURE:
<221> NAME/KEY: MISC_FEATURE
<222> LOCATION: (197)..(197)
<223> OTHER INFORMATION: P, S OR Y
<220> FEATURE:
<221> NAME/KEY: MISC_FEATURE
<222> LOCATION: (198)..(198)
<223> OTHER INFORMATION: G OR S
<220> FEATURE:
<221> NAME/KEY: MISC_FEATURE
<222> LOCATION: (199)..(199)
<223> OTHER INFORMATION: L, I OR F
<220> FEATURE:
<221> NAME/KEY: MISC_FEATURE
<222> LOCATION: (200)..(200)
<223> OTHER INFORMATION: E, G OR A
<220> FEATURE:
<221> NAME/KEY: MISC_FEATURE
<222> LOCATION: (202)..(202)
<223> OTHER INFORMATION: E OR D
<220> FEATURE:
<221> NAME/KEY: MISC_FEATURE
<222> LOCATION: (205)..(205)
<223> OTHER INFORMATION: L OR E
<220> FEATURE:
<221> NAME/KEY: MISC_FEATURE
<222> LOCATION: (206)..(206)
<223> OTHER INFORMATION: F OR L
<220> FEATURE:
<221> NAME/KEY: MISC_FEATURE
<222> LOCATION: (207)..(207)
<223> OTHER INFORMATION: T OR A
<220> FEATURE:
<221> NAME/KEY: MISC_FEATURE
<222> LOCATION: (208)..(208)
<223> OTHER INFORMATION: S OR T
<220> FEATURE:
<221> NAME/KEY: MISC_FEATURE
<222> LOCATION: (211)..(211)
<223> OTHER INFORMATION: V, F OR A
<220> FEATURE:
<221> NAME/KEY: MISC_FEATURE
<222> LOCATION: (213)..(213)
<223> OTHER INFORMATION: D OR E
<220> FEATURE:
<221> NAME/KEY: MISC_FEATURE
<222> LOCATION: (214)..(214)
<223> OTHER INFORMATION: R, D OR M
<220> FEATURE:
<221> NAME/KEY: MISC_FEATURE
<222> LOCATION: (215)..(215)
<223> OTHER INFORMATION: M, L OR Q
<220> FEATURE:
<221> NAME/KEY: MISC_FEATURE
<222> LOCATION: (216)..(216)
<223> OTHER INFORMATION: P, S OR Q
<220> FEATURE:
<221> NAME/KEY: MISC_FEATURE
```

```
<222> LOCATION: (217)..(217)
<223> OTHER INFORMATION: Q, A, P OR S
<220> FEATURE:
<221> NAME/KEY: MISC_FEATURE
<222> LOCATION: (218)..(218)
<223> OTHER INFORMATION: S, R OR A
<220> FEATURE:
<221> NAME/KEY: MISC_FEATURE
<222> LOCATION: (219)..(219)
<223> OTHER INFORMATION: T, K OR R
<220> FEATURE:
<221> NAME/KEY: MISC_FEATURE
<222> LOCATION: (220)..(220)
<223> OTHER INFORMATION: R OR S
<220> FEATURE:
<221> NAME/KEY: MISC_FEATURE
<222> LOCATION: (221)..(221)
<223> OTHER INFORMATION: S, T, Q, C OR K
<220> FEATURE:
<221> NAME/KEY: MISC_FEATURE
<222> LOCATION: (222)..(222)
<223> OTHER INFORMATION: C OR T
<220> FEATURE:
<221> NAME/KEY: MISC_FEATURE
<222> LOCATION: (223)..(223)
<223> OTHER INFORMATION: A, I, V OR T
<220> FEATURE:
<221> NAME/KEY: MISC_FEATURE
<222> LOCATION: (224)..(224)
<223> OTHER INFORMATION: N OR S
<220> FEATURE:
<221> NAME/KEY: MISC_FEATURE
<222> LOCATION: (225)..(225)
<223> OTHER INFORMATION: F OR V
<220> FEATURE:
<221> NAME/KEY: MISC_FEATURE
<222> LOCATION: (226)..(226)
<223> OTHER INFORMATION: P, S OR T
<220> FEATURE:
<221> NAME/KEY: MISC_FEATURE
<222> LOCATION: (228)..(228)
<223> OTHER INFORMATION: E OR IS ABSENT
<220> FEATURE:
<221> NAME/KEY: MISC_FEATURE
<222> LOCATION: (230)..(230)
<223> OTHER INFORMATION: L, Q, H OR P
<220> FEATURE:
<221> NAME/KEY: MISC_FEATURE
<222> LOCATION: (231)..(231)
<223> OTHER INFORMATION: S, G OR I
<220> FEATURE:
<221> NAME/KEY: MISC_FEATURE
<222> LOCATION: (232)..(232)
<223> OTHER INFORMATION: R, K OR T
<220> FEATURE:
<221> NAME/KEY: MISC_FEATURE
<222> LOCATION: (233)..(233)
<223> OTHER INFORMATION: G OR S
<220> FEATURE:
<221> NAME/KEY: MISC_FEATURE
<222> LOCATION: (234)..(234)
<223> OTHER INFORMATION: E, D OR N
<220> FEATURE:
<221> NAME/KEY: MISC_FEATURE
<222> LOCATION: (235)..(235)
<223> OTHER INFORMATION: F OR L
<220> FEATURE:
<221> NAME/KEY: MISC_FEATURE
<222> LOCATION: (237)..(237)
<223> OTHER INFORMATION: F OR V
<220> FEATURE:
<221> NAME/KEY: MISC_FEATURE
<222> LOCATION: (238)..(238)
<223> OTHER INFORMATION: S OR N
<220> FEATURE:
<221> NAME/KEY: MISC_FEATURE
<222> LOCATION: (239)..(239)
<223> OTHER INFORMATION: V, M OR T
<220> FEATURE:
<221> NAME/KEY: MISC_FEATURE
```

<222> LOCATION: (240)..(240)
<223> OTHER INFORMATION: D OR E
<220> FEATURE:
<221> NAME/KEY: MISC_FEATURE
<222> LOCATION: (241)..(241)
<223> OTHER INFORMATION: L OR P
<220> FEATURE:
<221> NAME/KEY: MISC_FEATURE
<222> LOCATION: (247)..(247)
<223> OTHER INFORMATION: E OR K
<220> FEATURE:
<221> NAME/KEY: MISC_FEATURE
<222> LOCATION: (248)..(248)
<223> OTHER INFORMATION: E OR N
<220> FEATURE:
<221> NAME/KEY: MISC_FEATURE
<222> LOCATION: (249)..(249)
<223> OTHER INFORMATION: S OR IS ABSENT

<400> SEQUENCE: 101

```
Met Glu Gly Tyr Asn Xaa Xaa Xaa Xaa Xaa Xaa Xaa Xaa Xaa Ala Trp
1               5                   10                  15

Thr Arg Xaa Glu Asp Xaa Leu Leu Arg Gln Cys Xaa Xaa Xaa Xaa Gly
            20                  25                  30

Glu Gly Lys Trp Xaa Gln Val Xaa Xaa Lys Xaa Gly Leu Xaa Arg Cys
        35                  40                  45

Arg Xaa Ser Cys Arg Xaa Arg Trp Xaa Asn Tyr Xaa Lys Pro Xaa Ile
    50                  55                  60

Lys Arg Gly Xaa Phe Xaa Glu Asp Glu Val Asp Leu Ile Xaa Arg Leu
65                  70                  75                  80

His Xaa Leu Leu Gly Asn Arg Trp Ser Leu Ile Ala Xaa Arg Leu Xaa
                85                  90                  95

Gly Arg Thr Ala Asn Xaa Val Lys Asn Tyr Xaa Xaa Thr Arg Leu Xaa
            100                 105                 110

Xaa Xaa Xaa Xaa Xaa Xaa Xaa Xaa Xaa Xaa Lys Xaa Gln Glu Xaa Xaa
        115                 120                 125

Xaa Thr Xaa Xaa Xaa Xaa Pro Gln Pro Xaa Xaa Phe Xaa Xaa Ser Ser
    130                 135                 140

Xaa Xaa Leu Ser Xaa Lys Xaa Pro Ile Leu Xaa His Xaa Gln Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Asp Xaa Trp Glu Thr Xaa Xaa Xaa Xaa Xaa Xaa Xaa Xaa Xaa Glu
            180                 185                 190

Xaa Xaa Xaa Xaa Xaa Xaa Xaa Xaa Leu Xaa Glu Glu Xaa Xaa Xaa Xaa
        195                 200                 205

Phe Trp Xaa Asp Xaa Xaa Xaa Xaa Xaa Xaa Xaa Xaa Xaa Xaa Xaa Xaa
    210                 215                 220

Xaa Xaa Glu Xaa Gly Xaa Xaa Xaa Xaa Xaa Xaa Ser Xaa Xaa Xaa Xaa
225                 230                 235                 240

Xaa Trp Asn His Ser Lys Xaa Xaa Xaa
                245
```

<210> SEQ ID NO 102
<211> LENGTH: 4078
<212> TYPE: DNA
<213> ORGANISM: Malus domestica

<400> SEQUENCE: 102

```
tcgatttaag agatggaggg atataacgaa aacctgagtg tgagaaaagg tgcctggact      60
cgagaggaag acaatcttct caggcagtgc gttgagattc atggagaggg aaagtggaac     120
```

```
caagtttcat acaaagcagg tatatatgtt aatgtgtata tttaactgtg aaagatggat    180
atgtgtatta ttttaaagca tttcactagt atttcattct aagaccttt  gttaaatagt    240
ttcaagtttc aagttttact tttattaatg ttttagaaca tgttaatatg tctaacggtc    300
atacttgctc tcacctcact catctattgt gtttacatat atggctaaaa tgacctatgc    360
gtgtgtgagg agggccatgt tgagagactt agtccctcat aaatatttgt tgttcacgta    420
gaaagatgtt atgtgaatgt aaactttgaa ttatgtatgc aggcttaaac aggtgcagga    480
agagctgcag acaaagatgg ttaaactatc tgaagccaaa tatcaagaga ggagacttta    540
aagaggatga agtagatctt ataattagac ttcacaggct tttgggaaac aggtactaat    600
aaataagtgt cattttcaat tcatgtcgtc gttttcattg tacgaaatt  gggcctatta    660
acagtgagat tataatcata gacctcaaat tacttttttcc actctttta  tatttaatgt    720
ttttcaatga agtattagtg gtgtgtagaa tataaaaaaa aataaaaggt gttgtgtaag    780
taatttggag tgtgtgaata taatcttct  tgttaatata ttctggctcc ccatattttc    840
agtattttct aatacttcct aatttatatg tcattttatt tttcatttag acatcaagca    900
aaaagttttc aattttgtag tatttttttt agatttatta aaaacaatta tttcccaaat    960
ttttttttgtg ggccaatggc ctaccacatc attgtttaat ggagaactta aaggctagag   1020
taacgaagta tgattttaga gtaaatcgta atttaggaa  aaaagtgag aggagaaaaa    1080
ctaagggtag caacttgcaa acttcatgat acttgagtat agtaaagtga ggattactct   1140
tatttttag  ctatagtcta gcatgagaat ctaaactaca aaatcattag agagggcaag   1200
cgttataaac attcatttta aattttttaa tattataata ttctacctta aggggcagag   1260
ttgttttttg gttaagcaaa acaaaaaatc attcgtatca aatgtggtat cattgaaaat   1320
caaacttcag actttagtct taattttaa  aatgaagaca aatatcgagt gctaatagca   1380
ataaaccaaa aattttagga actgtttggt atcttatttg aaattttta  tcatttctca   1440
aaacatttt  taaaaacatt tcttgaaaac aattttcttt aagactcaaa aacttgatgg   1500
gtatgcaaat taaaaatttc aaatcttacg actttaacta gacaaagaga tctaaacaga   1560
gggggtcacg gtagagggag aaagaagaga gaggaggaaa aaaagtaaga gatgattgaa   1620
tgaaagagaa agaagagaga tgatcgggat gaaatagaga ggaatatgag tgagagaaag   1680
aactgagagg ataaaaagag cagattggag aaaagacgaa aaggtaataa aaaaaggaga   1740
gagaaagaag aaaagagaga gatagatttg gagagagaga gagaagaaga gaaataaat    1800
aagagagttt aagtttaaaa actctaaaac tcacttttta tgtttagat  aatagactat   1860
attttgagt  tagtcttgag ttcaattttt aaaaatagtc ctaccaaaaa agttttaag    1920
gcctaaaact tgaaaattgt ttttgagttt aaaaagttgg attcaaataa agtatcaaac   1980
aggtccttag tttttttcttg accgaaaaaa taaaaatctt tatccggaag ggcattagta   2040
aactcaaaca cctttcttc  gtaatgattt ttgtatgtaa agtcattttc atgctttaa    2100
tccctagtcg actgagcaaa cctttaagat tgtgtattcg gccaacagag gcttggatca   2160
gaatagataa gaagttatac attcaaaatt tcacaattaa tagaattaga agggagaact   2220
ttggtaataa atacacgcag taattttatt ttttgtatta aaactaatgt tcgggcaagg   2280
atttggcctt ggcacagctc ccttggagtg ttggcacttg gcgttgatgt tggttgttgg   2340
tcgagttctt gctacttggt gtgctacaag aagagtacaa agttagtttt gaaatgtgcc   2400
tttgtgggc  cttagatgta ggtcttgagg ctcacaatca aaactaacaa aaagttaggc   2460
gtgccactgt tatctcaata taatagatgt tgaatatatt tgatctaagt cgattacttg   2520
```

```
cgccccaaga tgcttaaact tcttattatc aaaggattgt cacaaatggg ttaagtctgc    2580
attaagttct ttttcttgcc ttgtgaccaa ggacttttc ttatagtttt gtatgtttag    2640
atgaagggag tccataaccc ttttaatcat tcgcttgatt acaattcgac gcttaaagaa    2700
gtgaagttaa cttgcttagc caaatttgat cataaatggg tcttagagcg agaaacaatt    2760
gtaagtgagt taaacataa cataatatgc atttaaacaa caatctaca aactgtaagt    2820 acaaacacaa ggaagttggg caagatttca tcttgtcggg caaggttcaa acctcttgca    2880
accacttctc cttgagtttg tagaagagtt gtgggtactg caaatggaa atgtaagcag    2940 gaaatacaaa caaggtttcc taaagggaat ctattctacg aatctaggat aaggtagcag    3000
agctttgcca aaagatggct ttctgcgtgg aatctatggc taaaaggtgc ataatctgga    3060
cgaagtgcag ctttttggtt atttgcttgt ctgagaggca agtttgtatg tcttttgttt    3120
gattggttga gtgtccttgt ctctgttgtc tctttctcct tttatagacg atttggcccg    3180
actgcttttg gctctattct tgtccgaaag ctcttggagg gcaatgagtc atcatctttt    3240
tacttgtagt gccattagaa agtgtttttt ggctaatagt gagttgatct ctgtcacttg    3300
tcacttcact cctacacatg tggcctatat tttaattgag gaggcaccaa tttgttccag    3360
gcttgtcgac tgggcctcgg gcaagtcttc acttaatttg acatccatgg gtcttggcta    3420
tctacaaaac cttatgttaa atattaactc aaacaactag tccactccat ttaattctaa    3480
agaagaaaat cgtttatgca atctctgttc ctttttttt ctttattcat cttattttc    3540 aggcaaatgt attcatcatt ttttcttcat gcatgtaatg tacttaggtg gtcattgatt    3600
gctagaagac ttccaggaag aacagcaaat gctgtgaaaa attattggaa cactcgattg    3660
cggatcgatt ctcgcatgaa aacggtgaaa aataaatctc aagaaatgag agagaccaat    3720
gtgataagac ctcagcccca aaattcaac agaagttcat attacttaag cagtaaagaa    3780
ccaattctag accatattca atcagcagaa gatttaagta cgccaccaca aacgtcgtcg    3840
tcaacaaaga atggaaatga ttggtgggag accttgttag aaggcgagga tacttttgaa    3900
agagctgcat atcccagcat tgagttagag gaagaactct tcacaagttt ttggtttgat    3960
gatcgactgt cgccaagatc atgcgccaat tttcctgaag gacaaagtag aagggaattc    4020
tcctttagca cggaccttg gaatcattca aagaagaat agctagagaa aatgattc    4078
```

<210> SEQ ID NO 103
<211> LENGTH: 104
<212> TYPE: PRT
<213> ORGANISM: Malus domestica

<400> SEQUENCE: 103

```
Val Arg Lys Gly Ala Trp Thr Arg Glu Glu Asp Asn Leu Leu Arg Gln
1               5                   10                  15

Cys Val Glu Ile His Gly Glu Gly Lys Trp Asn Gln Val Ser Tyr Lys
            20                  25                  30

Ala Gly Leu Asn Arg Cys Arg Lys Ser Cys Arg Gln Arg Trp Leu Asn
        35                  40                  45

Tyr Leu Lys Pro Asn Ile Lys Arg Gly Asp Phe Lys Glu Asp Glu Val
    50                  55                  60

Asp Leu Ile Ile Arg Leu His Arg Leu Leu Gly Asn Arg Trp Ser Leu
65                  70                  75                  80

Ile Ala Arg Arg Leu Pro Gly Arg Thr Ala Asn Ala Val Lys Asn Tyr
                85                  90                  95

Trp Asn Thr Arg Leu Arg Ile Asp
            100
```

<210> SEQ ID NO 104
<211> LENGTH: 104
<212> TYPE: PRT
<213> ORGANISM: Arabidopsis thaliana

<400> SEQUENCE: 104

Leu Arg Lys Gly Ala Trp Thr Thr Glu Glu Asp Ser Leu Leu Arg Gln
1               5                   10                  15

Cys Ile Asn Lys Tyr Gly Glu Gly Lys Trp His Gln Val Pro Val Arg
            20                  25                  30

Ala Gly Leu Asn Arg Cys Arg Lys Ser Cys Arg Leu Arg Trp Leu Asn
        35                  40                  45

Tyr Leu Lys Pro Ser Ile Lys Arg Gly Lys Leu Ser Ser Asp Glu Val
    50                  55                  60

Asp Leu Leu Arg Leu His Arg Leu Leu Gly Asn Arg Trp Ser Leu
65                  70                  75                  80

Ile Ala Gly Arg Leu Pro Gly Arg Thr Ala Asn Asp Val Lys Asn Tyr
                85                  90                  95

Trp Asn Thr His Leu Ser Lys Lys
            100

<210> SEQ ID NO 105
<211> LENGTH: 104
<212> TYPE: PRT
<213> ORGANISM: Arabidopsis thaliana

<400> SEQUENCE: 105

Leu Arg Lys Gly Ala Trp Thr Ala Glu Glu Asp Ser Leu Leu Arg Leu
1               5                   10                  15

Cys Ile Asp Lys Tyr Gly Glu Gly Lys Trp His Gln Val Pro Leu Arg
            20                  25                  30

Ala Gly Leu Asn Arg Cys Arg Lys Ser Cys Arg Leu Arg Trp Leu Asn
        35                  40                  45

Tyr Leu Lys Pro Ser Ile Lys Arg Gly Arg Leu Ser Asn Asp Glu Val
    50                  55                  60

Asp Leu Leu Arg Leu His Lys Leu Leu Gly Asn Arg Trp Ser Leu
65                  70                  75                  80

Ile Ala Gly Arg Leu Pro Gly Arg Thr Ala Asn Asp Val Lys Asn Tyr
                85                  90                  95

Trp Asn Thr His Leu Ser Lys Lys
            100

<210> SEQ ID NO 106
<211> LENGTH: 104
<212> TYPE: PRT
<213> ORGANISM: Vitis labrusca x Vitis vinifera

<400> SEQUENCE: 106

Val Arg Lys Gly Ala Trp Ile Gln Glu Glu Asp Val Leu Leu Arg Lys
1               5                   10                  15

Cys Ile Glu Lys Tyr Gly Glu Gly Lys Trp His Leu Val Pro Leu Arg
            20                  25                  30

Ala Gly Leu Asn Arg Cys Arg Lys Ser Cys Arg Leu Arg Trp Leu Asn
        35                  40                  45

Tyr Leu Lys Pro Asp Ile Lys Arg Gly Glu Phe Ala Leu Asp Glu Val
    50                  55                  60

```
Asp Leu Met Ile Arg Leu His Asn Leu Leu Gly Asn Arg Trp Ser Leu
 65                  70                  75                  80

Ile Ala Gly Arg Leu Pro Gly Arg Thr Ala Asn Asp Val Lys Asn Tyr
                 85                  90                  95

Trp His Gly His His Leu Lys Lys
            100

<210> SEQ ID NO 107
<211> LENGTH: 104
<212> TYPE: PRT
<213> ORGANISM: Capsicum annuum

<400> SEQUENCE: 107

Val Arg Lys Gly Ala Trp Thr Glu Glu Asp Phe Leu Leu Arg Lys
 1               5                  10                  15

Cys Ile Gln Asn Tyr Gly Glu Gly Lys Trp His Leu Val Pro Ile Arg
                 20                  25                  30

Ala Gly Leu Asn Arg Cys Arg Lys Ser Cys Arg Leu Arg Trp Leu Asn
             35                  40                  45

Tyr Leu Arg Pro His Ile Lys Arg Gly Asp Phe Gly Trp Asp Glu Ile
         50                  55                  60

Asp Leu Ile Leu Arg Leu His Lys Leu Leu Gly Asn Arg Trp Ser Leu
 65                  70                  75                  80

Ile Ala Gly Arg Leu Pro Gly Arg Thr Ala Asn Asp Val Lys Asn Tyr
                 85                  90                  95

Trp Asn Ser His Leu Gln Lys Lys
            100

<210> SEQ ID NO 108
<211> LENGTH: 104
<212> TYPE: PRT
<213> ORGANISM: Petunia hybrida

<400> SEQUENCE: 108

Val Arg Lys Gly Ala Trp Thr Glu Glu Asp Leu Leu Leu Arg Glu
 1               5                  10                  15

Cys Ile Asp Lys Tyr Gly Glu Gly Lys Trp His Leu Val Pro Val Arg
                 20                  25                  30

Ala Gly Leu Asn Arg Cys Arg Lys Ser Cys Arg Leu Arg Trp Leu Asn
             35                  40                  45

Tyr Leu Arg Pro His Ile Lys Arg Gly Asp Phe Ser Leu Asp Glu Val
         50                  55                  60

Asp Leu Ile Leu Arg Leu His Lys Leu Leu Gly Asn Arg Trp Ser Leu
 65                  70                  75                  80

Ile Ala Gly Arg Leu Pro Gly Arg Thr Ala Asn Asp Val Lys Asn Tyr
                 85                  90                  95

Trp Asn Thr His Leu Arg Lys Lys
            100

<210> SEQ ID NO 109
<211> LENGTH: 104
<212> TYPE: PRT
<213> ORGANISM: Solanum lycopersicum

<400> SEQUENCE: 109

Val Arg Lys Gly Ser Trp Thr Asp Glu Glu Asp Phe Leu Leu Arg Lys
 1               5                  10                  15

Cys Ile Asp Lys Tyr Gly Glu Gly Lys Trp His Leu Val Pro Ile Arg
                 20                  25                  30
```

Ala Gly Leu Asn Arg Cys Arg Lys Ser Cys Arg Leu Arg Trp Leu Asn
          35                  40                  45

Tyr Leu Arg Pro His Ile Lys Arg Gly Asp Phe Glu Gln Asp Glu Val
 50                  55                  60

Asp Leu Ile Leu Arg Leu His Lys Leu Leu Gly Asn Arg Trp Ser Leu
 65                  70                  75                  80

Ile Ala Gly Arg Leu Pro Gly Arg Thr Ala Asn Asp Val Lys Asn Tyr
                 85                  90                  95

Trp Asn Thr Asn Leu Leu Arg Lys
               100

<210> SEQ ID NO 110
<211> LENGTH: 104
<212> TYPE: PRT
<213> ORGANISM: Gerbera hybrid cv

<400> SEQUENCE: 110

Leu Arg Lys Gly Ala Trp Thr Ala Glu Glu Asp Met Leu Leu Lys Asn
 1               5                  10                  15

Cys Ile Glu Arg Tyr Gly Glu Gly Lys Trp His Leu Val Pro Leu Lys
             20                  25                  30

Ala Gly Leu Asn Arg Cys Arg Lys Ser Cys Arg Leu Arg Trp Leu Asn
          35                  40                  45

Tyr Leu Arg Pro Asn Ile Lys Arg Gly Asp Phe Gly Glu Asp Glu Ile
 50                  55                  60

Asp Leu Ile Ile Arg Leu His Lys Leu Leu Gly Asn Arg Trp Ser Leu
 65                  70                  75                  80

Ile Ala Gly Arg Ile Pro Gly Arg Thr Ala Asn Asp Val Lys Asn Trp
                 85                  90                  95

Trp Asn Thr His Leu Arg Ser Arg
               100

<210> SEQ ID NO 111
<211> LENGTH: 104
<212> TYPE: PRT
<213> ORGANISM: Picea mariana

<400> SEQUENCE: 111

Leu Asn Lys Gly Ala Trp Ser Ala Glu Glu Asp Ser Leu Leu Gly Lys
 1               5                  10                  15

Tyr Ile Gln Thr His Gly Glu Gly Asn Trp Arg Ser Leu Pro Lys Lys
             20                  25                  30

Ala Gly Leu Arg Arg Cys Gly Lys Ser Cys Arg Leu Arg Trp Leu Asn
          35                  40                  45

Tyr Leu Arg Pro Cys Ile Lys Arg Gly Asn Ile Thr Ala Asp Glu Glu
 50                  55                  60

Glu Leu Ile Ile Arg Met His Ala Leu Leu Gly Asn Arg Trp Ser Ile
 65                  70                  75                  80

Ile Ala Gly Arg Val Pro Gly Arg Thr Asp Asn Glu Ile Lys Asn Tyr
                 85                  90                  95

Trp Asn Thr Asn Leu Ser Lys Lys
               100

<210> SEQ ID NO 112
<211> LENGTH: 102
<212> TYPE: PRT
<213> ORGANISM: Zea mays

```
<400> SEQUENCE: 112

Val Lys Arg Gly Ala Trp Thr Ser Lys Glu Asp Asp Ala Leu Ala Ala
1               5                   10                  15

Tyr Val Lys Ala His Gly Glu Gly Lys Trp Arg Glu Val Pro Gln Lys
                20                  25                  30

Ala Gly Leu Arg Arg Cys Gly Lys Ser Cys Arg Leu Arg Trp Leu Asn
            35                  40                  45

Tyr Leu Arg Pro Asn Ile Arg Gly Asn Ile Ser Tyr Asp Glu Glu
    50                  55                  60

Asp Leu Ile Ile Arg Leu His Arg Leu Gly Asn Arg Trp Ser Leu
65                  70                  75                  80

Ile Ala Gly Arg Leu Pro Gly Arg Thr Asp Asn Glu Ile Lys Asn Tyr
                85                  90                  95

Trp Asn Ser Thr Leu Val
            100

<210> SEQ ID NO 113
<211> LENGTH: 104
<212> TYPE: PRT
<213> ORGANISM: Arabidopsis thaliana

<400> SEQUENCE: 113

Leu Asn Arg Gly Ala Trp Thr Asp His Glu Asp Lys Ile Leu Arg Asp
1               5                   10                  15

Tyr Ile Thr Thr His Gly Glu Gly Lys Trp Ser Thr Leu Pro Asn Gln
                20                  25                  30

Ala Gly Leu Lys Arg Cys Gly Lys Ser Cys Arg Leu Arg Trp Lys Asn
            35                  40                  45

Tyr Leu Arg Pro Gly Ile Lys Arg Gly Asn Ile Ser Ser Asp Glu Glu
    50                  55                  60

Glu Leu Ile Ile Arg Leu His Asn Leu Gly Asn Arg Trp Ser Leu
65                  70                  75                  80

Ile Ala Gly Arg Leu Pro Gly Arg Thr Asp Asn Glu Ile Lys Asn His
                85                  90                  95

Trp Asn Ser Asn Leu Arg Lys Arg
            100

<210> SEQ ID NO 114
<211> LENGTH: 104
<212> TYPE: PRT
<213> ORGANISM: Malus domestica

<400> SEQUENCE: 114

Leu Asn Arg Gly Ala Trp Thr Ala Leu Glu Asp Lys Ile Leu Ser Ser
1               5                   10                  15

Tyr Ile Lys Ala His Gly Glu Gly Lys Trp Arg Ser Leu Pro Lys Arg
                20                  25                  30

Ala Gly Leu Lys Arg Cys Gly Lys Ser Cys Arg Leu Arg Trp Leu Asn
            35                  40                  45

Tyr Leu Arg Pro Asp Ile Lys Arg Gly Asn Ile Ser Gly Asp Glu Glu
    50                  55                  60

Glu Leu Ile Val Arg Leu His Asn Leu Gly Asn Arg Trp Ser Leu
65                  70                  75                  80

Ile Ala Gly Arg Leu Pro Gly Arg Thr Asp Asn Glu Ile Lys Asn Tyr
                85                  90                  95

Trp Asn Thr Thr Leu Gly Lys Lys
            100
```

<210> SEQ ID NO 115
<211> LENGTH: 104
<212> TYPE: PRT
<213> ORGANISM: Malus domestica

<400> SEQUENCE: 115

Leu Asn Arg Gly Ala Trp Thr Ala Met Glu Asp Lys Val Leu Thr Glu
1               5                   10                  15

Tyr Ile Gly Asn His Gly Glu Gly Lys Trp Arg Asn Leu Pro Lys Arg
            20                  25                  30

Ala Gly Leu Lys Arg Cys Gly Lys Ser Cys Arg Leu Arg Trp Leu Asn
        35                  40                  45

Tyr Leu Arg Pro Asp Ile Lys Arg Gly Asn Ile Thr Arg Asp Glu Glu
    50                  55                  60

Glu Leu Ile Ile Arg Leu His Lys Leu Leu Gly Asn Arg Trp Ser Leu
65                  70                  75                  80

Ile Ala Gly Arg Leu Pro Gly Arg Thr Asp Asn Glu Ile Lys Asn Tyr
                85                  90                  95

Trp Asn Thr Thr Ile Gly Lys Arg
            100

<210> SEQ ID NO 116
<211> LENGTH: 104
<212> TYPE: PRT
<213> ORGANISM: Zea mays

<400> SEQUENCE: 116

Leu Lys Arg Gly Arg Trp Thr Ala Glu Glu Asp Gln Leu Leu Ala Asn
1               5                   10                  15

Tyr Ile Ala Glu His Gly Glu Gly Ser Trp Arg Ser Leu Pro Lys Asn
            20                  25                  30

Ala Gly Leu Leu Arg Cys Gly Lys Ser Cys Arg Leu Arg Trp Ile Asn
        35                  40                  45

Tyr Leu Arg Ala Asp Val Lys Arg Gly Asn Ile Ser Lys Glu Glu Glu
    50                  55                  60

Asp Ile Ile Ile Lys Leu His Ala Thr Leu Gly Asn Arg Trp Ser Leu
65                  70                  75                  80

Ile Ala Ser His Leu Pro Gly Arg Thr Asp Asn Glu Ile Lys Asn Tyr
                85                  90                  95

Trp Asn Ser His Leu Ser Arg Gln
            100

<210> SEQ ID NO 117
<211> LENGTH: 104
<212> TYPE: PRT
<213> ORGANISM: Malus domestica

<400> SEQUENCE: 117

Leu Arg Arg Gly Gln Trp Ile Leu Glu Glu Asp Ser Leu Leu Ile Gln
1               5                   10                  15

Tyr Ile Glu Arg His Gly Glu Gly Gln Trp Asn Leu Leu Ala Lys Arg
            20                  25                  30

Ser Gly Leu Arg Arg Thr Gly Lys Ser Cys Arg Leu Arg Trp Leu Asn
        35                  40                  45

Tyr Leu Lys Pro Asp Val Lys Arg Gly Asn Leu Ser Pro Glu Glu Gln
    50                  55                  60

Leu Leu Ile Leu Asp Leu His Ser Lys Met Gly Asn Arg Trp Ser Lys

```
                65                  70                  75                  80
Ile Ala Arg Tyr Leu Pro Gly Arg Thr Asp Asn Glu Ile Lys Asn Tyr
                    85                  90                  95
Trp Arg Thr Arg Val His Lys Gln
                100
```

<210> SEQ ID NO 118
<211> LENGTH: 103
<212> TYPE: PRT
<213> ORGANISM: Arabidopsis thaliana

<400> SEQUENCE: 118

```
Lys Lys Gly Leu Trp Thr Val Glu Glu Asp Asn Ile Leu Met Asp Tyr
1               5                   10                  15
Val Leu Asn His Gly Thr Gly Gln Trp Asn Arg Ile Val Arg Lys Thr
                20                  25                  30
Gly Leu Lys Arg Cys Gly Lys Ser Cys Arg Leu Arg Trp Met Asn Tyr
            35                  40                  45
Leu Ser Pro Asn Val Asn Lys Gly Asn Phe Thr Glu Gln Glu Glu Asp
        50                  55                  60
Leu Ile Ile Arg Leu His Lys Leu Leu Gly Asn Arg Trp Ser Leu Ile
65                  70                  75                  80
Ala Lys Arg Val Pro Gly Arg Thr Asp Asn Gln Val Lys Asn Tyr Trp
                85                  90                  95
Asn Thr His Leu Ser Lys Lys
                100
```

<210> SEQ ID NO 119
<211> LENGTH: 248
<212> TYPE: PRT
<213> ORGANISM: Arabidopsis thaliana

<400> SEQUENCE: 119

```
Met Glu Gly Ser Ser Lys Gly Leu Arg Lys Gly Ala Trp Thr Thr Glu
1               5                   10                  15
Glu Asp Ser Leu Leu Arg Gln Cys Ile Asn Lys Tyr Gly Glu Gly Lys
                20                  25                  30
Trp His Gln Val Pro Val Arg Ala Gly Leu Asn Arg Cys Arg Lys Ser
            35                  40                  45
Cys Arg Leu Arg Trp Leu Asn Tyr Leu Lys Pro Ser Ile Lys Arg Gly
        50                  55                  60
Lys Leu Ser Ser Asp Glu Val Asp Leu Leu Leu Arg Leu His Arg Leu
65                  70                  75                  80
Leu Gly Asn Arg Trp Ser Leu Ile Ala Gly Arg Leu Pro Gly Arg Thr
                85                  90                  95
Ala Asn Asp Val Lys Asn Tyr Trp Asn Thr His Leu Ser Lys Lys His
                100                 105                 110
Glu Pro Cys Cys Lys Ile Lys Met Lys Lys Arg Asp Ile Thr Pro Ile
            115                 120                 125
Pro Thr Thr Pro Ala Leu Lys Asn Asn Val Tyr Lys Pro Arg Pro Arg
        130                 135                 140
Ser Phe Thr Val Asn Asn Asp Cys Asn His Leu Asn Ala Pro Pro Lys
145                 150                 155                 160
Val Asp Val Asn Pro Pro Cys Leu Gly Leu Asn Ile Asn Asn Val Cys
                165                 170                 175
Asp Asn Ser Ile Ile Tyr Asn Lys Asp Lys Lys Asp Gln Leu Val
                180                 185                 190
```

```
Asn Asn Leu Ile Asp Gly Asp Asn Met Trp Leu Glu Lys Phe Leu Glu
    195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245
```

COMPOSITIONS AND METHODS FOR MODULATING PIGMENT PRODUCTION IN PLANTS

CROSS-REFERENCE TO RELATED APPLICATIONS

This application is a United States national stage application under 35 U.S.C. §371 of International Application No. PCT/NZ2006/000221, filed Aug. 31, 2006, which claims benefit of New Zealand Patent Application No. 542110 filed Aug. 30, 2005; both of which are hereby incorporated by reference in their entireties to the extent not inconsistent with the disclosure herein.

TECHNICAL FIELD

The present invention is in the field of pigment development in plants.

BACKGROUND ART

The accumulation of anthocyanin pigments is an important determinant of fruit quality. Pigments provide essential cultivar differentiation for consumers and are implicated in the health attributes of apple fruit (Boyer and Liu, 2004).

Anthocyanin pigments belong to the diverse group of ubiquitous secondary metabolites, collectively known as flavonoids. In plants, flavonoids are implicated in numerous biological functions, including defence, whilst the pigmented anthocyanin compounds in particular play a vital physiological role as attractants in plant/animal interactions.

The predominant precursors for all flavonoids, including anthocyanins, are malonyl-CoA and p-coumaroyl-CoA. From these precursors the enzyme chalcone synthase (CHS) forms chalcone, the first committed step towards anthocyanin production and the establishment of the $C_{15}$ backbone. Chalcone is then isomerised by chalcone isomerase (CHI) to produce chalcone naringenin and from there a hydroxylation step via flavanone 3β-hydroxylase (F3H) converts naringenin to dihydroflavonol. Reduction of dihydroflavonon by dihydroflavolon 4-reductase (DFR) produces leucoanthocyanin which is converted into the coloured compound anthocyanindin by leucoanthocyanidin dioxygenase (LDOX) whilst the final glycosylation step is mediated by uridin diphosphate (UDP)-glucose:flavonoid 3-0-glucosyltransferase (UFGT). The difference in anthocyanin colour can be due to a number of factors including the molecular structure and the type and number of hydroxyl groups, sugars and acids attached and the cellular environment such as pH or ultrastructure. Of the many anthocyanin pigments it is cyanidin, in the form of cyanidin 3-0-galactoside, which is primarily responsible for the red colouration in apple skin and the enzymes in this biosynthetic pathway for apple have been well described (Kim et al., 2003, Plant Science 165, 403-413; Honda et al., 2002, Plant Physiology and Biochemistry 40, 955-962). It has long been observed that anthocyanins are elevated in response to particular environmental, developmental and pathogenic stimuli. Research into apple fruit has demonstrated both the environmental and developmental regulation of anthocyanin accumulation. Pigment biosynthesis can be induced when fruit are subjected to white light, or more significantly, UV light, a phenomenon also observed in other species. Furthermore, anthocyanin levels can be elevated by cold temperature storage of the fruit. There is evidence for the coordinate induction of anthocyanin enzymes in a developmental manner in apple fruit with pronounced anthocyanin enzyme activity and correlated pigmentation increases in immature fruit and then again at ripening which appears to depend on the cultivar.

Studies show that there is highly specific regulation of genes in the anthocyanin pathway by specific binding of transcription factors (TFs) as complexes with promoter elements (Holton and Cornish, 1995, Plant Cell 7, 1071-1083). This regulation may also extend to non-pathway genes such as anthocyanin transport proteins.

MYB TFs have been shown to play an important role in transcriptional regulation of anthocyanins. Plant MYBs have been implicated in controlling pathways as diverse as secondary metabolism (including the anthocyanin pathway), development, signal transduction and disease resistance (Jin and Martin, 1999, Plant Mol Biol, 41, 577-585). They are characterised by a structurally conserved DNA binding domain consisting of single or multiple imperfect repeats; those associated with the anthocyanin pathway tend to the two-repeat (R2R3) class. Regulation can also be specific to discreet groups of genes, either early or late in the anthocyanin biosynthetic pathway. In the leaves of perilla, Perilla fruitescens, TF-driven regulation has been observed in virtually all stages of anthocyanin biosynthesis from CHS to the resultant anthocyanin protein transport genes whilst in grape, Vitis vinifera, specific regulation by MybA is restricted to the end-point of protein production (UFGT).

There are approximately 140 R3 MYB TFs in Arabidopsis, divided into 24 sub groups (Stracke et al. 2001, Current Opinion in Plant Biology, 4, 447-556). The Production of Anthocyanin Pigment 1 (PAP1) MYB (Borevitz et al., 2000, Plant Cell, 12, 2383-2394) falls into subgroup 10 (when the phylogeny of Stracke et al., 2001 is used) and demonstrates a high degree of amino acid conservation with other known anthocyanin regulators. When PAP1 was overexpressed in transgenic Arabidopsis this led to up-regulation of a number of genes in the anthocyanin biosynthesis pathway from PAL to CHS and DFR (Borevitz et al., 2000, Plant Cell, 12, 2383-2394; Tohge et al., 2005, Plant Journal, 42, 218-235).

In general MYBs interact closely with basic Helix Loop Helix TFs (bHLH), and this has been extensively studied in relation to the production of flavonoids (Mol et al., 1996; Winkel-Shirley, 2001). Examples include the maize ZmC MYB and ZmB bHLH and the petunia AN2 MYB and AN1/JAF13 bHLHs (Goff et al., 1992 Genes Dev, 6, 864-875; Mol et al., 1998, Trends in Plant Science, 3, 212-217). Evidently there is a degree of conservation, in different species, for this co-ordination. However, a MYB-bHLH partnership is not always necessary. Results from the overexpression of PAP1 suggested that, like the Maize P MYB (Grotewold et al., 2000 Proc Natl Acad Sci USA, 97, 13579-13584) and Arabidopsis MYB12 (Mehrtens et al., 2005 Plant Physiology, 138, 1083-1096), PAP1 did not require an over-expressed bHLH co-regulator to drive a massive increase in anthocyanin production. However, further studies showed that PAP1 does interact closely with bHLHs leading to stronger promoter (DFR) activation in in vivo assays (Zimmermann et al., 2004 Plant J, 40, 22-34). More recently, integrated transcriptome and metabolome analysis of PAP1 over-expressing lines confirmed PAP1 upregulates the bHLH TT8 (At4g09820) by 18-fold (Tohge et al., 2005, Plant J, 42, 218-235). This dependency on a co-regulator is linked to a small number of amino acid changes in the highly conserved R2R3 binding domain as evident in the comparison between the bHLH independent maize P and the bHLH dependent maize C1 MYBs, and is sufficient to direct activation of distinct sets of target genes (Grotewold et al., 2000, Proc Natl Acad Sci USA, 97, 13579-13584). In this study substitution of just six amino acids from the R2R3 domain of C1 into the corresponding positions in P1 resulted in a mutant with bHLH-dependent behaviour similar to C1. More recently it was suggested that this may be a key mechanism which permits MYBs to discriminate between target genes (Hernandez et al., 2004, J. Biol. CHem, 279, 48205-48213). These key amino acids are marked on FIG. 1. In contrast to PAP1, FaMYB1, represses anthocyanin biosynthesis during the late development of strawberry fruit. Despite this alternative role FaMYB1 shares homology with activation MYBs and can interact with (activation) bHLHs such as the *Petunia* AN1 and JAF13 (Aharoni et al., 2001, Plant J, 28, 319-332). Despite key residues being the same for PAP-like activators and FaMYB-like repressors, activators tend to fall in subgroup 10 while repressors fall in subgroup 17 (according to Stracke et al.).

An additional level of anthocyanin regulation involves a separate class of proteins, containing WD40 domains, which form complexes with MYB and bHLH proteins (as reviewed in Ramsay and Glover, 2005, Trends in Plant Science, 10, 63-70). Examples include an11 in petunia (de Vetten et al., 1997 Genes Dev, 11, 1422-1434) and TTG1 in *Arabidopsis* (Walker et al., 1999, Plant Cell, 11, 1337-1350). The transcriptional control of anthocyanins may be further complicated by tissue specific regulation (Kubo et al., 1999, Plant Cell, 11, 1217-1226) and possibly different layers of regulation dependent on stimuli such as cold, light and developmental cues (Davuluri et al., 2005, Nature Biotechnology, 23, 890-895).

Although studies into the activation and repression of anthocyanin synthesis in apple fruit have shown developmental and environmental regulation, to date transcription factors regulating anthocyanin synthesis have not been identified in this species or any other deciduous fruit. The control of anthocyanin accumulation in apple is a key question in understanding and manipulating fruit colour. Identification of the factors that exert this control provides tools for moderating the extent and distribution of anthocyanin-derived pigmentation in fruit tissue.

It is therefore an object of the invention to provide transcription factor sequences which regulate anthocyanin production in apple species and/or at least to provide the public with a useful choice.

SUMMARY OF THE INVENTION

In the first aspect the invention provides an isolated polynucleotide comprising
a) a sequence encoding a polypeptide with any one of the amino acid sequences of SEQ ID NO: 1-4 and 9-21 or a variant thereof, wherein the polypeptide or variant thereof is a transcription factor capable of regulating anthocyanin production in a plant;
b) a fragment, of at least 15 nucleotides in length, of the sequence of a);
c) the complement of the sequence of a)
d) the complement of the sequence of b)
e) a sequence, of at least 15 nucleotides in length, capable of hybridising to the sequence of
a) under stringent conditions.

In one embodiment the isolated polynucleotide comprises
a) a sequence encoding a polypeptide with at least 65% identity to any one of the amino acid sequences of SEQ ID NO: 1-4 and 9-21, wherein the polypeptide is a transcription factor capable of regulating anthocyanin production in a plant;
b) a fragment, of at least 15 nucleotides in length, of the sequence of a);
c) the complement of the sequence of a)
d) the complement of the sequence of b)
e) a sequence, of at least 15 nucleotides in length, capable of hybridising to the sequence of
a) under stringent conditions.

In a further embodiment the polypeptide has at least 65% identity to the amino acid sequence of SEQ ID NO: 1. Preferably polypeptide has the amino acid sequence of SEQ ID NO: 1.

In a further embodiment the polypeptide has at least 65% identity to the amino acid sequence of SEQ ID NO: 2. Preferably the polypeptide has the amino acid sequence of SEQ ID NO: 2.

In a further embodiment the polypeptide has at least 65% identity to the amino acid sequence of SEQ ID NO: 3. Preferably the polypeptide has the amino acid sequence of SEQ ID NO: 3.

In a further embodiment the polypeptide has at least 65% identity to the amino acid sequence of SEQ ID NO: 4. Preferably the polypeptide has the amino acid sequence of SEQ ID NO: 4.

In a further embodiment the sequence in a) has at least 70% identity to the sequence of any one of SEQ ID NO: 5-8, 22-47 and 102. Preferably the sequence in a) has at least 70% identity to the coding sequence of any one of SEQ ID NO: 5-8, 22-47 and 102.

In a further embodiment the sequence in a) has at least 70% identity to the sequence of SEQ ID NO: 5. Preferably the sequence in a) has at least 70% identity to the coding sequence of SEQ ID NO: 5. More preferably the sequence in a) has the sequence of SEQ ID NO: 5. More preferably the sequence in a) has the coding sequence of SEQ ID NO: 5.

In a further embodiment the sequence in a) has at least 70% identity to the sequence of SEQ ID NO: 6. Preferably the sequence in a) has at least 70% identity to the coding sequence of SEQ ID NO: 6. More preferably the sequence in a) has the sequence of SEQ ID NO: 6. More preferably the sequence in a) has the coding sequence of SEQ ID NO: 6.

In a further embodiment the sequence in a) has at least 70% identity to the sequence of SEQ ID NO: 7. Preferably the sequence in a) has at least 70% identity to the coding sequence of SEQ ID NO: 7. More preferably the sequence in a) has the sequence of SEQ ID NO: 7. More preferably the sequence in a) has the coding sequence of SEQ ID NO: 7.

In a further embodiment the sequence in a) has at least 70% identity to the sequence of SEQ ID NO: 8. Preferably the sequence in a) has at least 70% identity to the coding sequence of SEQ ID NO: 8. More preferably the sequence in a) has the sequence of SEQ ID NO: 8. More preferably the sequence in a) has the coding sequence of SEQ ID NO: 8.

In a further aspect the invention provides an isolated polynucleotide comprising:
a) a sequence with at least 70% identity to any one of the nucleotide sequences of SEQ ID NO: 5-8, 22-47 and 102, wherein the sequence encodes a transcription factor capable of regulating anthocyanin production in a plant;
b) a fragment, of at least 15 nucleotides in length, of the sequence of a);
c) the complement of the sequence of a)
d) the complement of the sequence of b)
e) a sequence, of at least 15 nucleotides in length, capable of hybridising to the sequence of
a) under stringent conditions.

In one embodiment the sequence in a) has at least 70% identity to the sequence of SEQ ID NO: 5. Preferably the sequence in a) has at least 70% identity to the coding sequence of SEQ ID NO: 5. More preferably the sequence in a) has the sequence of SEQ ID NO: 5. More preferably the sequence in a) has the coding sequence of SEQ ID NO: 5.

In one embodiment the sequence in a) has at least 70% identity to the sequence of SEQ ID NO: 6. Preferably the sequence in a) has at least 70% identity to the coding sequence of SEQ ID NO: 6. More preferably the sequence in a) has the sequence of SEQ ID NO: 6. More preferably the sequence in a) has the coding sequence of SEQ ID NO: 6.

In one embodiment the sequence in a) has at least 70% identity to the sequence of SEQ ID NO: 7. Preferably the sequence in a) has at least 70% identity to the coding sequence of SEQ ID NO: 7. More preferably the sequence in a) has the sequence of SEQ ID NO: 7. More preferably the sequence in a) has the coding sequence of SEQ ID NO: 7.

In one embodiment the sequence in a) has at least 70% identity to the sequence of SEQ ID NO: 8. Preferably the sequence in a) has at least 70% identity to the coding sequence of SEQ ID NO: 8. More preferably the sequence in a) has the sequence of SEQ ID NO: 8. More preferably the sequence in a) has the coding sequence of SEQ ID NO: 8.

In the further aspect the invention provides an isolated polynucleotide having at least 70% sequence identity to a nucleotide sequence that encodes a polypeptide comprising an amino acid sequence selected from any one of SEQ ID NO: 1 to 4 and 9 to 21, wherein the polynucleotide encodes a transcription factor capable of regulating anthocyanin production in a plant.

In one embodiment the isolated polynucleotide has at least 70% sequence identity to a nucleotide sequence that encodes a polypeptide comprising the amino acid sequence of SEQ ID NO.1.

In a further embodiment the nucleotide sequence comprises the nucleotide sequence of SEQ ID NO: 5. Preferably the nucleotide sequence comprises the coding sequence from SEQ ID NO: 5.

In a further aspect the invention providing an isolated polynucleotide comprising
a) a sequence encoding a polypeptide with at least 65% identity to any one of the amino acid sequences of SEQ ID NO: 1-4 and 9-21, wherein the polypeptide is a transcription factor capable of regulating the promoter of a gene in the anthocyanin biosynthetic pathway;
b) a fragment, of at least 15 nucleotides in length, of the sequence of a);
c) the complement of the sequence of a)
d) the complement of the sequence of b)
e) a sequence, of at least 15 nucleotides in length, capable of hybridising to the sequence of
a) under stringent conditions.

In a further aspect the invention provides an isolated polynucleotide comprising:
a) a sequence with at least 70% identity to any one of the nucleotide sequences of SEQ ID NO: 5-8, 22-47 and 102, wherein the sequence encodes a transcription factor capable of regulating the promoter of a gene in the anthocyanin biosynthetic pathway;
b) a fragment, of at least 15 nucleotides in length, of the sequence of a);
c) the complement of the sequence of a)
d) the complement of the sequence of b)
e) a sequence, of at least 15 nucleotides in length, capable of hybridising to the sequence of
a) under stringent conditions.

In one embodiment the gene to be regulated encodes dihydroflavolon 4-reductase (DFR).

In an alternative embodiment the gene to be regulated encodes chalcone synthase (CHS).

In a further aspect the invention provides an isolated polynucleotide comprising:
a) a sequence encoding a polypeptide variant any one of the amino acid sequences of SEQ ID NO: 1-4 and 9-21, wherein the polypeptide is a transcription factor capable of regulating anthocyanin production in a plant, and wherein the polypeptide comprises the sequence of SEQ ID NO: 101;
b) a fragment, of at least 15 nucleotides in length, of the sequence of a);
c) the complement of the sequence of a)
d) the complement of the sequence of b)
e) a sequence, of at least 15 nucleotides in length, capable of hybridising to the sequence of
a) under stringent conditions.

Preferably the variant polypeptide is derived from a Rosaceae species.

In a further aspect the invention provides an isolated polypeptide comprising:
a) a sequence with at least 65% identity to an amino acid sequence selected from any one of SEQ ID NO: 1-4 and 9-21, wherein the polypeptide is a transcription factor capable of regulating anthocyanin production in a plant; or
b) a fragment, of at least 5 amino acids in length, of the sequence of a)

In one embodiment the sequence in a) has at least 65% sequence identity to the amino acid sequence of SEQ ID NO: 1. Preferably the sequence in a) has the sequence of SEQ ID NO: 1.

In one embodiment the sequence in a) has at least 65% sequence identity to the amino acid sequence of SEQ ID NO: 2. Preferably the sequence in a) has the sequence of SEQ ID NO: 2.

In one embodiment the sequence in a) has at least 65% sequence identity to the amino acid sequence of SEQ ID NO: 3. Preferably the sequence in a) has the sequence of SEQ ID NO: 3.

In one embodiment the sequence in a) has at least 65% sequence identity to the amino acid sequence of SEQ ID NO: 4. Preferably the sequence in a) has the sequence of SEQ ID NO: 4.

In a further aspect the invention provides a polynucleotide encoding a polypeptide of the invention.

In a further aspect the invention provides an antibody raised against a polypeptide of the invention.

In a further aspect the invention provides a genetic construct comprising a polynucleotide of any one of the invention.

In a further aspect the invention provides a host cell comprising a genetic construct of the invention.

In a further aspect the invention provides a host cell genetically modified to express a polynucleotide of any one of the invention.

In a further aspect the invention provides a plant cell comprising the genetic construct of the invention.

In a further aspect the invention provides a plant cell genetically modified to express a polynucleotide of the invention.

In a further aspect the invention provides a plant which comprises the plant cell of the invention.

In a further aspect the invention provides a method for producing a polypeptide of the invention, the method comprising the step of culturing a host cell comprising an a genetic construct of the invention.

In a further aspect the invention provides a plant cell or plant with altered anthocyanin production, the method comprising the step of transformation of a plant cell or plant with a genetic construct including:
a) at least one polynucleotide encoding of a polypeptide of the invention;
b) at least one polynucleotide comprising a fragment, of at least 15 nucleotides in length, of the polynucleotide of a); or
c) at least one polynucleotide comprising a complement, of at least 15 nucleotides in length, of the polynucleotide of a).

In a further aspect the invention provides a method of producing a plant cell or plant with altered anthocyanin production, the method comprising the step of transforming a plant cell or plant with a genetic construct including:
a) at least one of the polynucleotides of any one of the invention;
b) at least one polynucleotide comprising a fragment, of at least 15 nucleotides in length, of the polynucleotide of a), or
c) at least one polynucleotide comprising a complement, of at least 15 nucleotides in length, of the polynucleotide of a)
d) at least one polynucleotide capable of hybridising under stringent conditions to the polynucleotide of a) or b).

In one embodiment of the method, the construct is designed to express a pair of transcription factors, and the construct comprises:
i) a polynucleotide sequence encoding a MYB transcription factor with at least 65% identity to the amino acid sequence of any one of SEQ ID NO: 1, 2 and 9 to 21; and
ii) a polynucleotide sequence encoding a bHLH transcription factor with at least 65% identity to the amino acid sequence of SEQ ID NO: 1 or 2.

In a further embodiment the polynucleotide sequence in i) has at least 70% sequence identity to the nucleotide sequence of any one of SEQ ID NO: 5, 6, 22 to 27 and 102; and the polynucleotide sequence in ii) has at least 70% sequence identity to the nucleotide sequence of SEQ ID NO: 7 or 8.

In a further embodiment the polynucleotide sequence in i) has at least 70% sequence identity to the nucleotide sequence of any one of SEQ ID NO: 5, 6, 22 to 27 and 102; and the coding sequence in ii) has at least 70% sequence identity to the coding sequence of SEQ ID NO: 7 or 8.

In a further aspect the invention provides a plant produced by the method of the invention.

In a further aspect the invention provides a method for selecting a plant altered in anthocyanin production, the method comprising testing of a plant for altered expression of a polynucleotide of the invention.

In a further aspect the invention provides a method for selecting a plant altered in anthocyanin production, the method comprising testing of a plant for altered expression of a polypeptide of the invention.

In a further aspect the invention provides a plant selected by the method of the invention.

In a further aspect the invention provides a method for selecting a plant cell or plant that has been transformed, the method comprising the steps
a) transforming a plant cell or plant with a polynucleotide or polypeptide of the invention capable of regulating anthocyanin production in a plant;
b) expressing the polynucleotide or polypeptide in the plant cell or plant; and
c) selecting a plant cell or plant with increased anthocyanin pigmentation relative to other plant cells or plants, the increased anthocyanin pigmentation indicating that the plant cell or plant has been transformed.

Preferably the transcription factors and variants of the invention, that are capable of regulating anthocyanin production in plants, are capable of regulating the production of the anthocyanins selected from the group including but not limited to: cyanidin-3-glucoside, cyanidin-3-0-rutinoside, cyanadin-3-glucoside and cyanadin-3-pentoside.

Preferably the plants or plant cells with altered production of anthocyanins, produced by or selected by the methods of the invention, are altered in production of anthocyanins selected from the group including but not limited to: cyanadin-3-glucosidase, cyaniding-3-0-rutinoside, cyanadin-3-glucoside and cyanadin-3-pentoside.

The polynucleotides and polynucleotide variants, of the invention may be derived from any species or may be produced by recombinant or synthetic means.

In one embodiment the polynucleotide or variant, is derived from a plant species.

In a further embodiment the polynucleotide or variant, is derived from a gymnosperm plant species.

In a further embodiment the polynucleotide or variant, is derived from an angiosperm plant species.

In a further embodiment the polynucleotide or variant, is derived from a from dicotyledonous plant species.

The polypeptides and polypeptide variants of the invention may be derived from any species, or may be produced by recombinant or synthetic means.

In one embodiment the polypeptides or variants of the invention are derived from plant species.

In a further embodiment the polypeptides or variants of the invention are derived from gymnosperm plant species.

In a further embodiment the polypeptides or variants of the invention are derived from angiosperm plant species.

In a further embodiment the polypeptides or variants of the invention are derived from dicotyledonous plant species.

In a further embodiment polypeptide or variant is derived from a monocotyledonous plant species.

The plant cells and plants of the invention may be from any species.

In one embodiment the plants cells and plants of the invention are from gymnosperm species.

In a further embodiment the plants cells and plants of the invention are from angiosperm species.

In a further embodiment the plants cells and plants of the invention are from dicotyledonous species.

In a further embodiment the plants cells and plants of the invention are from monocotyledonous species.

Preferred plant species (for the polynucleotide and variants, polypeptides and variants and plant cells and plants of the invention) include fruit plant species selected from a group comprising but not limited to the following genera: *Malus, Pyrus Prunis, Rubus, Rosa, Fragaria, Actinidia, Cydonia, Citrus*, and *Vaccinium*.

Particularly preferred fruit plant species are: *Malus domestica, Actidinia deliciosa, A. chinensis, A. eriantha, A. arguta* and hybrids of the four *Actinidia* species, *Prunis persica Pyrus* L., *Rubus, Rosa*, and *Fragaria*.

Preferred plants (for the polynucleotide and variants, polypeptides and variants and plant cells and plants of the invention) also include vegetable plant species selected from a group comprising but not limited to the following genera: *Brassica, Lycopersicon* and *Solanum*, Particularly preferred vegetable plant species are: *Lycopersicon esculentum* and *Solanum tuberosum*

Preferred plants (for the polynucleotide and variants, polypeptides and variants and plant cells and plants of the invention) also include crop plant species selected from a group comprising but not limited to the following genera: *Glycine, Zea, Hordeum* and *Oryza*.

Particularly preferred crop plant species include *Glycine max*, *Zea mays* and *Oryza sativa*.

Preferred plants (for the polynucleotide and variants, polypeptides and variants and plant cells and plants of the invention) also include those of the Rosaceae family.

Preferred Rosaceae genera include *Exochorda, Maddenia, Oeinleria, Osmaronia, Prinsepia, Prunus, Maloideae, Amelanchier, Aria, Aronia, Chaenomeles, Chamaemespilus, Cormus, Cotoneaster, Crataegus Osmaronia, Prinsepia, Prunus, Maloideae, Amelanchier, Aria, Aronia, Chaenomeles, Chamaemespilus, Cormus, Cotoneaster, Crataegu, Cydonia, Dichotomanthes, Docynia, Docyniopsis, Eriobotrya, Eriolobus, Heteromeles, Kageneckia, Lindleya, Malacomeles, Malus, Mespilus, Osteomeles, Peraphyllum, Photinia, Pseudocydonia, Pyracantha, Pyrus, Rhaphiolepis, Sorbus, Stranvaesia, Torminalis, Vauquelinia, Rosoideae, Acaena, Acomastylis, Agrimonia, Alchemilla, Aphanes, Aremonia, Bencomia, Chamaebatia, Cliffortia, Coluria, Cowania, Dalibarda, Dendriopoterium, Dryas, Duchesnea, Erythrocoma, Fallugia, Filipendula, Fragaria, Geum, Hagenia, Horkelia, Ivesia, Kerria, Leucosidea, Marcetella, Margyricarpus, Novosieversia, Oncostylus, Polylepis, Potentilla, Rosa, Rubus, Sanguisorba, Sarcopoterium, Sibbaldia, Sieversia, Taihangia, Tetraglochin, Waldsteinia, Rosaceae incertae sedis, Adenostoma, Aruncus, Cercocarpus, Chamaebatiaria, Chamaerhodos, Gillenia, Holodiscus, Lyonothamnus, Neillia, Neviusia, Physocarpus, Purshia, Rhodotypos, Sorbaria, Spiraea* and *Stephanandra*.

Preferred Rosaceae species include *Exochorda giraldii, Exochorda racemosa, Exochorda, Exochorda giraldii, Exochorda racemosa, Exochorda serratifolia, Maddenia hypoleuca, Oemleria cerasiformis, Osmaronia cerasiformis, Prinsepia sinensis, Prinsepia uniflora, Prunus alleghaniensis, Prunus americana, Prunus andersonii, Prunus angustifolia, Prunus apetala, Prunus argentea, Prunus armeniaca, Prunus avium, Prunus bifrons, Prunus brigantina, Prunus bucharica, Prunus buergeriana, Prunus campanulata, Prunus caroliniana, Prunus cerasifera, Prunus cerasus, Prunus choreiana, Prunus cocomilia, Prunus cyclamina, Prunus davidiana, Prunus debilis, Prunus domestica, Prunus dulcis, Prunus emarginata, Prunus fasciculata, Prunus ferganensis, Prunus fordiana, Prunus freinontii, Prunus fruticosa, Prunus geniculata, Prunus glandulosa, Prunus gracilis, Prunus grayana, Prunus hortulana, Prunus ilicifolia, Prunus incisa, Prunus jacquemontii, Prunus japonica, Prunus kuramica, Prunus laurocerasus, Prunus leveilleana, Prunus lusitanica, Prunus maackii, Prunus mahaleb, Prunus mandshurica, Prunus maritima, Prunus maximowiczii, Prunus mexicana, Prunus microcarpa, Prunus mira, Prunus mume, Prunus munsoniana, Prunus nigra, Prunus nipponica, Prunus padus, Prunus pensylvanica, Prunus persica, Prunus petunnikowii, Prunus prostrata, Prunus pseudocerasus, Prunus pumila, Prunus rivularis, Prunus salicina, Prunus sargentii, Prunus sellowii, Prunus serotina, Prunus serrulata, Prunus sibirica, Prunus simonii, Prunus spinosa, Prunus spinulosa, Prunus subcordata, Prunus subhirtella, Prunus takesimensis, Prunus tenella, Prunus texana, Prunus tomentosa, Prunus tschonoskii, Prunus umbellata, Prunus verecunda, Prunus virginiana, Prunus webbii, Prunus x yedoensis, Prunus zippeliana, Prunus sp. BSP-2004-1, Prunus sp. BSP-2004-2, Prunus sp. EB-2002, Amelanchier alnifolia, Amelanchier arborea, Amelanchier asiatica, Amelanchier bartramiana, Amelanchier canadensis, Amelanchier cusickii, Amelanchier fernaldii, Amelanchier florida, Amelanchier humilis, Amelanchier intermedia, Amelanchier laevis, Amelanchier lucida, Amelanchier nantucketensis, Amelanchier pumila, Amelanchier quinti-marti, Amelanchier sanguinea, Amelanchier stolonifera, Amelanchier utahensis, Amelanchier wiegandii, Amelanchier x neglecta, Amelanchier bartramiana x Amelanchier* sp. '*dentata*', *Amelanchier* sp. '*dentata*', *Amelanchier* sp. '*erecta*', *Amelanchier* sp. '*erecta*' x *Amelanchier laevis, Amelanchier* sp. '*serotina*', *Aria alnifolia, Aronia prunifolia, Chaenomeles cathayensis, Chaenomeles speciosa, Chamaemespilus alpina, Cormus domestica, Cotoneaster apiculatus, Cotoneaster lacteus, Cotoneaster pannosus, Crataegus azarolus, Crataegus columbiana, Crataegus crus-galli, Cirataegus curvisepala, Crataegus laevigata, Crataegus mollis, Crataegus monogyna, Ciatagus niga, Crataegus rivularis, Crataegus sinaica, Cydonia oblonga, Dichotomanthes tristaniicarpa, Docynia delavayi, Docyniopsis tschonoskii, Eriobotrya japonica, Eriobotrya prinoides, Eriolobus trilobatus, Heteromeles arbutifolia, Kageneckia angustifolia, Kageneckia oblonga, Lindleya mespiloides, Malacomeles denticulata, Malus angustifolia, Malus asiatica, Malus baccata, Malus coronaria, Malus doumeri, Malus florentina, Malus floribunda, Malus fusca, Malus halliana, Malus honanensis, Malus hupehensis, Malus ioensis, Malus kansuensis, Malus mandshurica, Malus micromalus, Malus niedzwetzkyana, Malus ombrophilia, Malus orientalis, Malus prattii, Malus prunifolia, Malus pumila, Malus sargentii, Malus sieboldii, Malus sieversii, Malus sylvestris, Malus toringoides, Malus transitoria, Malus trilobata, Malus tschonoskii, Malus x domestica, Malus x domestica x Malus sieversii, Malus x domestica x Pyrus communis, Malus xiaojinensis, Malus yunnanensis, Malus sp., Mespilus germanica, Osteomeles anthyllidifolia, Osteomeles schwerinae, Peraphyllum ramosissimum, Photinia fraseri, Photinia pyrifolia, Photinia serrulata, Photinia villosa, Pseudocydonia sinensis, Pyracantha coccinea, Pyracantha fortuneana, Pyrus calleryana, Pyrus caucasica, Pyrus communis, Pyrus elaeagrifolia, Pyrus hybrid cultivar, Pyrus pyrifolia, Pyrus salicifolia, Pyrus ussuriensis, Pyrus x bretschneideri, Rhaphiolepis indica, Sorbus americana, Sorbus aria, Sorbus aucuparia, Sorbus californica, Sorbus commixta, Sorbus hupehensis, Sorbus scopulina, Sorbus sibirica, Sorbus torminalis, Stranvaesia davidiana, Torminalis clusii, Vauquelinia californica, Vauquelinia corymbosa, Acaena anserinifolia, Acaena argentea, Acaena caesiiglauca, Acaena cylindristachya, Acaena digitata, Acaena echinata, Acaena elongata, Acaena eupatoria, Acaena fissistipula, Acaena inermis, Acaena laevigata, Acaena latebrosa, Acaena lucida, Acaena macrocephala, Acaena magellanica, Acaena masafuerana, Acaena montana, Acaena multifida, Acaena novaezelandiae, Acaena ovalifolia, Acaena pinnatifida, Acaena splendens, Acaena subincisa, Acaena x anserovina, Acomastylis elata, Acomastylis rossii, Acomastylis sikkimensis, Agrimonia eupatoria, Agrimonia nipponica, Agrimonia parviflora, Agrimonia pilosa, Alchemilla alpina, Alchemilla erythropoda, Alchem illa japonica, Alchemilla mollis, Alchemilla vulgaris, Aphanes arvensis, Aremonia agrimonioides, Bencomia brachystachya, Bencomia caudata, Bencomia exstipulata, Bencomia sphaerocarpa, Chamaebatia foliolosa, Cliffortia burmeana, Cliffortia cuneata, Cliffortia dentata, Cliffortia graminea, Cliffortia heterophylla, Cliffortia nitidula, Cliffortia odorata, Cliffortia ruscifolia, Cliffortia sericea, Coluria elegans, Coluria geoides, Cowania stansburiana, Dalibarda repens, Dendriopoteium menendezii, Dendriopoterium pulidoi, Dryas drummondii, Dryas octopetala, Duchesnea chrysantha, Duchesnea indica, Erythrocoma triflora, Fallugia paradoxa, Filipendula multijuga Filipendula purpurea, Filipendula ulmaria, Filipendula vulgaris, Fragaria chiloensis, Fragaria*

*daltoniana, Fragaria gracilis, Fragaria grandiflora, Fiagaria iinumae, Fragaria moschata, Fragaria nilgerrensis, Fragaria nipponica, Fragaria nubicola, Fragaria orientalis, Fragaria pentaphylla, Fragaria vesca, Fragaria virginiana, Fragaria viridis, Fragaria* x *ananassa, Fragaria* sp. *CFRA 538, Fragaria* sp., *Geum andicola, Geum borisi, Geum bulgaricum, Geum calthifolium, Geum chiloense, Geum geniculatum, Geum heterocarpum, Geum macrophyllum, Geum montanum, Geum reptans, Geum rivale, Geum schofieldii, Geum speciosum, Geum urbanum, Geum vernum, Geum* sp. *'Chase 2507 K', Hagenia abyssinica, Horkelia cuneata, Horkelia fusca, Ivesia gordoni, Kerria japonica, Leucosidea sericea, Marcetella maderensis, Marcetella moquiniana, Margyricarpus pinnatus, Margyricarpus setosus, Novosieversia glacialis, Oncostylus cockaynei, Oncostylus leiospermus, Polylepis australis, Polylepis besseri, Polylepis crista-galli, Polylepis hieronymi, Polylepis incana, Polylepis lanuginosa, Polylepis multijuga, Polylepis neglecta, Polylepis pauta, Polylepis pepei, Polylepis quadrijuga, Polylepis racemosa, Polylepis reticulata, Polylepis rugulosa, Polylepis sericea, Polylepis subsericans, Polylepis tarapacana, Polylepis tomentella, Polylepis weberbaueri, Potentilla anserina, Potentilla arguta, Potentilla bifurca, Potentilla chinensis, Potentilla dickinsii, Potentilla erecta, Potentilla fragarioides, Potentilla fruticosa, Potentilla indica, Potentilla micrantha, Potentilla multifida, Potentilla nivea, Potentilla norvegica, Potentilla palustris, Potentilla peduncularis, Potentilla reptans, Potentilla salesoviana, Potentilla stenophylla, Potentilla tridentata, Rosa abietina, Rosa abyssinica, Rosa acicularis, Rosa agrestis, Rosa alba, Rosa alba* x *Rosa corymbifera, Rosa altaica, Rosa arkansana, Rosa arvensis, Rosa banksiae, Rosa beggeriana, Rosa blanda, Rosa bracteata, Rosa brunonii, Rosa caesia, Rosa californica, Rosa canina, Rosa carolina, Rosa chinensis, Rosa cinnamomea, Rosa columnifera, Rosa corymbifera, Rosa cymosa, Rosa davurica, Rosa dumalis, Rosa ecae, Rosa eglanteria, Rosa elliptica, Rosa fedtschenkoana, Rosa foetida, Rosa foliolosa, Rosa gallica, Rosa gallica* x *Rosa dumetorum, Rosa gigantea, Rosa glauca, Rosa helenae, Rosa henryi, Rosa hugonis, Rosa hybrid* cultivar, *Rosa inodora, Rosa jundzillii, Rosa laevigata, Rosa laxa, Rosa luciae, Rosa majalis, Rosa marretii, Rosa maximowicziana, Rosa micrantha, Rosa mollis, Rosa montana, Rosa moschata, Rosa moyesii, Rosa multibracteata, Rosa multiflora, Rosa nitida, Rosa odorata, Rosa palustris, Rosa pendulina, Rosa persica, Rosa phoenicia, Rosa platyacantha, Rosa primula, Rosa pseudoscabriuscula, Rosa roxburghii, Rosa rubiginosa, Rosa rugosa, Rosa sambucina, Rosa sempervirens, Rosa sericea, Rosa sertata, Rosa setigera, Rosa sherardii, Rosa sicula, Rosa spinosissima, Rosa stellata, Rosa stylosa, Rosa subcanina, Rosa subcollina, Rosa suffulta, Rosa tomentella, Rosa tomentosa, Rosa tunquinensis, Rosa villosa, Rosa virginiana, Rosa wichurana, Rosa willmottiae, Rosa woodsii; Rosa* x *damascena, Rosa* x *fortuniana, Rosa* x *macrantha, Rosa xanthina, Rosa* sp. *Rubus alceifolius, Rubus allegheniensis, Rubus alpinus, Rubus amphidasys, Rubus arcticus, Rubus argutus, Rubus assamensis, Rubus australis, Rubus bifrons, Rubus caesius, Rubus caesius* x *Rubus idaeus, Rubus canadensis, Rubus canescens, Rubus caucasicus, Rubus chamaemorus, Rubus corchorifolius, Rubus crataegifolius, Rubus cuneifolius, Rubus deliciosus, Rubus divaricatus, Rubus ellipticus, Rubus flagellaris, Rubus fruticosus, Rubus geoides, Rubus glabratus, Rubus glaucus, Rubus gunnianus, Rubus hawaiensis, Rubus hawaiensis* x *Rubus rosifolius, Rubus hispidus, Rubus hochstetteroruni, Rubus humulifolius, Rubus idaeus, Rubus lambertianus, Rubus lasiococcus, Rubus leucodermis, Rubus lineatus, Rubus macraei, Rubus maximiformis, Rubus minusculus, Rubus moorei, Rubus multibracteatus, Rubus neomexicanus, Rubus nepalensis, Rubus nessensis, Rubus nivalis, Rubus niveus, Rubus nubigenus, Rubus occidentalis, Rubus odoratus, Rubus palmatus, Rubus parviflorus, Rubus parvifolius, Rubus parvus, Rubus pectinellus, Rubus pedatus, Rubus pedemontanus, Rubus pensilvanicus, Rubus phoenicolasius, Rubus picticaulis, Rubus pubescens, Rubus rigidus, Rubus robustus, Rubus roseus, Rubus rosifolius, Rubus sanctus, Rubus sapidus, Rubus saxatilis, Rubus setosus, Rubus spectabilis, Rubus sulcatus, Rubus tephrodes, Rubus trianthus, Rubus tricolor, Rubus trifidus, Rubus trilobus, Rubus trivialis, Rubus ulmifolius, Rubus ursinus, Rubus urticifolius, Rubus vigorosus, Rubus* sp. *JPM-2004, Sanguisorba albiflora, Sanguisorba alpina, Sanguisorba ancistroides, Sanguisorba annua, Sanguisorba canadensis, Sanguisorba filiformis, Sanguisorba hakusanensis, Sanguisorba japonensis, Sanguisorba minor, Sanguisorba obtusa, Sanguisorba officinalis, Sanguisorba parviflora, Sanguisorba stipulata, Sanguisorba tenuifolia, Sarcopoterium spinosum, Sibbaldia procumbens, Sieversia pentapetala, Sieversia pusilla, Taihangia rupestris, Tetraglochin cristatum, Waldsteinia fragarioides, Waldsteinia geoides, Adenostoma fasciculatum, Adenostoma sparsifolium, Aruncus dioicus, Cercocarpus betuloides, Cercocarpus ledifolius, Chamaebatiaria millefolium, Chamaerhodos erecta, Gillenia stipulata, Gillenia trifoliata, Holodiscus discolor, Holodiscus microphyllus, Lyonothamnus floribundus, Neillia affinis, Neillia gracilis, Neillia sinensis, Neillia sparsiflora, Neillia thibetica, Neillia thyrsiflora, Neillia uekii, Neviusia alabamensis, Physocarpus alternans, Physocarpus amurensis, Physocaipus capitatus, Physocarpus malvaceus, Physocapus monogynus, Physocarpus opulifolius, Purshia tridentata, Rhodotypos scandens, Sorbaria arborea, Sorbaria sorbifolia, Spiraea betulifolia, Spiraea cantoniensis, Spiraea densiflora, Spiraea japonica, Spiraea nipponica, Spiraea* x *vanhouttei, Spiraea* sp. *Stephanandra chinensis, Stephanandra incisa* and *Stephanandra tanakae.*

Particularly preferred Rosaceae genera include: *Malus, Pyrus, Cydonia, Prunus, Eriobotrya,* and *Mespilus.*

Particularly preferred Rosaceae species include: *Malus domestica, Malus sylvestris, Pyrus communis, Pyrus pyrifolia, Pyrus bretschneideri, Cydonia oblonga, Prunus salicina, Prunus cerasifera, Prunus persica, Eriobotrya japonica, Prunus dulcis, Prunus avium, Mespilus germanica* and *Prunus domestica.*

More particularly preferred Rosaceae genera include *Malus* and *Prunus*

Particularly preferred Rosaceae species include *Malus domestica* and *Prunus cerasifera.*

The term "plant" is intended to include a whole plant, any part of a plant, propagules and progeny of a plant.

The term 'propagule' means any part of a plant that may be used in reproduction or propagation, either sexual or asexual, including seeds and cuttings.

DETAILED DESCRIPTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term comprising, and grammatical equivalents thereof, is intended to mean "consisting at least in part of . . . ".

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol. Lett. 174:247-250), which is publicly available from NCBI (available on the world wide web at ftp.ncbi.nih.gov/blast/). The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P., Longden, I. and Bleasby, A. EMBOSS: The European Molecular Biology Open Software Suite, Trends in Genetics June 2000, vol. 16, No. 6. pp. 276-277) which is available on the world wide web at www.hgmp.mrc.ac.uk/Software/EMBOSS/. The European Bioinformatics Institute server also provides the facility to perform EMBOSS-needle global alignments between two sequences on the world wide web at www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (available on the world wide web at ftp.ncbi.nih.gov/blast/).

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81.5+0.41% (G+C−log(Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (available on the world wide web at ftp.ncbi.nih.gov/blast/) via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (available on the world wide web at ftp.ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available on the world wide web at www.ebi.ac.uk/emboss/align/) and GAP (Huang, X. (1994) On Global Sequence Alignment. Computer Applications in the Biosciences 10, 227-235) as discussed above are also suitable global sequence alignment programs for calculating polypeptide sequence identity.

A preferred method for calculating polypeptide sequence identity is based on aligning sequences to be compared using Clustal W (Thompson et al 1994, Nucleic Acid Res 11 (22) 4673-4680)

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (available on the world wide web at ftp.ncbi.nih.gov/blast/). The similarity of polypeptide sequences may be examined using the following unix command line parameters:

bl2seq -i peptideseq1 -j peptideseq2 -F F -p blastp

Variant polypeptide sequences preferably exhibit an E value of less than $1\times10^{-6}$, more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-80}$, more preferably less than $1\times10^{-70}$, more preferably less than $1\times10^{-80}$, more preferably less than $1\times10^{-90}$ and most preferably $1\times10^{-100}$ when compared with anyone of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed,
 b) the polynucleotide to be expressed, and
 c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

A "transgenic plant" refers to a plant which contains new genetic material as a result of genetic manipulation or transformation. The new genetic material may be derived from a plant of the same species as the resulting transgenic plant or from a different species.

An "inverted repeat" is a sequence that is repeated, where the second half of the repeat is in the complementary strand, e.g.,

```
(5')GATCTA.......TAGATC(3')
(3')CTAGAT.......ATCTAG(5')
```

Read-through transcription will produce a transcript that undergoes complementary base-pairing to form a hairpin structure provided that there is a 3-5 bp spacer between the repeated regions.

The term "regulating anthocyanin production" is intended to include both increasing and decreasing anthocyanin production. Preferably the term refers to increasing anthocyanin production. Anthocyanins that may be regulated include but are not limited to cyanindin-3-glucoside, cyaniding-3-0-rutinoside, cyanadin-3-galactoside and cyanadin-3-pentoside.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

The applicants have identified polynucleotide sequences (SEQ ID NO: 5 to 8) which encode polypeptides (SEQ ID NO: 1 to 4) respectively from apple, which are transcription factors capable of regulating anthocyanin production in plants. The applicants have also identified polynucleotide variants (SEQ ID NO: 22 to 47) of SEQ ID NO: 5 that encode polypeptide variants (SEQ ID NO: 9 to 21) of SEQ ID NO: 1. A summary of the relationship between the polynucleotides and polypeptides is found in Table 3 (Summary of Sequences).

The invention provides genetic constructs, vectors and plants comprising the polynucleotide sequences. The invention also provides plants comprising the genetic constructs and vectors of the invention.

The invention provides plants altered, relative to suitable control plants, in production of anthocyanin pigments. The invention provides both plants with increased and decreased production of anthocyanin pigments. The invention also provides methods for the production of such plants and methods of selection of such plants.

Suitable control plants may include non-transformed plants of the same species and variety, or plants of the same species or variety transformed with a control construct.

Uses of the compositions of the invention include the production of fruit, or other plant parts, with increased levels of anthocyanin pigmentation, for example production of apples with red skin and or red flesh.

The invention also provides methods for selecting transformed plant cells and plants by selecting plant cells and plants which have increased anthocyanin pigment, the increased anthocyanic pigment indicating that the plants are transformed to express a polynucleotide or polypeptide of the invention.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1× SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX (which are publicly available on the world wide web at ftp.ncbi.nih.gov/blast/ or from the National Center for Biotechnology Information (NCBI), National Library of Medicine, Building 38A, Room 8N805, Bethesda, Md. 20894 USA). The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, available on the world wide web at www-igbmc.u-strasbg.fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302: 205-217) or PILEUP, which uses progressive, pairwise alignments (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (available on the world wide web at www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

The function of a variant polynucleotide of the invention as encoding a transcription factor capable of regulating pigment production in a plant transcription factors can be tested for this ability to regulate expression of known anthocyanin biosynthesis genes (e.g. Example 4) or can be tested for their capability to regulate pigment production (e.g. Examples 5 and 6).

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, *Guide to Protein Purification*).

Alternatively the polypeptides and variant polypeptides of the invention may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Production of plants altered in pigment production may be achieved through methods of the invention. Such methods may involve the transformation of plant cells and plants, with a construct of the invention designed to alter expression of a polynucleotide or polypeptide capable of regulating pigment production in such plant cells and plants. Such methods also include the transformation of plant cells and plants with a combination of the construct of the invention and one or more other constructs designed to alter expression of one or more polypeptides or polypeptides capable of regulating pigment production in such plant cells and plants.

Methods for transforming plant cells, plants and portions thereof with polypeptides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'        3'CTAGAT 5'  (antisense strand)
(coding strand)

3'CUAGAU 5' mRNA   5'GAUCUCG 3' antisense RNA
```

Genetic constructs designed for gene silencing may also include an inverted repeat. An 'inverted repeat' is a sequence that is repeated where the second half of the repeat is in the complementary strand, e.g.,

```
5'-GATCTA.........TAGATC-3'

3'-CTAGAT.........ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve over-expression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792, 935); soybean (U.S. Pat. Nos. 5,416,011; 5,569,834; 5,824, 877; 5,563,055 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463,174 and 5,750,871); cereals (U.S. Pat. No. 6,074,877); pear (Matsuda et al., 2005); *Prunus* (Ramesh et al., 2006; Song and Sink 2005; Gonzalez Padilla et al., 2003); strawberry (Oosumi et al., 2006; Folta et al., 2006), rose (Li et al., 2003), and Rubus (Graham et al., 1995). Transformation of other species is also contemplated by the invention. Suitable methods and protocols are available in the scientific literature.

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

Methods of Selecting Plants

Methods are also provided for selecting plants with altered pigment production. Such methods involve testing of plants for altered for the expression of a polynucleotide or polypeptide of the invention. Such methods may be applied at a young age or early developmental stage when the altered pigment production may not necessarily be visible, to accelerate breeding programs directed toward improving anthocyanin content.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered levels of anthocyanin. The polypeptides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate flower size in plants. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with altered expression are useful in conventional breeding programs designed to produce varieties with altered pigment production.

Plants

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

BRIEF DESCRIPTION OF THE DRAWINGS

The present invention will be better understood with reference to the accompanying drawings in which:

FIG. 1 shows comparison of the MdMYB10 (SEQ ID NO:1) and MdMYB9 (SEQ ID NO:2) with known anthocyanin MYB regulators from various species at the R2R3 binding domain. Arrows indicate specific residues that contribute to a motif implicated in bHLH cofactor interaction in *Arabidopsis* (Zimmermann et al, 2000); these same residues are evidence in MdMYB10 and MdMYB9 suggesting a similar protein-protein interaction. The sequences are: MdMYB10 apple (SEQ ID NO: 103), AtPAP1 (SEQ ID NO: 104), AtMYB90 (SEQ ID NO: 105), VlMYBA2 (SEQ ID NO: 106), Ca A pepper (SEQ ID NO: 107), PhAN2 (SEQ ID NO: 108), LeANT1 (SEQ ID NO: 109), GhMYB10 Gerbera (SEQ ID NO: 110), PmBF1 spruce (SEQ ID NO: 111), ZmC1 maize (SEQ ID NO: 112), AtTT2 AtMYB123 (SEQ ID NO: 113), MdMYB9 apple (SEQ ID NO: 114), MdMYB11 apple (SEQ ID NO: 115), ZmP maize (SEQ ID NO: 116), MdMYB8 apple (SEQ ID NO: 117) and AtGL1 (SEQ ID NO: 118).

(B) shows microscope images showing pattern of anthocyanin (darker grey) accumulation in tobacco leaf tissue infiltrated with MdMyb10+ MdbHLH3 at 20× (left) and 40× (right). Scale bars represent 50 microns.

Figure 7:
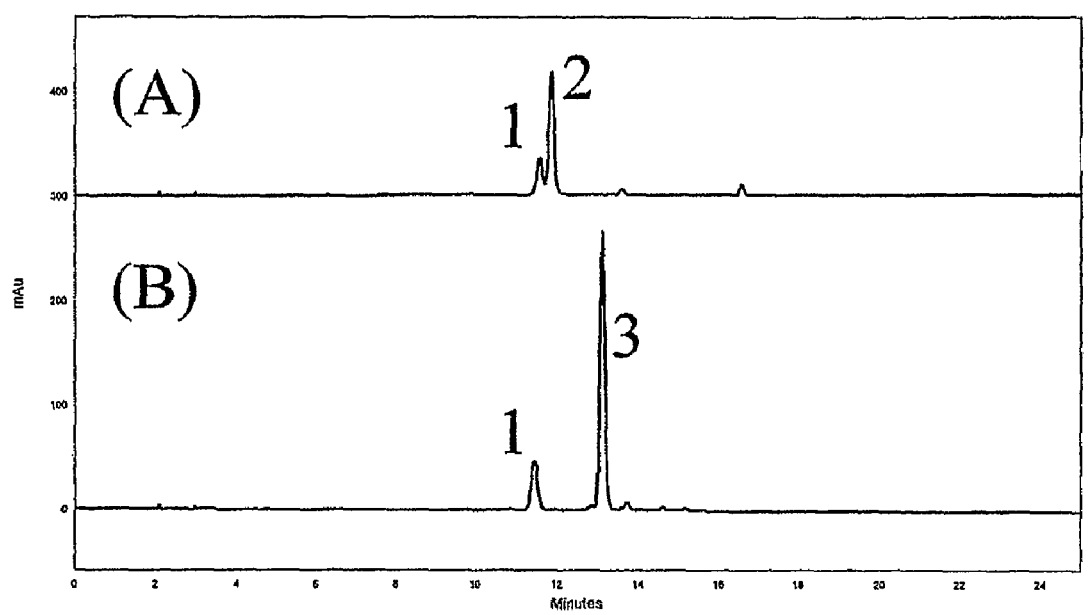

FIG. 7 shows HPLC traces showing (A) *Nicotiana tabaccum* petal and (B) *Nicotiana tabaccum* leaf infiltrated with MdMYB10+MdbHLH3. 1, cyanidin-3-glucoside 2, petunidin-3-galactoside, 3 cyanidin-3-0-rutinoside. No peaks were observed in control tobacco leaf (data not shown).

FIG. 8 shows protein sequence alignment of the MdMyb10 polypeptide sequence with polypeptide variants of MdMYBI0 and AtPAPI (also called AtMYB75) for reference. The accession number of AtMYB75 in the GenBank database is CAB09230. The alignment was created using the Clustal W algorithm (Thompson et al., 1994). The sequences are: AtMYB75 (SEQ ID NO: 119), Co Quince—SEQ ID NO:13), Ej (loquat—SEQ ID NO:17), Md (apple—SEQ ID NO:1), Ms (crab a—SEQ ID NO:9), Pb (pear Y—SEQ ID NO:12 Pc (pear—SEQ ID NO:10), Pcf (cherry—SEQ ID NO:15), Ppr (peach—SEQ ID NO:16), Pc (pear—SEQ ID NO:11), Ps (Japane—SEQ ID NO:14), Pav (sweet—SEQ ID NO:19), Pd (almond—SEQ ID NO:18), Mg (medlar—SEQ ID NO: 20) and Pdm (Europ—SEQ ID NO: 21).

FIG. 9 shows % sequence identity between the MdMyb10 polypeptide sequence, polypeptide variants of MdMYB10 and AtPAP1 for reference. The table shows % identity values for all possible sequence combinations for the sequences that are included in FIG. 8.

Figure 10:
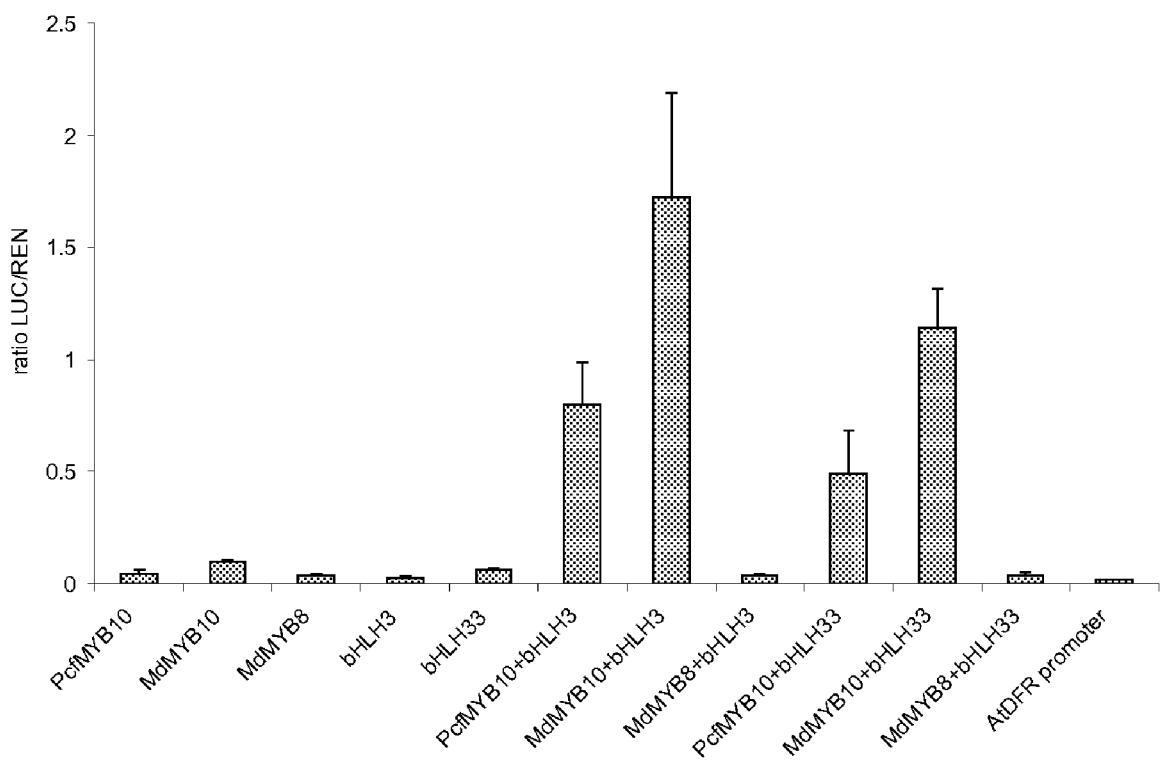
Figure 11:
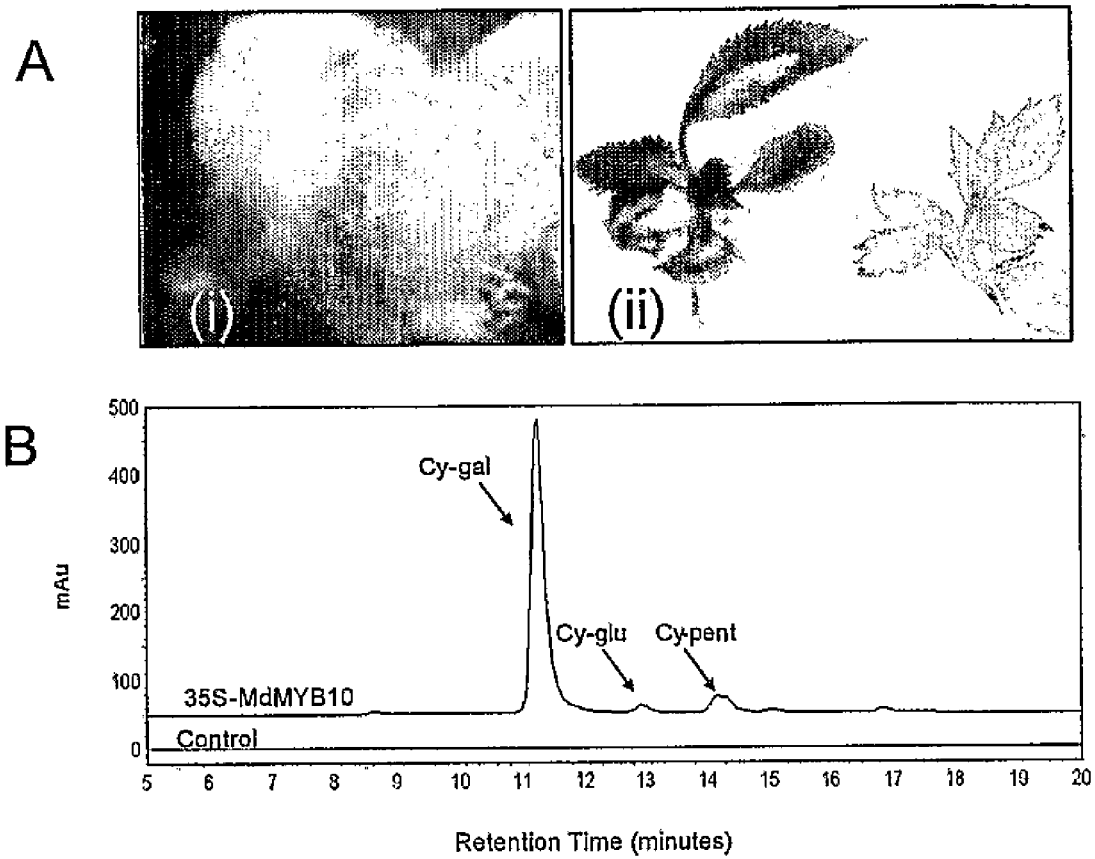

FIG. 10 shows activiation of the At-DFR gene promoter by MdMYB10 and PcfMYB10 (a variant of PcfMYB10) in combination with apple bHLH TFs in tobacco transient transformation assays affects the activity of the At-DFR gene promoter. The dual luciferase assay shows promoter activity as expressed as a ratio of DFR promoter luciferase (LUC) to 35S Renilla (REN) where an increase in activity equates to an increase in LUC relative to REN. The effects of combinations of MYB transcription factors (Md MYB10, Pcf MYB10 and MdMYB8 (−ve control) with bHLH transcription factors Md bHLH 3 and MdbHLH33 are shown. Error bars shown are means±S.E. of 6 replicate reactions FIG. 11 shows that over-expression of MdMYB10 in apple cells and/or plants elevates anthocyanin production. (A)(i) shows pigmented callus cells. A (ii) shows an apple plant transformed with 35S-MdMYB10 (left) and empty vector control plant (right). The plant transformed with 35-Md-MYB10 clearly shows strong pigmentation compared to the empty vector control. (B) Shows an anthocyanin profiles of extracts of 35S-MdMYB10 apple leaf (top line) and empty vector control (bottom line). Peaks identified from HPLC traces at 520 nm; cy-gal, cyanidin-3-galactoside, with minor traces of cy-glu, cyanidin-3-glucoside and cy-pent, cyanidin-3-pentoside.

EXAMPLES

The invention will now be illustrated with reference to the following non-limiting examples.

Example 1

Identification of an Appropriate Apple Tissue and Developmental Stage useful for the Isolation of Polynucleotides Encoding Transcription Factors which Regulate Pigment Production Materials and Methods
Real Time (qPCR) Expression Analysis Apple fruit were collected at 6 time points during the apple fruit season from spring (October) through summer to (March) 2003-2004: October (7 days after fall bloom, DAFB), November (40 DAFB), December (67 DAFB), January (102 DAFB), February (130 DAFB) and March (146 DAFB) from trees at the HortResearch orchard (Nelson, New Zealand). RNA was isolated (adapted from Chang et al., 1993) from the fruit (six fruit from the same tree, skin and cortex separately) and the leaves of 2 genotypes; the white-fleshed commercial cultivar *Malus domestica* var. Sciros (Pacific Rose™, derived from a cross between Gala and Splendour) and the red-fleshed cultivar *Malus domestica* var. Red Field, an open-pollinated seedling of the cultivar 'Redfield' (a cross between 'Wolf River' and *Malus domestica* var. Niedzwetzkyana (Brooks and Olmo, 1972). For the first developmental fruit time point, October (7 DAFB), successful excision of skin from cortex was not possible and data from this sample has been excluded. First strand cDNA synthesis (three replicates for each sample which were subsequently pooled) was preceded by DNase treatment and performed using oligo dT according to the manufacturers instructions (Transcriptor, Roche Applied Science).

Genes encoding apple anthocyanin pathway enzymes and regulators were identified by homology in the HortResearch EST database and, in the case of possible isoforms, selection was made according to the expression profile and library tissue. Gene specific primers, corresponding to these genes were designed using Vector NTI version 9.0.0 (available on the world wide web at www.invitrogen.com) to a stringent set of criteria, enabling application of universal reaction conditions. To check reaction specificity, RT-PCR was used according to manufacturer's instructions (Platinum Taq, Invitrogen). The sequence of each primer pair and the relevant accession number are shown in supplementary Table 1 below.

TABLE 1

| Gene identifier | Gene name | Forward primer (SEQ ID NO:) | Reverse primer (SEQ ID NO:) |
|---|---|---|---|
| CN944824 | MdCHS | GGAGACAACTGGAGAAGGACTGG (81) | AACGACATTGATACTGGTGTCTTCA (82) |
| CN946541 | MdCHI | GGGATAACCTCGCGGCCAAA (83) | GCATCCATGCCGGAAGCTACAA (84) |
| CN491664 | MdF3H | TGGAAGCTTGTGAGGACTGGGGT (85) | CTCCTCCGATGGCAAATCAAAGA (86) |
| AY227729 | MdDFR | GATAGGGTTTGAGTTCAAGTA (87) | TCTCCTCAGCAGCCTCAGTTTTCT (88) |
| AF117269 | MdLDOX | CCAAGTGAAGCGGGTTGTGCT (89) | CAAAGCAGGCGGACAGGAGTAGC (90) |
| AF117267 | MdUFGT | CCACCGCCCTTCCAAACACTCT (91) | CACCCTTATGTTACGCGGCATGT (92) |
|  | MdMYB10 | TGCCTGGACTCGAGAGGAAGACA (93) | CCTGTTTCCCAAAAGCCTGTGAA (94) |
|  | MdbHLH33 | ATGTTTTTGCGACGGAGAGAGCA (95) | TAGGCGAGTGAACACCATACATTAAAGG (96) |
| CN934367 | MdbHLH3 | AGGGTTCCAGAAGACCACGCCT (97) | TTGGATGTGGAGTGCTCGGAGA (98) |
| CN938023 | MdActin | TGACCGAATGAGCAAGGAAATTACTTACTCAGCTTTGGCAATCCACATC (99) | (100) |

DNA amplification and analysis was carried out using the LightCycler System (Roche LightCycler 1.5). All reactions were performed with the LightCycler FastStart SYBR Green Master Mix (Roche Applied Science) following the manufacturer's method. Reactions were performed in triplicate using 2 µl 5× Master Mix, 0.5 µM each primer, 1 µl diluted cDNA and nuclease-free water (Roche Applied Science) to a final volume of 10 µl. A negative water control was included in each run. The following thermal profile was used for all qPCR reactions: a pre-incubation step at 95° C. for 5 minutes followed by 40 cycles of 95° C. (5 seconds), 60° C. (5 seconds) and 72° C. (10 seconds). Fluorescence was measured at the end of each annealing step. Amplification was followed by a melting curve analysis with continual fluorescence data acquisition during the 65° C. to 95° C. melt. The raw data was analysed with the LightCycler software version 4 and expression was normalised to *Malus domestica* Actin (MdActin, accession CN938023) with the Pacific Rose leaf sample acting as calibrator with a nominal value of 1. For each gene a standard curve was generated with a cDNA serial dilution and the resultant PCR efficiency calculations (ranging between 1.839 and 1.945) were imported into relative expression data analysis.

Results qPCR Expression Analysis of Biosynthetic Enzymes

Figure 3:
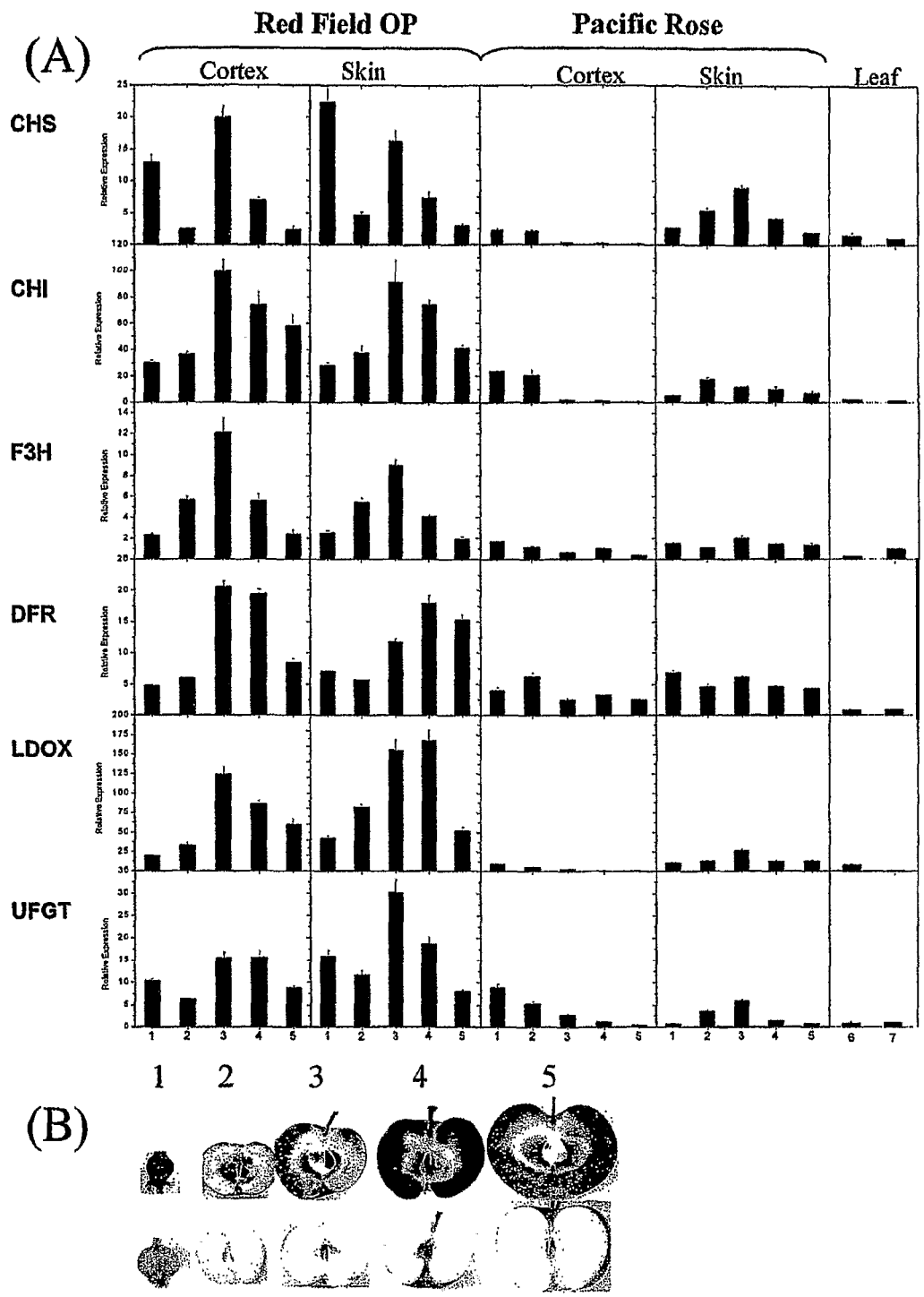
FIG. 3(A) shows data from qPCR analysis of the apple anthocyanin biosynthetic genes from CHS to UFGT as listed on the right hand side in the cortex, skin and leaf on Red Field and Pacific Rose. X axis numbers refer as follows; 1, 40DAFB, 2, 67 DAFB, 3, 102DAFB, 4, 130DAFB, 5, 146 DAFB, 6, Red Field OP leaf and 7, Pacific Rose leaf.
FIG. 3(B) shows sections through apple fruit (Red Field OP in upper row, Pacific Rose in lower row) at developmental stages 1 to 5 as in 3(A). Increased pigmentation is Red Field OP versus Pacific Rose is visibly apparent.

In order to identify the stage of fruit development, where transcriptional regulation of anthocyanin synthesis is greatest, the analysis of expression of the major biosynthetic genes was performed. A comparison of transcript levels encoding anthocyanin biosynthetic genes between Pacific Rose and Red Field shows striking differences. In all the genes assayed, representing the majority of the enzymatic steps in the pathway, transcript levels in Red Field showed significant elevation during all stages of fruit development in comparison to the levels found in Pacific Rose (FIG. 3).

Transcript abundance of the biosynthetic genes in Red Field was enhanced throughout fruit development in both skin and cortex, with a general pattern indicating the highest transcript levels at the January time point. This configuration mimics the degree of pigmentation observed during tissue sampling with the most intense pigmentation being observed early in development (40 DAFB) and then again in mid-summer (102 DAFB), a level that is subsequently sustained through to fruit maturation in late summer (FIG. 3 *b*). In Pacific Rose cortex tissue there was comparatively low transcript level for all the anthocyanin biosynthesis genes, with a general decline in expression during fruit development. Moderate activity was observed in the skin with a peak of expression midway through development at 102 DAFB, concomitant with enhanced levels of pigmentation during fruit maturation. The level of expression in the leaves of both varieties was evident but relatively low with little to distinguish between Red Field and Pacific Rose.

Results from qPCR analysis of anthocyanin biosynthetic enzyme transcript levels were analysed to determine the most suitable tissue/time point for relevant MYB transcription factor isolation. We chose tissue from Red Field cortex, that showed the highest expression level for the anthocyanin biosynthesis genes.

Example 2

Isolation of Polynucleotides Encoding Transcription Factors Potentially Regulating Pigment Production in Apple PCR was performed using cDNA from the cortex sample of Red Field (January time point) using degenerate primers (with a 32 fold degeneracy) designed at the R2R3 binding domain based on the sequence of anthocyanin regulators in diverse species. Numerous cDNAs encoding R2R3 MYB domains were obtained. Results from sequencing data revealed one cDNA with high identity to anthocyanin regulators and full length sequence was obtained using 5' RACE (GeneRacer, Invitrogen). The complete sequence for the MdMYB10 cDNA was compiled from overlapping fragments. To compare the transcript from Red Field, full length cDNAs were subsequently isolated from *Malus domestica* vars. Pacific Rose and Granny Smith. MdMYB11 (DQ074463), a subgroup 11 MYB (according to Stracke et al. 2001) was also isolated and sequenced by the same process. Other transcription factor candidates were isolated from the HortResearch EST collection: MdMYB9 an apple homologue of *Arabidopsis* TT2 (Nesi et al., 2001, AJ299452), and MdMYB8, an apple MYB bearing little sequence homology to known anthocyanin regulators.

Previous studies in other species have shown that a subgroup 10 MYB may be the key determinant of pigmentation. Within publicly available apple EST databases (185,000 nucleotide sequences as at August 2005), there is no MYB TF showing high homology via sequence blasts to *Arabidopsis* PAP1 and subgroup 10 MYBs from other species.

Figure 1:
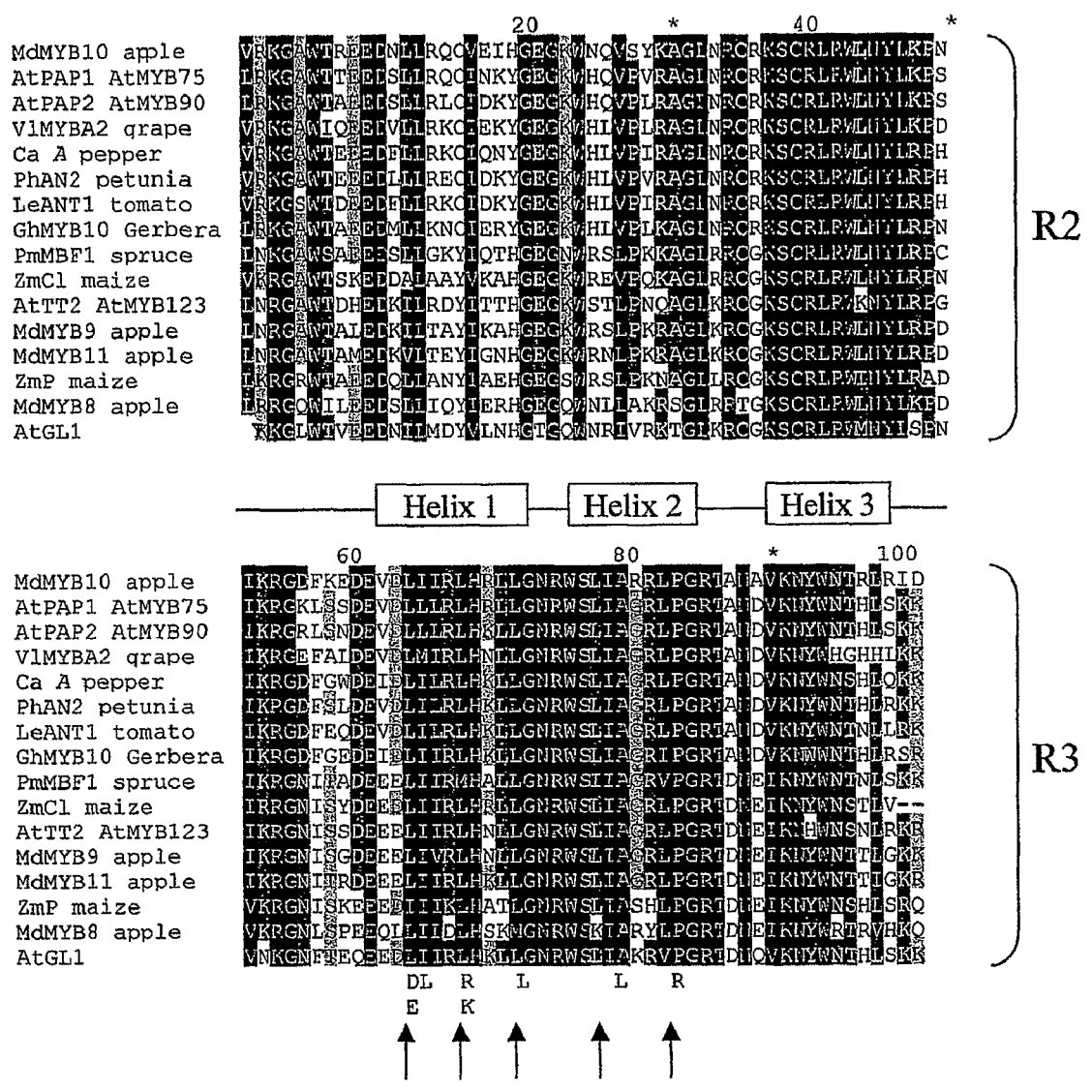

Overlapping sequence alignments of cDNAs cloned after PCR show that the best candidate, MdMYB10, shares a high degree of homology with other MYB TFs at the R2R3 domain and, in particular, with anthocyanin regulators from other species (FIG. 1). MdMYB10 is closely related to the *Arabidopsis* subgroup 10 MYB, PAP 1, with a 77% amino acid identity at the R2R3 binding domain and 58% overall. For *Arabidopsis* PAP2 these amino acid percentage identities are 75% and 57% respectively whilst for other species figures for overall identity are as follows: Petunia AN2 60%, Tomato ANT1 57%, Maize C1 5%, and Maize P 26%.

All these MYB TFs have the amino acid residues that specify interaction with bHLHs (Grotewold et al., 2000). Candidates for these cofactors were therefore selected from the HortResearch EST database. In the large phylogenetic family with constitutes the bHLH type TF, there is a smaller lade termed IIIf (Heim et al., 2003) that appears to be involved in the regulation of flavonoid biosynthesis. Two apple TFs from the HortResearch EST database clustered within this lade (data not shown). These were sequenced to full length and given the identifiers MdbHLH3 (CN934367), a putative homologue of the *Arabidopsis* TT8 gene and MdbHLH33, a putative homologue of Delila (from Antirrhinum, Goodrich et al., 1992).

Phylogeny

Apple EST sequences were trimmed of vector, adapter and low quality sequence regions and uploaded to Vector NTI version 9.0.0 (available on the world wide web at www.invitrogen.com). The EST clustering phase was performed using Vector NTI AlignX program. Alignments were then exported to GeneDoc version 2.6.002 (available on the world wide web at www.psc.edu/biomed/genedoc/) as MSF format files. Trees were generated by re-aligning exported files in CLUSTALX (v1.81) using the default settings (Thompson et al., 1997). Phylogenetic analysis was carried out using the PHYLIP software package (Felsenstein, 1993). TreeView (v.1.6.5) was used to display resulting trees (Page, 1996) or circular trees were generated using MEGA version 2.1 (Kumar et al., 2001).

Example 3

Identification of Variants of the MdMyb10

Tissue was collected from *Malus domestica*, *Malus sylvestris* (Ms, European crab apple), *Pyrus communis* (Pc, pear),

*Pyrus pyrifolia* (Ppy pear, Nashi), *Pyrus bretschneideri* (Pb, pear, YAL1), *Cydonia oblonga* (Co, quince), *Prunus salicina* (Ps, Japanese plum, prune), *Prunus cerasifera* (Pcf, cherry plum), *Prunus persica* (Ppr, peach), *Eriobotrya japonica* (Ej, loquat), *Prunus dulcis* (Pd, almond), *Prunus avium* (Pav, sweet cherry), *Mespilus germanica* (Mg, medlar), *Prunus domestica* (Pdm, European plum) *Rubus idaeus* (Ri, red raspberry), *Prunus armeniaca* (par, apricot), and *Prunus insititia* (Pi, Damson) all of which are rosaceae species.

Genomic DNA (gDNA) was extracted, using DNeasy Plant Mini Kit (QIAGEN, catalogue 69104) according to manufactures instructions, from leaves of each species, except for *Pyrus pyrifolia* (Ppy pear, Nashi), *Pyrus bretschneideri* (Pb, pear, YALI) where genomic DNA was isolated from fruit peel.

PCR was performed on gDNA from the above species (by standard techniques) using combinations of the primers shown in Table 2 below.

TABLE 2

| Primer | Sequence (5' to 3') | SEQ ID NO: |
|---|---|---|
| RE73 degenerate primer) F | AAAAGTTGCAGACTTAGATGGTTGAATT ATTTGAAGCC | 48 |
| RE77R | GAGAATCGATCCGCAATCGAQTGTTCC | 49 |
| RE78R | ACCACCTGTTTCCCAAAAGCCTGTGAAGTCT | 50 |
| RE79R | CACAAGCTAGATGGTACCACAGAAGTGAGAATC | 51 |
| RE95F | TAAGAGATGGAGGGATATAACG | 52 |
| RE96R | CTAGCTATTCTTCTTTTGAATGATTC | 53 |
| RE108F | GATCGATTCTCGCATGAAAACGGT | 54 |
| RE109R | GACGACGTTTGTGGTGGCGTACT | 55 |
| RE120F | TGCCTGGACTCGAGAGGAAGACA | 56 |
| RE121R | CCTGTTTCCCAAAAGCCTGTGAA | 57 |
| KL Ms1F | CTTATAATTAGACTTCACAGGC | 58 |
| KL Ms2R | CACCGTTTTCATGCGAGAAT | 59 |
| KL . Md PAP1F | GCAGATAAGAGATGGAGGGATATAACGA AAACCTGAG | 60 |
| KL MdPAP1R | TACACAAGCTAGATGGTACCACAGAAGT GAGAATC | 61 |
| KL PcfF | GACTTTATGGAAGATGAAGTAGATC | 62 |
| KL PcfR | AAGCGATAGTATATTATTGATGAAC | 63 |
| KL Pct2F | CTTGGGTGTGAGAAAAGGAG | 64 |
| KL Pcf3R | CACGCTAAAAGAGAAATCAC | 65 |
| KL Pcf4R | GCTTGTGAAGCCTAATTATT | 66 |
| KL Ppr1F | GAAAGATAAAGCCCAAGAAA | 67 |
| KL Ppr2R | TTTGAACTCTTGATGAAGCT | 68 |
| KL Ppr3F | CTGCGAATTTGTATTGTATGTC | 69 |
| KL Ppr4R | TTCCCACCAATCATTTCCAT | 70 |
| KL Fv1F | AAGAGAGGAGAGTTTGCAGAGG | 71 |
| KL Fv2R | TAGTTCTTCACATCATTGGCAG | 72 |
| KL Fv6R | AATATGCACCAGGAAGTCTTAAAGA | 73 |
| KL Fv7F | AAATCTGCTTAATTTTCATGGAGGG | 74 |
| KL Rh1F | TCAGAGAGAGAGAGATGGGTGGTATTCC | 75 |
| KL Rh2R | CTTCCTCTTGTTCAAAGCTCCCTCTC | 76 |
| KL Rh3F | AGAACTATTGGAATTGTCACTTGAG | 77 |
| KL Rh4R | AGAATAAAATCACTTTCATAACCAC | 78 |
| KL Rosa deg 1F (degenerate primer with a 64 fold degeneracy) | AGACTTCCRGGAAGRACWGCNAAT GMTGTG | 79 |
| KL Rosa deg 2R (degenerate primer with a 16 fold degeneracy) | CCARTAATTTTTCACAKCATTNGC | 80 |

Genomic PCR products were sequenced by standard procedures.

From sequenced genomic DNA, intron and exons were predicted by known methods of comparison with MdMYB10 EST data, known intron/exon boundaries, and open reading frames. From these deduced cDNAs, translated protein was generated. A summary of the variant gDNA, predicted cDNA and predicted polypeptide sequences identified is included in Table X. Polypeptide variants of MdMyb10 are listed in the sequence listing as SEQ ID NO: 9-21. Polynucleotide variants of MdMyb10 are listed in the sequence listing as SEQ ID NO: 22-47. SEQ ID NO: 102 is a MdMyb10 genomic sequence.

The variant polypeptide sequences (together with MdMyb10 and AtPAP1 for reference) were aligned using Vector NTI version 9.0, which uses a Clustal W algorithm (Thompson et al., 1994). Results are shown in FIG. 8

Percentage sequence identity between the aligned polypeptide sequences was also calculated using Vector NTI version 9.0 ((Sep. 2, 2003 ©1994-2003 InforMax, now licenced to Invitrogen) Results are shown in FIG. 9.

These data show that the applicants have identified a distinct group MdMYB10 variants from rosaceae species. The rosaceae sequences share a significant degree of sequence conservation, and each rosaceae sequence is more similar to another rosaceae sequence than it is to AtPAP1.

Example 4

Activation of Pigment Promoters by Expression of Transcription Factor Polynucleotides of the Invention in Plants Dual Luciferase Assay Promoter sequences were inserted into the cloning site of pGreen 0800-LUC (Hellens et al., 2005) and modified to introduce an NcoI site at the 3' end of the sequence, allowing the promoter to be cloned as a transcriptional fusion with the firefly luciferase gene (LUC). Thus, TFs that bind the promoter and increase the rate of transcription could be identified by an increase in luminescence activity. Arabidopsis CHS (TT4) (AT5g13930) and Arabidopsis DFR (TT3) (AT5g42800) were isolated from genomic DNA. In the same construct, a luciferase gene from Renilla (REN) under the control of a 35S promoter provided an estimate of the extent of transient expression. Activity is expressed as a ratio of LUC to REN activity so that where the interaction between a TF (+/−bHLH) and the promoter occurred, a significant increase in the LUC activity relative to REN would be observed.

Nicotiana benthamiana were grown under glasshouse conditions, using natural light with daylight extension to 16 hrs, until at least 6 leaves (of 2-3 cm in length) were available for infiltration with Agobacterium. Plants were maintained in the glasshouse for the duration of the experiment. Agrobacterium strain GV3101(MP90) was cultured on Lennox agar (Invitrogen) supplemented with selection antibiotics and incubated at 28° C. A 10 µl loop of confluent bacterium were re-suspended in 10 ml of infiltration media (10 mM $MgCl_2$, 0.5 µM acetosyringone), to an $OD_{600}$ of 0.2, and incubated at room temperature without shaking for 2 h before infiltration. Infiltrations were performed according to the methods of Voinnet et al. (2003). Approximately 150 µl of this Agrobacterium mixture was infiltrated at six points into a young leaf of N. benthamiana and transient expression was assayed 3 days after inoculation.

The promoter-LUC fusions (CHS and DFR) in pGreenII 0800-LUC were used in transient transformation by mixing 100 µl of Agrobacterium transformed with the reporter cassette with two other Agrobacterium strains (450 µl each) transformed with cassettes containing a MYB TF gene fused to the 35S promoter and a bHLH TF gene in either pART27 (Gleave, 1992) or pGreenII 62-SK binary vectors (Hellens et al., 2000).

Firefly luciferase and renilla luciferase were assayed using the dual luciferase assay reagents (Promega, Madison, USA). Three days after inoculation, 2 cm leaf discs (6 technical replicates from each plant) were removed and ground in 500 µl of passive lysis buffer (PLB). Ten µl of a 1/100 dilution of this crude extract was assayed in 40 µl of luciferase assay buffer, and the chemiluminescence measured. 40 µl of Stop and Glow™ buffer was then added and a second chemiluminescence measurement made. Absolute relative luminescence units (RLU) were measured in a Turner 20/20 luminometer, with a 5 s delay and 15 s measurement.

Dual Luciferase Assay

Figure 2:
FIG. 2 shows a phylogenetic analysis showing relationship between *Arabidopsis* and apple MYB TFs. Arrow shows position of MdMYB10 which falls next to AtPAP1 in the Anthocyanin MYB regulator subgroup 10. Known anthocyanin regulators are denoted by a grey dot, other genes included in figure with a black dot are negative controls showing MdMYB10 action is specific for this MYB clade and not MYBs in general.

The dual luciferase system has been demonstrated to provide a rapid method of transient gene expression analysis (Hellens et al., 2005). It requires no selectable marker and results can be quantified with a simple enzymatic assay. In this study the system was used to quantify the activity of the promoters of anthocyanin biosynthetic genes when challenged with TFs which putatively bind the promoters. We used N. benthamiana for the dual luciferase transient assay to test the interaction of our candidate TFs with two Arabidopsis anthocyanin biosynthesis gene promoters, AtCHS (TT4, AT5g13930) and AtDFR (TT3, AT5g42800), that are known to be regulated by Arabidopsis PAP1 and PAP2 MYB TFs (Tohge et al., 2005, Zimmermann et al., 2004). Several apple MYB TFs were selected to probe the specificity of MdMYB10: MdMYB9, MdMYB11, MdMYB8 and, from Arabidopsis, AtPAP1. These MYBs fall into clades representing subgroups 10, 9, 11 and 7 respectively (FIG. 2). To interrogate the interaction between MYB and bHLH TFs co-transformation was performed with bHLH class putative regulators from apple; MdbHLH3 and MdbHLH33 and from Arabidopsis the bHLH, TT8 (AtbHLH042; At4g09820).

Figure 5:
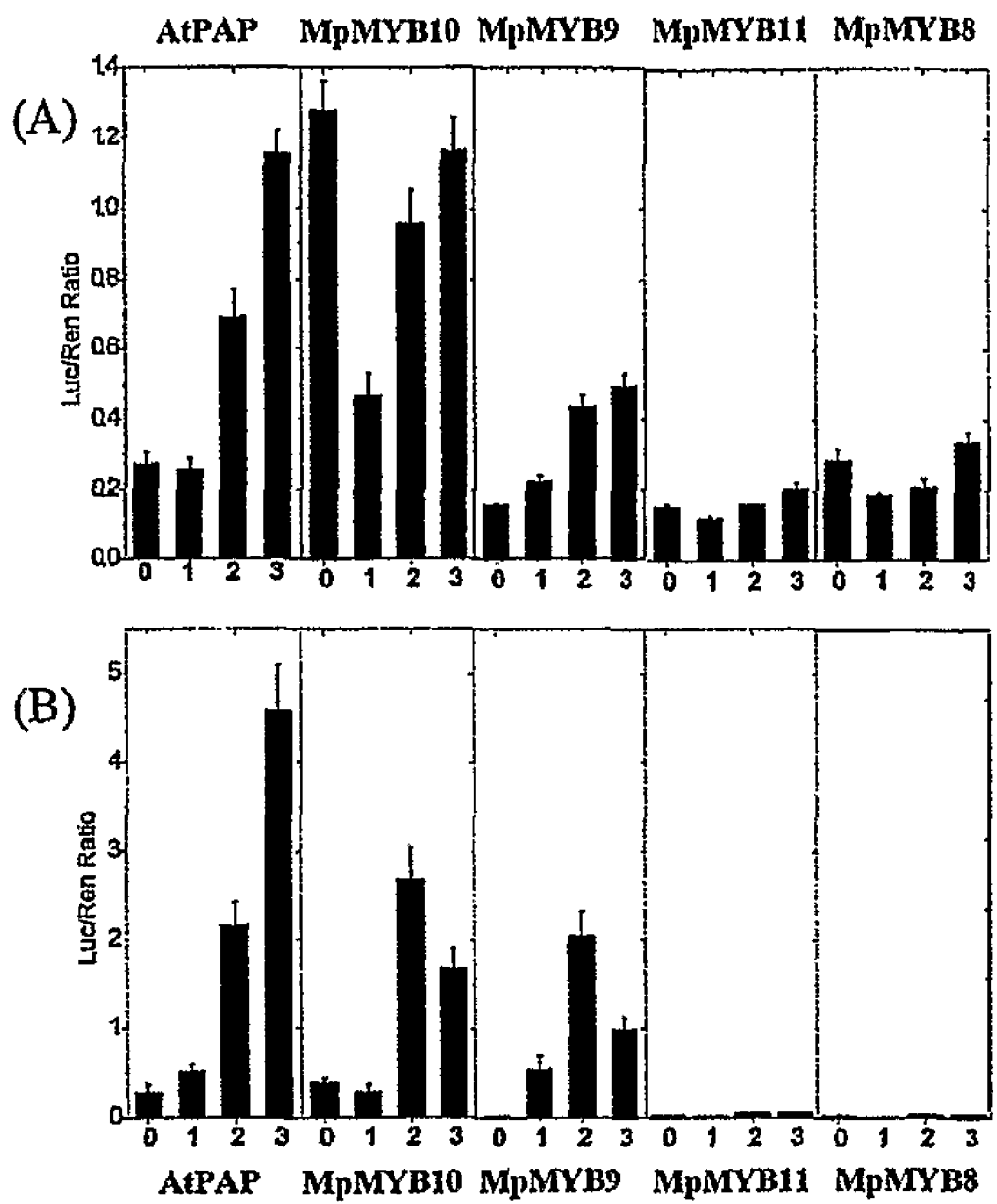
FIG. 5 shows the dual luciferase assay shows promoter activity as expressed as a ratio of LUC to REN where an increase in activity equates to an increase in LUC relative REN for a combination of MYB TFs with/without bHLH TFs; (A) Arabidopsis TT4 (CHS)-Luc promoter, (B) Arabidopsis TT3 (DFR)-Luc promoter. 0, MYB along, 1, MYB+AtTT8, 2, MYB+MdbHLH3, 3, MYB+MdbHLH33.

Results from transient analysis based on the CHS promoter showed that activity of the Arabidopsis PAP1 MYB was greatest in co-transformation with an apple bHLH, but was unexpectedly not affected by co-transformation with the Arabidopsis TT8 bHLH. In contrast, results for MdMYB10 indicates activity that may be independent of a bHLH with the highest activity observed with the MYB alone (FIG. 5). Co-transformation of MdMYB10 with the Arabidopsis bHLH appeared to inhibit activity. MdMYB9 also showed enhanced activity when in partnership with either of the apple bHLHs, consistent with its sequence similarity to TT2-like genes. Significant activity for the remaining MYBs was not observed and this degree of activity presumably represents basal levels.

Results from the DFR promoter assay show a different pattern indicating a significant increase in activity when MdMYB10 (and AtPAP1) was co-transformed with an apple bHLH. In the case of the MdMYB10 the highest activity was observed when infiltrated with MdbHLH3. This contrasted with AtPAP1 where activity was highest when infiltrated with the apple Delila homologue, MdbHLH33. These results reflect previous work in a transient protoplast transfection system where in an Arabidopsis DFR promoter:Gus fusion was only activated by PAP1 in the presence of a bHLH (Zimmermann et al., 2004), although it should be noted that we did not see such large increases in activity when AtPAP1 was infiltrated with AtTT8. MdMYB9 performed in a similar but reduced manner, whilst the LUC to REN ratio for MdMYB11 and MdMYB8 was low under all conditions.

When genomic cherry plum MYB10 (PcfMYB10) was cloned into a pGREEN plasmid vector and assayed as described above, activation of the DFR promoter results. Highest activity is shown when PcfMYB10 is infiltrated with MdbHLH3 and MdbHLH33 (FIG. 10). This data shows that a MYB10 sequence from the Amygdaloideae or Prunoideae sub-family is also effective at driving anthocyanin gene activity in a similar mechanism to MdMYB10 (of the Malus sub-family of Rosaceae).

Example 5

Activation of Pigment Biosynthesis by Expression of Transcription Factors of the Invention in Plants Colour Assay Nicotiana tabacum var. Samsun were grown in a glass house at 22° C., using natural light with daylight extension to 16 hrs, until at least 3 leaves (of 10-15 cm in length) were available for infiltration with Agrobacterium. Plants were maintained in the glasshouse for the duration of the experiment. Agrobacterium cultures were incubated as for the dual luciferase assay and separate strains containing the MYB TF gene and the bHLH TF gene fused to the 35S promoter in pART27 binary vector were mixed (500 µl each) and infiltrated into the lower leaf surface as for the assay with N. benthamiana. Six separate infiltrations were performed into N. tabacum leaves (two plants per treatment) and changes in colour were measured daily using a Minolta CR-300 chromametre (calibrated to D65 light) using the L*a*b* system (CIE, 1986). Infiltrations comprising MdMYB10 together with an apple bHLH resulted in visible pigmentation after four days. The level of pigmentation increased throughout the experimental period; digital photographs and microscope images were taken eight days after infiltration. Anthocyanin pigmentation did not develop when N. benthamiana was used in parallel assays (data not shown).

HPLC

*N. tabaccum* leaf discs were excised around the infiltration sites, freeze-dried and coarsely ground before re-suspension in 5 ml methanol and 0.1% HCL, extracted at room temperature for 2 hours and centrifuged at 3500 rpm. Aliquots of 1 ml were dried down to completion in a Labconco Centrivap Concentrator. Samples were re-suspended in 20% methanol (250 μl). Anthocyanins were characterized by HPLC on a 250×4.6 mm, Synergi, 4 m particle size, Polar-RP, 80 Å pore size, ether-linked phenyl column (Phenomenex, Auckland, New Zealand). This was fitted to a Shimadzu analytical HPLC with a column oven, auto-sampler, vacuum solvent degasser and diode-array detector. Solvents were (A) acetonitrile+0.1% formic acid and (B) acetonitrile/water/formic acid, 5:92:3. Flow rate was 1.5 ml/min and column temperature 45° C. The content of solvent A was 0% at 0 time and ramped linearly to 17% at 17 min, 20% at 20 min, 30% at 26 min, 50% at 28.5 min, 95% between 32-35 min and back to 0% between 36-42 min. Quantification of reaction products was at 520 nm for anthocyanins and 280 nm for other phenolics. Spectra were recorded from 240-600 nm in 4 nm steps. Sample injection volume was 40 μL.

Colour Assay

Figure 6:
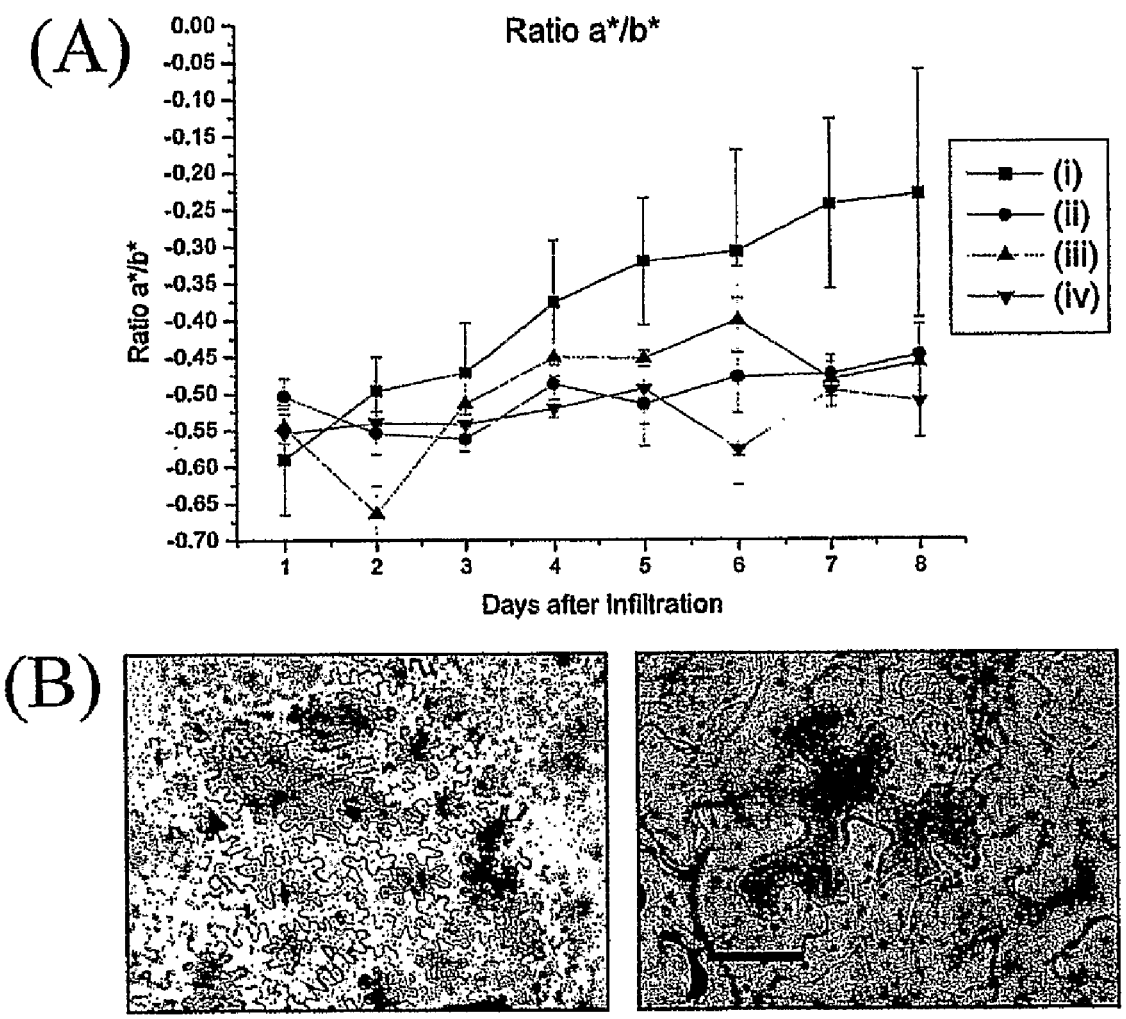
FIG. 6 shows data from transient assay in *Nicotiana tobaccum*. (A) shows colour measurement by Minolta chromameter as shown as a*/b* ratio. A shift towards positive indicates a colour change from green towards red. (i) MdMYB10+MdbHLH3, (ii) MdMYB10 alone.

We have established a simple method to reveal anthocyanin pigment accumulation in *N. tabacum* via *Agrobacterium* infiltration. Accumulation of pigmentation in *N. tabacum* infiltrated leaves was examined visually. Pigmentation was evident at infiltration points as early as four days post-infiltration for MdMYB10 when co-infiltrated with an apple bHLH (FIG. 6A). The degree of pigmentation increased over the experimental period (of up to ten days). Pigmentation was also observed but at reduced levels in treatments comprising co-infiltration of AtPAP1 and an apple bHLH (MdbHLH3 or MdbHLH33), AtPAP1 and AtTT8, and, to a lesser extent, with infiltration of MdMYB10 alone. No pigmentation was visible in other combinations. Results demonstrate the efficacy of this assay as a useful reporter system to study the regulation of the pigmentation process.

Colour was quantified by measurement with a Minolta chromameter using the L*a*b* system confirmed the visible transition from green to red. The data is shown as a ratio of a*/b* (FIG. 6B), where the change from negative towards positive indicates a shift from green to red. There was variability between replicates of a given treatment as to the extent of pigmentation as apparent in the depth of error bars (FIG. 6B).

To verify cellular build-up of anthocyanin compounds, microscope images were obtained from epidermal peels 1 week after inoculation (FIG. 6C). This illustrates the transformation of individual cells with the candidate genes and activation of the accumulation of anthocyanin pigments within the vacuoles.

Analysis of HPLC Data

To confirm the identity of the anthocyanins synthesised during tobacco transient expression of selected MYBs, samples were extracted and the soluble anthocyanins analysed by HPLC. The results indicate that when MdMYB10 and MdbHLH3 are co-overexpressed in tobacco leaves, two major peaks are observed, representing cyanidin-3-glucoside and cyanidin-3-0-rutinoside (FIG. 7). These compound identities were confirmed by LC-MS (data not shown). No observable anthocyanin peaks were found in the extracts of tobacco leaf transformed with empty vector control (data not shown). To compare this with compounds naturally occurring in apple and tobacco, anthocyanins from the petals of tobacco and skin of apple (Pacific Rose, mature fruit) were also extracted and results confirmed the predominance of cyanidin-3-galactoside in apple skin (data not shown) but as previously described (Tsou et al. 2003). Cyanidin-3-glucoside and petunidin-3-galactoside was observed in tobacco petal (FIG. 7). Petunidin-3-galactoside is not seen in the profile generated in a tobacco leaf by the action of MdMYB10 and MdbHLH3(FIG. 7).

qPCR Expression Analysis of Transcription Factors

Figure 4:
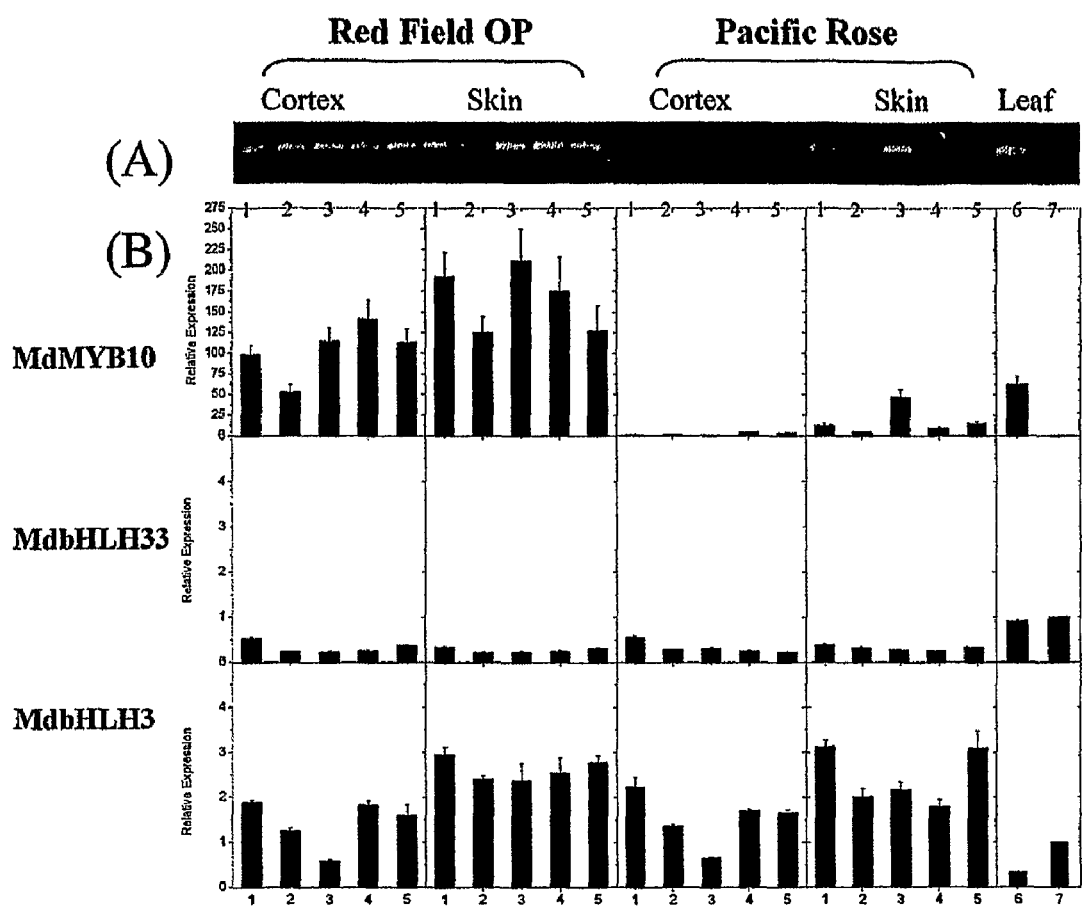
FIG. 4 shows an expression analysis of MdMYB10, MdbHLH3 and MdbHLH33. (A) RT-PCR analysis of MDMYB10 in Red Field (cortex, skin and leaf) and Pacific Rose (cortex, skin and leaf) and (B) corresponding qPCR data of MdMYB10, MdbHLH3 and MdbHLH33. Gel lane and x axis number as follows; 1, 40 DAFB, 2, 67 DAFB, 3, 102 DAFB, 4, 130 DAFB, 5, 146 DAFB, 6, Red Field leaf and 7, Pacific Rose leaf.

Knowledge of the abundance, and pattern of accumulation, of biosynthetic gene transcripts provided information as to the most appropriate tissue with which to perform degenerate PCR for the isolation of a putative transcriptional regulator. qPCR of the TFs in this same development series reveals increases in the relative transcript levels of MdMYB10 in the fruit tissues of Red Field compared to Pacific Rose. In cortex tissue, transcript levels in Pacific Rose were barely detectable, whilst in the skin Pacific Rose transcript was evident and levels of the MYB transcript correlate with the biosynthetic enzymes particularly at the January time point and in relation to UFGT. Expression levels of MdMYB10 in Red Field appear to largely follow the transcript pattern of the enzymes assayed, with highly elevated levels throughout fruit tissues, particularly at the November time point and then again at January, February and March (FIG. 4B). Transcript levels in Red Field leaf were similarly elevated in comparison to Pacific Rose. Results were similar for RT-PCR (FIG. 4A) and to further confirm specificity, qPCR amplicons were sequenced and analysed and found to encode MdMYB10.

Transcript levels of MdbHLH3 and MdbHLH33 did not appear to follow the pattern displayed for the biosynthetic genes, or for MdMYB10 with a more consistent level of expression both throughout the development series and in both varieties (FIG. 4B). Transcript levels of the MdMYB8, MdMYB9 and MdMYB11 genes were also assayed but did not show a correlative pattern with the anthocyanin enzyme transcript levels (data not shown).

Example 6

Over-Expression of MdMyb10 in Transgenic Apple Plants Results in Elevated Anthocyanin Production Transformation of Apple The binary vector pSAK277-MdMYB10 containing the MdMYB10 cDNA driven by the Cauliflower mosaic virus 35S promoter produced by standard techniques was transferred into *Agrobacterium tumefaciens* strain GV3101 by the freeze-thaw method well-known to those skilled in the art. Transgenic *Malus domestica* 'Royal Gala' plants were generated by *Agrobacterium*-mediated transformation of leaf pieces, using a method previously reported (Yao et al., 1995). Control plants transformed with an equivalent empty vector were also produced in the same way.

The results are shown in FIG. 11.

Highly pigmented callus cells are shown in A(i). A(ii) shows a highly pigmented 35-5 Mym10 plant (left) and an empty vector control plant for comparison (right).

Panel B shows anthocyanin profiles (generated as described in Example 5) of extracts from 35S-MdMyB10 and control plants. Results shows levels of anthocyanin pigments are clearly detectable in the 35S-MdMYB10 plants but not in the control plants. Apple tissue was extracted in acidified methanol and peaks identified from HPLC traces at 520 nm; cy-gal, cyaniding-3-galactoside, with minor traces of cy-glu, cyaniding-3-glucoside and cy-pent, cyaniding-3-pentoside.

It is not the intention to limit the scope of the invention to the above mentioned examples only. As would be appreciated by a skilled person in the art, many variations are possible without departing from the scope of the invention.

REFERENCES

Aharoni A, De Vos C H, Wein M, Sun Z, Greco R, Kroon A, Mol J N, O'Connell A P (2001) The strawberry FaMYB1 transcription factor suppresses anthocyanin and flavonol accumulation in transgenic tobacco. Plant J 28: 319-332

Borevitz J O, Xia Y, Blount J, Dixon R A, Lamb C (2000) Activation tagging identifies a conserved MYB regulator of phenylpropanoid biosynthesis. Plant Cell 12: 2383-2394

Boss P K, Davies C, Robinson S P (1996). Expression of anthocyanin biosynthesis pathway genes in red and white grapes. Plant Mol Biol 32: 565-569

Boyer J, Liu R (2004) Apple phytochemicals and their health benefits. Nutrition Journal 3: 5

Brooks, R M, Olmo, H. P. (1972). Register of New Fruit and Nut Varieties. University of California Press, London.

Broun P (2005). Transcriptional control of flavonoid biosynthesis: a complex network of conserved regulators involved in multiple aspects of differentiation in *Arabidopsis*. Curr Opin Plant Biol 8: 272-279

Brouillard R (1988). Flavonoids and flower colour. In J B Harborne, ed, The Flavonoids: Advances in Research since 1980. Chapman & Hall, London, pp 525-538

Chang, S., Puryear, J. and Cairney, J. (1993). A simple and efficient method for isolating RNA from pine trees. Plant Mol. Biol. Rep. 11: 113-116.

CIE (1986) Colorimetry, $2^{nd}$ edn. Publication CIE No. 15.2, Central Bureau of the Commission Internationale de L'Eclairage, Viena.

Davies K M, Schwinn K E (2003) Transcriptional regulation of secondary metabolism. Functional Plant Biology 30: 913-925

Davuluri G R, van Tuinen A, Fraser P D, Manfredonia A, Newman R, Burgess D, Brummell D A, King S R, Palys J, Uhlig J, Bramley P M, Pennings H M J, Bowler C (2005) Fruit-specific RNAi-mediated suppression of DET1 enhances carotenoid and flavonoid content in tomatoes. Nature Biotechnology 23: 890-895 de Vetten N, Quattrocchio F, Mol J, Koes R (1997) The an11 locus controlling flower pigmentation in petunia encodes a novel WD-repeat protein conserved in yeast, plants, and animals. Genes Dev 11: 1422-1434

Dixon R A, Steele C L (1999) Flavonoids and isoflavonoids—a gold mine for metabolic engineering. Trends Plant Sci 4: 394-400

Dong Y H, Mitra D, Kootstra A, Lister C, Lancaster J (1998) Postharvest stimulation of skin colour in royal gala apple. J Am Soc Hortic Sci 120: 95-100

Elomaa P, Uimari A, Mehto M, Albert V, Laitinen R, Teeri T (2003) Activation of anthocyanin biosynthesis in *Gerbera hybrida* (Asteraceae) suggests conserved protein-protein and protein-promoter interactions between the anciently diverged monocots and eudicots. Plant Physiology and Biochemistry 133: 1831-1842

Folta K M, Dhingra A, Howard L, Stewart P J, Chandler C K. (2006) Characterization of LF9, an octoploid strawberry genotype selected for rapid regeneration and transformation. Planta. 2006 Apr. 14; PMID: 16614818

Gleave A (1992) A versatile binary vector system with a T-DNA organisational structure conducive to efficient integration of cloned DNA into the plant genome. Plant Molecular Biology 20: 1203-1207

Goff S A, Cone K C, Chandler V L (1992) Functional analysis of the transcriptional activator encoded by the maize B gene: evidence for a direct functional interaction between two classes of regulatory proteins. Genes Dev 6: 864-875

Gonzalez Padilla I M, Webb K, Scorza R. (2003) Early antibiotic selection and efficient rooting and acclimatization improve the production of transgenic plum plants (*Prunus domestica* L.). Plant Cell Rep. 22(1):38-45.

Goodrich J, Carpenter R, Coen E S (1992) A common gene regulates pigmentation pattern in diverse plant species. Cell 68: 955-964

Graham J, McNicol R J, Kumar A. (1995) *Agrobacterium*-mediated transformation of soft fruit *Rubus, Ribes*, and *Fragaria*. Methods Mol Biol. 1995; 44:129-33.

Grotewold E, Sainz M B, Tagliani L, Hernandez J M, Bowen B, Chandler V L (2000) Identification of the residues in the Myb domain of maize C1 that specify the interaction with the bHLH cofactor R. Proc Natl Acad Sci USA 97: 13579-13584

Harborne J B, Grayer R J (1994) Flavonoids and insects. In J B Harborne, ed, The Flavonoids: Advances in Research Since 1986. Chapman & Hall, London, p 589-618

Heim M A, Jakoby M, Werber M, Martin C, Bailey P C, Weisshaar B (2003) The basic helix-loop-helix transcription factor family in plants: a genome-wide study of protein structure and functional diversity. Molecular Biology and Evolution 20: 735-747

Hellens R P, Edwards E A, Leyland N R, Bean S, Mullineaux P M (2000) pgreen: a versatile and flexible binary Ti vector for *Agrobacterium*-mediated plant transformation. Plant Mol. Biol. 42: 819-832

Hellens R P, Allan A C, Friel E N, Bolitho K, Grafton K, Templeton M D, Karunairetnam S, Laing W A (2005) Transient plant expression vectors for functional genomics, quantification of promoter activity and RNA silencing. Plant Methods In press Hernandez J M, Heine G F, Irani N G, Feller A, Kim M-G, Matulnik T, Chandler V L, Grotewold E (2004) Different mechanisms participate in the R-dependent activity of the R2R3 MYB transcription factor C1. J. Biol. Chem. 279: 48205-48213

Holton T A, Cornish E C (1995) Genetics and biochemistry of anthocyanin biosynthesis. Plant Cell 7: 1071-1083

Honda C, Kotoda N, Wada M, Kondo S, Kobayashi S, Soejima J, Zhang Z, Tsuda T, Moriguchi T (2002) Alithocyanin biosynthetic genes are coordinately expressed during red coloration in apple skin. Plant Physiology and Biochemistry 40: 955-962

Li X, Gasic K, Cammue B, Broekaert W, Korban S S (2003) Transgenic rose lines harboring an antimicrobial protein gene, Ace-AMP1, demonstrate enhanced resistance to powdery mildew (*Sphaerotheca pannosa*). Planta. 218(2): 226-32.

Jin H, Martin C (1999) Multifunctionality and diversity within the plant MYB-gene family. Plant Mol Biol 41: 577-585

Kim S-H, Lee J-R, Hong S-T, Yoo Y-K, An G, Kim S-R (2003) Molecular cloning and analysis of anthocyanin biosynthesis genes preferentially expressed in apple skin. Plant Science 165: 403-413

Kobayashi S, Ishimaru M, Hiraoka K, Honda C (2002) Myb-related genes of the Kyoho grape (*Vitis labruscana*) regulate anthocyanin biosynthesis. Planta 215: 924-933

Kobayashi S, Goto-Yamamoto N, Hirochika H (2004) Retrotransposon-induced mutations in grape skin color. Science 304: 982

Koes R E, Quattrocchio F, Mol J N M (1994) The flavonoid biosynthetic pathway in plants: Function and evolution. BioEssays 16: 123-132

Koes R, Verweij W, Quattrocchio F (2005) Flavonoids: a colorful model for the regulation and evolution of biochemical pathways. Trends in Plant Science 10: 236-242

Kumar S, Tamura K, Jakobsen I B, M. N (2001) MEGA2: molecular evolutionary genetics analysis software. Bioinformatics 17: 1244-1245

Kubo H, Peeters A J M, Aarts M G M, Pereira A, Koornneef M (1999) *Anthocyanless*2, a homeobox gene affecting anthocyanin distribution and root development in *Arabidopsis*. Plant Cell 11: 1217-1226

Lancaster J (1992) Regulation of skin color in apples. Crit. Rev. Plant Sci. 10: 487-502

Lister C E, J. E. Lancaster (1996) Developmental changes in enzymes of flavonoid biosynthesis in the skins of red and green apple cultivars. J Sci Food Agric: 313-320

Matsuda N, Gao M, Isuzugawa K, Takashina T, Nishimura K. (2005) Development of an *Agrobacterium*-mediated transformation method for pear (*Pyrus communis* L.) with leaf-section and axillary shoot-meristem explants. Plant Cell Rep. 24(1):45-51.

Mol J, Grotewold E, Koes R (1998) How genes paint flowers and seeds. Trends in Plant Science 3: 212-217

Mol J J, G; Schafer, E; Weiss, D (1996) Signal perception, transduction, and gene expression involved in anthocyanin biosynthesis. Critical Reviews in Plant Sciences.: 525-557

Mehrtens F, Kranz H, Bednarek P, Weisshaar B (2005) The *Arabidopsis* transcription factor MYB12 is a flavonol-specific regulator of phenylpropanoid biosynthesis. Plant Physiology 138: 1083-1096

Nesi N, Jond C, Debeaujon I, Caboche M, L L (2001) The Arabidopsis TT2 gene encodes an R2R3 MYB domain protein that acts as a key determainant for proanthocyanidin accumulation in developing seed. Plant Cell 13: 2099-2114

Noda K-i, Glover B J, Linstead P, Martin C (1994) Flower colour intensity depends on specialized cell shape controlled by a Myb-related transcription factor. 369: 661-664

Oosumi T, Gruszewski H A, Blischak L A, Baxter A J, Wadl P A, Shuman J L, Veilleux R E, Shulaev V. (2006) High-efficiency transformation of the diploid strawberry (*Fragaria vesca*) for functional genomics. Planta.; 223(6): 1219-30.

Page R (1996) Comput. Applic. Biosci 12: 357-358

Piazza P, Procissi A, Jenkins G I, Tonelli C (2002) Members of the c1/pl1 regulatory gene family mediate the response of maize aleurone and mesocotyl to different light qualities and cytokinins. Plant Physiol 128: 1077-1086

Quattrocchio F, Wing J F, van der Woude K, Mol J N, Koes R (1998) Analysis of bHLH and MYB domain proteins: species-specific regulatory differences are caused by divergent evolution of target anthocyanin genes. Plant J 13: 475-488

Ramesh S A, Kaiser B N, Franks T, Collins G, Sedgley M. (2006) Improved methods in *Agrobacterium*-mediated transformation of almond using positive (mannose/pmi) or negative (kanamycin resistance) selection-based protocols. Plant Cell Rep. 25(8):821-8.

Ramsay N A, Glover B J (2005) MYB-bHLH-WD40 protein complex and the evolution of cellular diversity. Trends in Plant Science 10: 63-70

Saito K, Yamazaki M (2002) Biochemistry and molecular biology of the late-stage of biosynthesis of anthocyanin: lessons from *Perilla frutescens* as a model plant. New Phytologist 155: 9-23

Schwinn K E, Davies K M (2004) Flavonoids. In K M Davies, ed, Plant pigments and their manipulation, Vol 14. Blackwell, Oxford Song G Q, Sink K C. (2005) Transformation of Montmorency sour cherry (*Prunus cerasus* L.) and Gisela 6 (*P. cerasus* x *P. canescens*) cherry rootstock mediated by *Agrobacterium tumefaciens*. Plant Cell Rep. 2006; 25(2):117-23

Stracke R, Werber M, Weisshaar B (2001) The R2R3-MYB gene family in *Arabidopsis thaliana*. Current Opinion in Plant Biology 4: 447-456

J D Thompson, D G Higgins, and T J Gibson (1994) CLUSTAL W: improving the sensitivity of progressive multiple sequence alignment through sequence weighting, position-specific gap penalties and weight matrix choice. *Nucleic Acids Res.* 1; 22(22): 4673-4680.

Thompson J D, Gibson T J, Plewniak F, Jeanmougin F, Higgins D G (1997) The ClustaiX windows interface: flexible strategies for multiple sequence alignment aided by quality analysis tools. Nucleic Acids Research 24: 4876-4882

Tohge T, Nishiyama Y, Hirai MY, Yano M, Nakajima J, Awazuhara M, Inoue E, Takahashi H, Goodenowe D B, Kitayama M, Noji M, Yamazaki M, Saito K (2005) Functional genomics by integrated analysis of metabolome and transcriptome of Arabidopsis plants over-expressing an MYB transcription factor. Plant J 42: 218-235

Tsao R, Yang R, Young J C, Zhu H (2003) Polyphenolic profiles in eight apple cultivars using high-performance liquid chromatography (HPLC). J Agric Food Chem 51: 6347-6353

Voinnet O, Rivas S, Mestre P, Baulcombe D (2003) An enhanced transient expression system in plants based on suppression of gene silencing by the p19 protein of tomato bushy stunt virus. Plant J 33: 949-956

Vom Endt D, Kijne J W, Memelink J (2002) Transcription factors controlling plant secondary metabolism: what regulates the regulators? Phytochemistry 61: 107-114

Walker A R, Davison P A, Bolognesi-Winfield A C, James C M, Srinivasan N, Blundell T L, Esch J J, Marks M D, Gray J C (1999) The TRANSPARENT TESTA GLABRA1 locus, which regulates trichome differentiation and anthocyanin biosynthesis in Arabidopsis, encodes a WD40 repeat protein. Plant Cell 11: 1337-1350

Winkel-Shirley B (2001) Flavonoid biosynthesis. A colorful model for genetics, biochemistry, cell biology, and biotechnology. Plant Physiol 126: 485-493

Yao, J-L., Cohen, D., Atkinson, R., Richardson, K. and Morris, B. (1995) Regeneration of transgenic plants from the commercial apple cultivar Royal Gala. *Plant Cell Reports*, 14, 407-412

Zimmermann I M, Heim M A, Weisshaar B, Uhrig J F (2004) Comprehensive identification of *Arabidopsis thaliana* MYB transcription factors interacting with R/B-like BHLH proteins. Plant J 40: 22-34

TABLE X

SUMMARY OF SEQUENCES

| SEQ ID NO | SPECIES | REF | SEQUENCE TYPE |
|---|---|---|---|
| 1 | *Malus domestica* | Md MYB10 | Polypeptide |
| 2 | *Malus domestica* | Md MYB9 | Polypeptide |
| 3 | *Malus domestica* | Md bHLH3 | Polypeptide |
| 4 | *Malus domestica* | Md bHLH33 | Polypeptide |
| 5 | *Malus domestica* | Md MYB10 | Polynucleotide (cDNA) |
| 6 | *Malus domestica* | Md MYB9 | Polynucleotide (cDNA) |

TABLE X-continued

SUMMARY OF SEQUENCES

| SEQ ID NO | SPECIES | REF | SEQUENCE TYPE |
|---|---|---|---|
| 7 | *Malus domestica* | Md bHLH3 | Polynucleotide (cDNA) |
| 8 | *Malus domesitca* | Md bHLH33 | Polynucleotide (cDNA) |
| 9 | *Malus sylvestris* | Ms MYB10 | Polypeptide |
| 10 | *Pyrus communis* | Pc MYB10 | Polypeptide |
| 11 | *Pyrus pyrifolia* | Ppy MYB10 | Polypeptide |
| 12 | *Pyrus bretschneideri* | Pb MYB10 | Polypeptide |
| 13 | *Cydonia oblonga* | Co MYB10 | Polypeptide |
| 14 | *Prunus salicina* | Ps MBY10 | Polypeptide |
| 15 | *Prunus cerasifera* | Pcf MYB10 | Polypeptide |
| 16 | *Prunus persica* | Ppr MYB10 | Polypeptide |
| 17 | *Eriobotrya japonica* | Ej MYB10 | Polypeptide |
| 18 | *Prunus dulcis* | Pd MYB10 | Polypeptide |
| 19 | *Prunus avium* | Pay MYB10 | Polypeptide |
| 20 | *Mespilus germanica* | Mg MYB10 | Polypeptide |
| 21 | *Prunus domestica* | Pdm MYB10 | Polypeptide |
| 22 | *Malus sylvestris* | Ms MYB10 | Polynucleotide (cDNA) |
| 23 | *Malus sylvestris* | Ms MYB10 | Polynucleotide (gDNA) |
| 24 | *Pyrus communis* | Pc MYB10 | Polynucleotide (cDNA) |
| 25 | *Pyrus communis* | Pc MYB10 | Polynucleotide (cDNA) |
| 26 | *Pyrus communis* | Pc MYB10 | Polynucleotide (gDNA) |
| 27 | *Pyrus pyrifolia* | Ppy MYB10 | Polynucleotide (gDNA) |
| 28 | *Pyrus bretschneideri* | Pb MYB10 | Polynucleotide (cDNA) |
| 29 | *Pyrus bretschneideri* | PB MYB10 | Polynucleotide (gDNA) |
| 30 | *Cydonia oblonga* | Co MYB10 | Polynucleotide (cDNA) |
| 31 | *Cydonia oblonga* | Co MYB10 | Polynucleotide (gDNA) |
| 32 | *Prunus salicina* | Ps MYB10 | Polynucleotide (cDNA) |
| 33 | *Prunus salicina* | Ps MYB10 | Polynucleotide (gDNA) |
| 34 | *Prunus cerasifera* | Pcf MYB10 | Polynucleotide (cDNA) |
| 35 | *Prunus cerasifera* | Pcf MYB10 | Polynucleotide (gDNA) |
| 36 | *Prunus persica* | Ppr MYB10 | Polynucleotide (cDNA) |
| 37 | *Prunus persica* | Ppr MYB10 | Polynucleotide (gDNA) |
| 38 | *Eriobotrya japonica* | Ej MYB10 | Polynucleotide (cDNA) |
| 39 | *Eriobotrya japonica* | Ej MYB10 | Polynucleotide (gDNA) |
| 40 | *Prunus dulcis* | Pd MYB10 | Polynucleotide (cDNA) |
| 41 | *Prunus dulcis* | Pd MYB10 | Polynucleotide (gDNA) |
| 42 | *Prunus avium* | Pay MYB10 | Polynucleotide (cDNA) |
| 43 | *Prunus avium* | Pay MYB10 | Polynucleotide (gDNA) |
| 44 | *Mespilus germanica* | Mg MYB10 | Polynucleotide (cDNA) |
| 45 | *Mespilus germanica* | Mg MYB10 | Polynucleotide (gDNA) |
| 46 | *Prunus domestica* | Pdm MYB10 | Polynucleotide (cDNA) |
| 47 | *Prunus domestica* | Pdm MYB10 | Polynucleotide (gDNA) |
| 48 | Artificial/Primer | RE73 | Polynucleotide |
| 49 | Artificial/Primer | RE77R | Polynucleotide |
| 50 | Artificial/Primer | RE78R | Polynucleotide |
| 51 | Artificial/Primer | RE79R | Polynucleotide |
| 52 | Artificial/Primer | RL95F | Polynucleotide |
| 53 | Artificial/Primer | RE96R | Polynucleotide |
| 54 | Artificial/Primer | RE108F | Polynucleotide |
| 55 | Artificial/Primer | RB109R | Polynucleotide |
| 56 | Artificial/Primer | RE120F | Polynucleotide |
| 57 | Artificial/Primer | RE121R | Polynucleotide |
| 58 | Artificial/Primer | KL Ms1F | Polynucleotide |
| 59 | Artificial/Primer | KL Ms2R | Polynucleotide |
| 60 | Artificial/Primer | KL Md PAP1F | Polynucleotide |
| 61 | Artificial/Primer | KL MdPAP1R | Polynucleotide |
| 62 | Artificial/Primer | KL PefF | Polynucleotide |
| 63 | Artificial/Primer | KL PcfR | Polynucleotide |
| 64 | Artificial/Primer | KL Pcf2F | Polynucleotide |
| 65 | Artificial/Primer | KL Pcf3R | Polynucleotide |
| 66 | Artificial/Primer | KL Pcf4R | Polynucleotide |
| 67 | Artificial/Primer | KL Ppr1F | Polynucleotide |
| 68 | Artificial/Primer | KL Ppr2R | Polynucleotide |
| 69 | Artificial/Primer | KL Ppr3F | Polynucleotide |
| 70 | Artificial/Primer | KL Ppr4R | Polynucleotide |
| 71 | Artificial/Primer | KL Fv1F | Polynucleotide |
| 72 | Artificial/Primer | KL Fv2R | Polynucleotide |
| 73 | Artificial/Primer | KL Fv6R | Polynucleotide |
| 74 | Artificial/Primer | KL Fv7F | Polynucleotide |
| 75 | Artificial/Primer | KL Rh1F | Polynucleotide |
| 76 | Artificial/Primer | KL Rh2R | Polynucleotide |
| 77 | Artificial/Primer | KL Rh3F | Polynucleotide |
| 78 | Artificial/Primer | KL Rh4R | Polynucleotide |
| 79 | Artificial/Primer | KL Rosa deg 1F (degenerate primer with a 64 fold degeneracy) | Polynucleotide |
| 80 | Artificial/Primer | KL Rosa deg 2R (degenerate primer with a 16 fold degeneracy) | Polynucleotide |
| 81 | Artificial/Primer | CN944824 mdCHS forward | Polynucleotide |
| 82 | Artificial/Primer | CN944824 MdCHS reverse | Polynucleotide |
| 83 | Artificial/Primer | CN946541 MdCHI forward | Polynucleotide |
| 84 | Artificial/Primer | CN 946541 MdCHI reverse | Polynucleotide |
| 85 | Artificial/Primer | CN491664 MdF3H forward | Polynucleotide |
| 86 | Artificial/Primer | CN491664 MdF3H reverse | Polynucleotide |
| 87 | Artificial/Primer | AY227729 MdDFR forward | Polynucleotide |
| 88 | Artificial/Primer | AY227729 MdDFR reverse | Polynucleotide |
| 89 | Artificial/Primer | AF117269MdLDOX forward | Polynucleotide |
| 90 | Artificial/Primer | AF117269MdLDOX reverse | Polynucleotide |
| 91 | Artificial/Primer | AF117267MdUFGT forward | Polynucleotide |
| 92 | Artificial/Primer | AF117267MdUFGT reverse | Polynucleotide |
| 93 | Artificial/Primer | MdMYB10 forward | Polynucleotide |
| 94 | Artificial/Primer | MdMYB10 reverse | Polynucleotide |
| 95 | Artificial/Primer | MdbHLH33 forward | Polynucleotide |
| 96 | Artificial/Primer | MdbHLH33 reverse | Polynucleotide |
| 97 | Artificial/Primer | CN934367 MdbHLH3 forward | Polynucleotide |
| 98 | Artificial/Primer | CN934367 MdbHLH3 reverse | Polynucleotide |
| 99 | Artificial/Primer | CN938023 MdActin forward | Polynucleotide |
| 100 | Artificial/Primer | CN938023 MdActin reverse | Polynucleotide |
| 101 | Artificial | Consensus | Polypeptide |
| 102 | *Malus domestica* | MdMYB10 | Polynucleotide (gDNA |

The invention claimed is:

1. An isolated polynucleotide comprising a nucleotide sequence encoding a polypeptide having at least 90% sequence identity to the amino acid sequence of SEQ ID NO:1, wherein % identity is calculated over the whole length of the amino acid sequence, and wherein the polypeptide is a transcription factor that increases anthocyanin production upon expression in a plant.

2. The isolated polynucleotide of claim 1, wherein the polypeptide has the amino acid sequence of SEQ ID NO:1.

3. The isolated polynucleotide of claim 1, wherein the nucleotide sequence encoding the polypeptide has at least 90% sequence identity to the coding nucleotide sequence of SEQ ID NO:5 or SEQ ID NO:102.

4. The isolated polynucleotide of claim 1, wherein the nucleotide sequence encoding the polypeptide has at least 90% sequence identity to the coding nucleotide sequence of SEQ ID NO:5.

5. The isolated polynucleotide of claim 1, wherein the nucleotide sequence encoding the polypeptide has the coding nucleotide sequence of SEQ ID NO:5.

6. A genetic construct comprising the polynucleotide of claim 1.

7. A host cell transformed with the polynucleotide of claim 1 to express said polypeptide.

8. A plant cell or plant transformed with the polynucleotide of claim 1 to express said polypeptide, and wherein expression of said polypeptide increases anthocyanin production in said transformed plant cell or plant.

9. An isolated polynucleotide comprising a nucleotide sequence encoding a polypeptide having at least 90% sequence identity to the amino acid sequence of SEQ ID NO:1, wherein % identity is calculated over the whole length of the amino acid sequence, and wherein the polypeptide is a transcription factor that up-regulates promoter of a gene involved in the anthocyanin biosynthetic pathway.

10. The polynucleotide of claim 9 wherein the gene encodes dihydroflavolon 4-reductase (DFR).

11. The polynucleotide of claim 9 wherein the gene encodes chalcone synthase (CHS).

12. A genetic construct comprising the polynucleotide of claim 9.

13. A host cell transformed with the polynucleotide of claim 9 to express said polypeptide.

14. A plant cell or plant transformed with the polynucleotide of claim 9 to express said polypeptide, and wherein expression of said polypeptide increases anthocyanin production in said transformed plant cell or plant.

15. A method for producing a plant cell or plant with increased anthocyanin production, the method comprising the steps of transformation of a plant cell or plant with the polynucleotide of claim 1 and expression of the polypeptide encoded by said polynucleotide in the transformed plant cell or plant, and wherein expression of said polypeptide increases anthocyanin production in said transformed plant cell or plant.

16. A plant produced by the method of claim 15.

* * * * *